United States Patent [19]
Zheng et al.

[11] Patent Number: 5,840,925
[45] Date of Patent: Nov. 24, 1998

[54] TRIOXANE DIMER COMPOUNDS HAVING ANTIPROLIFERATIVE AND ANTITUMOR ACTIVITIES

[75] Inventors: Qun Y. Zheng, Wayne, N.J.; Christopher Murray; Randall J. Daughenbaugh, both of Longmont, Colo.; Poonsakdi Ploypradith; Gary H. Posner, both of Baltimore, Md.

[73] Assignee: Hauser, Inc., Boulder, Colo.

[21] Appl. No.: 759,254

[22] Filed: Dec. 2, 1996

Related U.S. Application Data

[63] Continuation-in-part of Ser. No. 496,771, Jun. 29, 1995, Pat. No. 5,677,468.

[51] Int. Cl.[6] .................................................. C07D 321/02
[52] U.S. Cl. .................... 549/349; 549/220; 546/281.7
[58] Field of Search ..................... 549/220, 349; 546/281.7

[56] References Cited

U.S. PATENT DOCUMENTS 5,225,437   7/1993   Posner et al. ............................ 514/450

OTHER PUBLICATIONS

"Rational Design, Synthesis and Mechanistic Studies of Endoperoxides Structurally Related to Artemisinin," dissertation submitted to The Johns Hopkins University, Dasong Wang (1996).

"Extraordinarily Potent Antimalarial Compounds: New, Structurally Simple, Easily Synthesized, Tricyclic 1,2,4–Trioxanes," Gary H. Posner, et al., *J. Med. Chem.*, 35:2459–2467 (1992).

"Cytotoxicity of Artemisinin–Related Endoperoxides to Ehrlich Ascites Tumor Cells," *J. of Natural Products*, 56(6):849–856 (1993).

"Antimalarial Activity of Novel Ring–Contracted Artemisinin Derivatives," B. Venugopalan, et al., *J. Med. Chem.*, 38:1922–1927.

"Antimalarial activity of new ethers and thioethers of dihydroartemisinin," B. Venugopalan, et al., *Eur. J. Med. Chem.* 30:697–706 (1995).

*Primary Examiner*—Johann Richter
*Assistant Examiner*—Laura L. Stockton
*Attorney, Agent, or Firm*—Steven C. Petersen; Chrisman, Bynum & Johnson, P.C.

[57] ABSTRACT

Described herein are novel trioxane dimers of structure

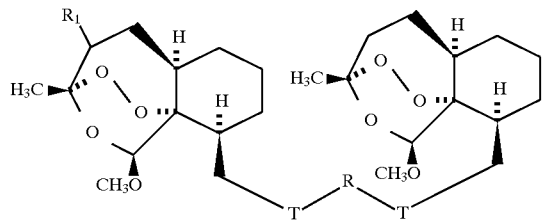

which possess antiproliferative and antitumor activities.

23 Claims, 23 Drawing Sheets

● CALCITRIOL ▲ DIMER 13
◇ DIMER 12 ▼ DIMER 23 ■ DIMER 9

● CALCITRIOL ▽ DIMER 20
▲ DIMER 21 ■ DIMER 22

○ CONTROL
● CALCITRIOL  □ DIMER 13β
▽ DIMER 11   ▼ DIMER 13α

● CALCITRIOL  ▼ DIMER 7
▽ DIMER 8

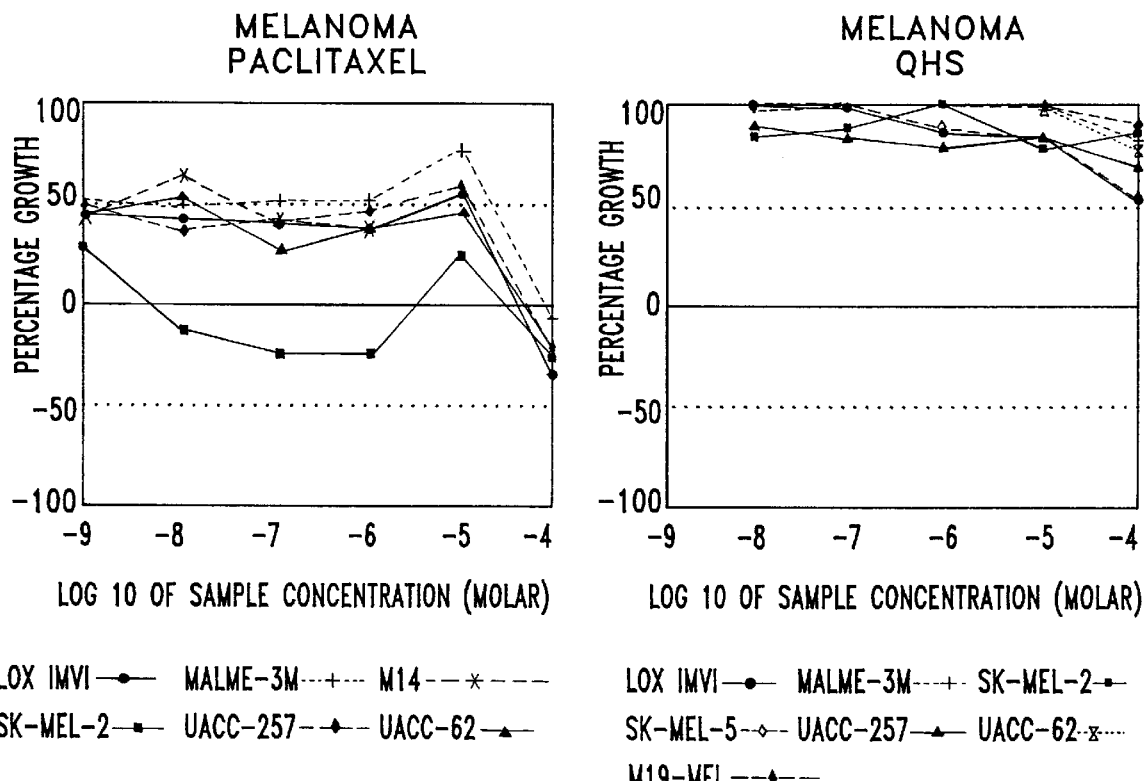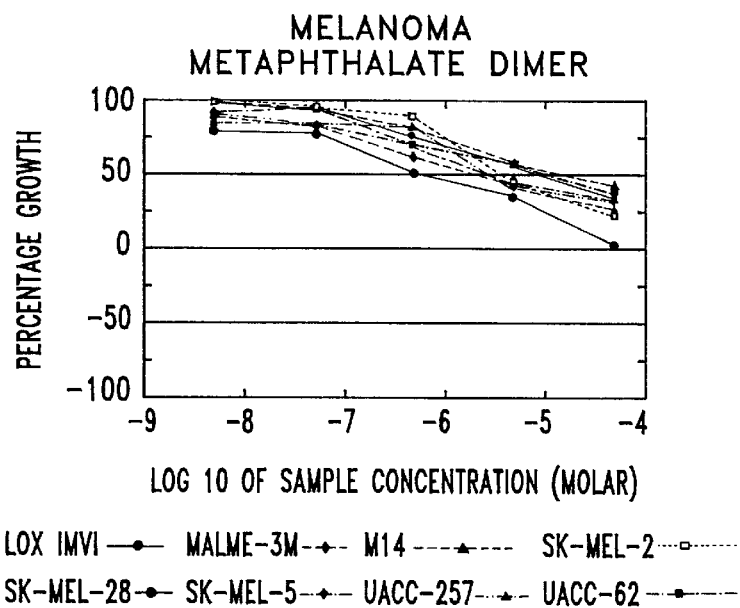

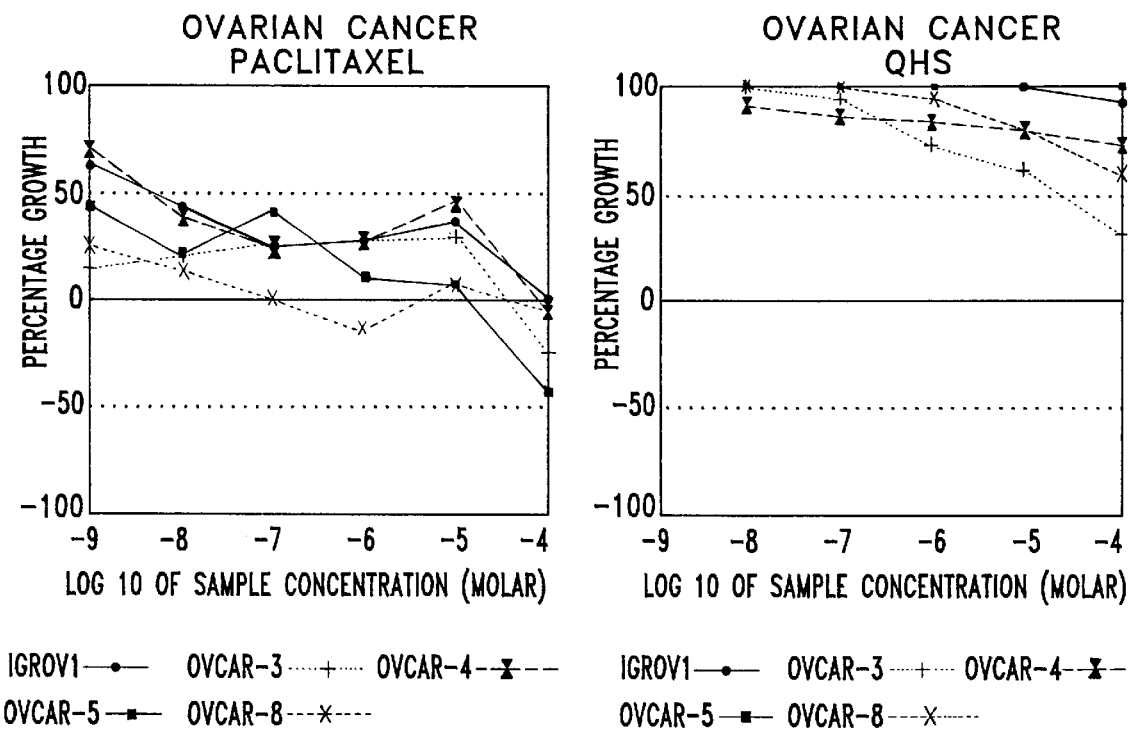
FIG. 15a
FIG. 15b
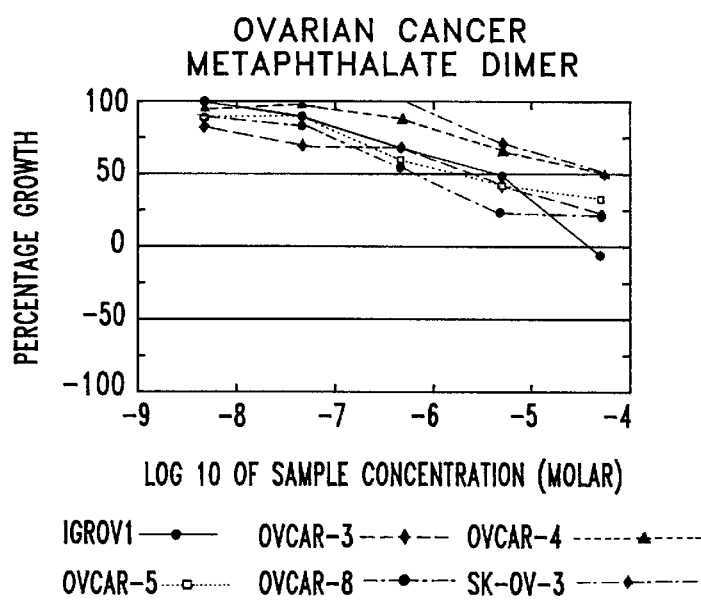
FIG. 15c

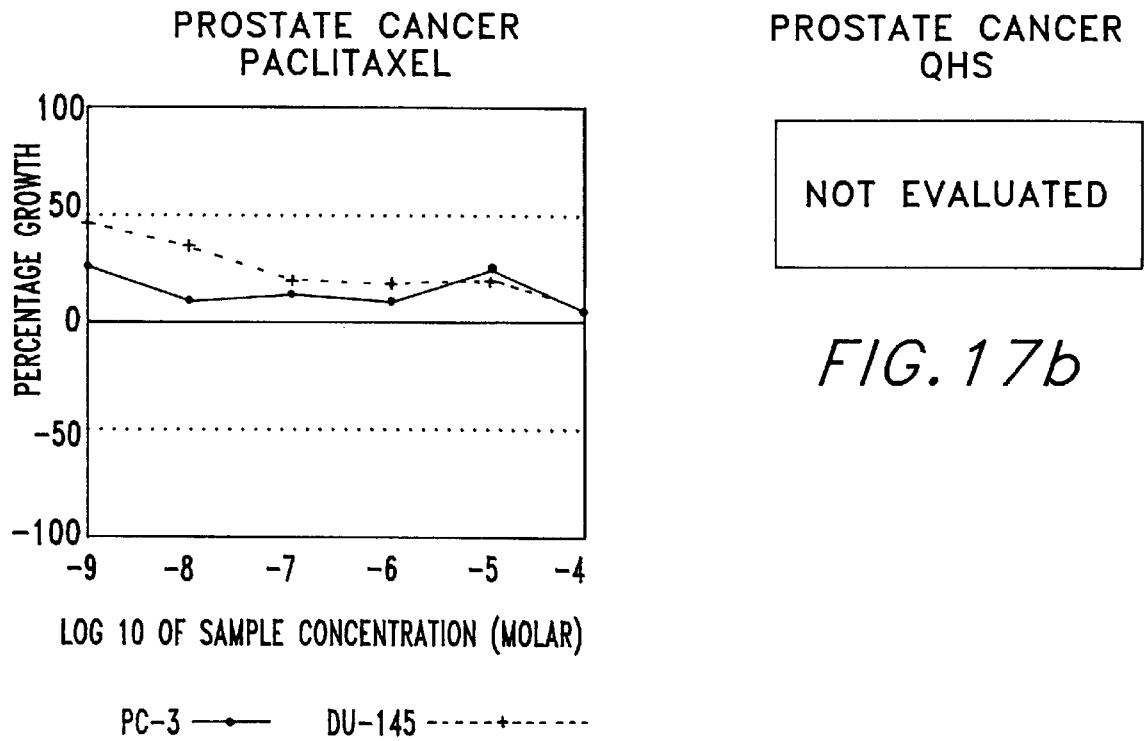
FIG. 17a
FIG. 17b
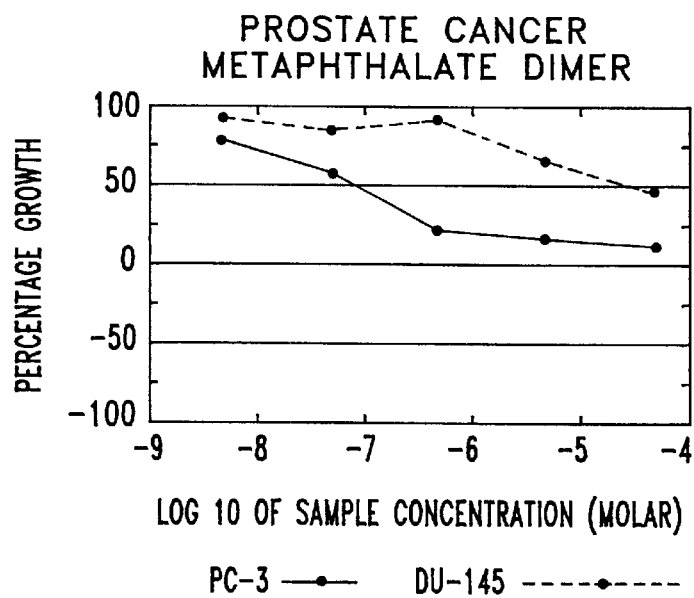
FIG. 17c

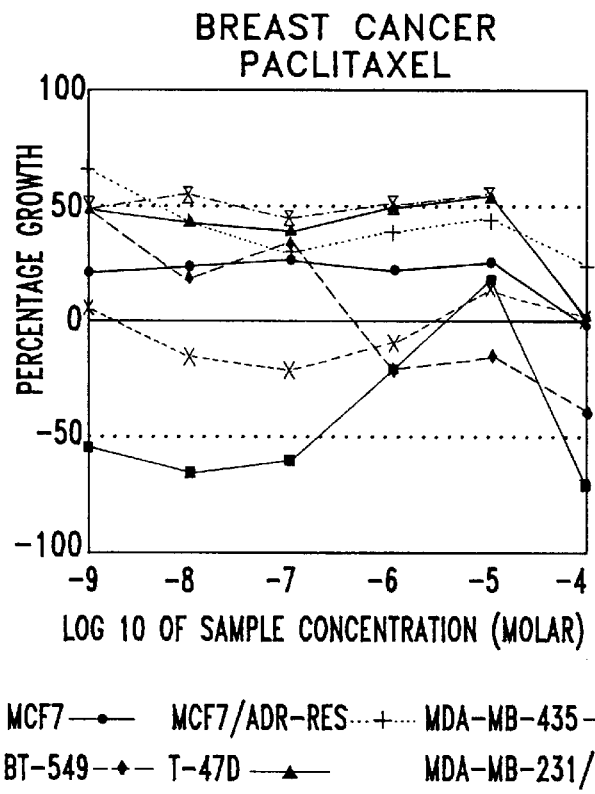
FIG. 18a
BREAST CANCER QHS
NOT EVALUATED
FIG. 18b
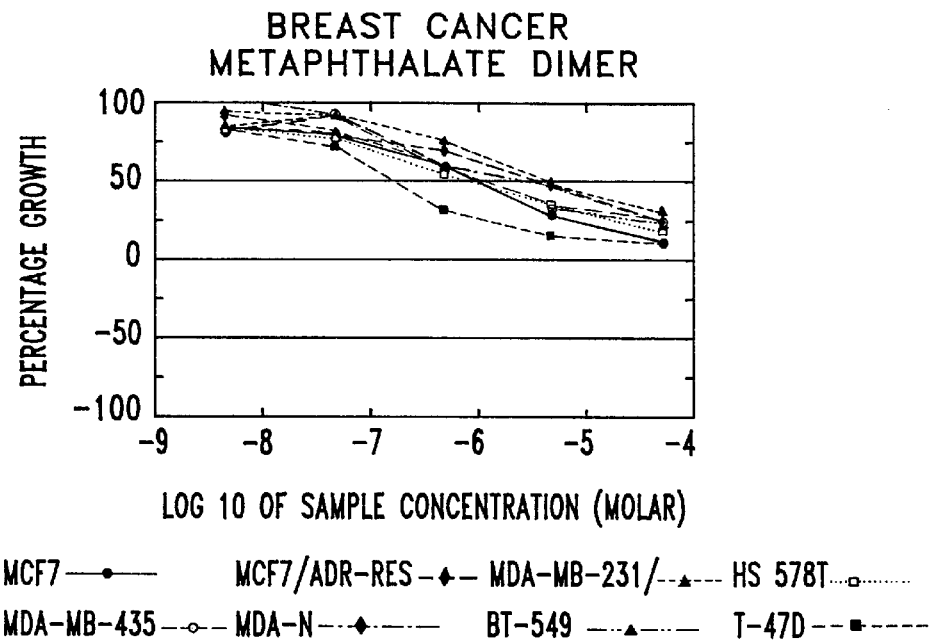
FIG. 18c

TRIOXANE DIMER COMPOUNDS HAVING ANTIPROLIFERATIVE AND ANTITUMOR ACTIVITIES

CROSS-REFERENCE TO OTHER APPLICATIONS

This patent application is a continuation-in-part of U.S. patent application Ser. No. 08/496,771, filed Jun. 29, 1995 now U.S. Pat. No. 5,677,468, and entitled Artemisinin Dimer Compounds Having Anticancer Activities.

CONTRACTUAL ORIGIN OF THE INVENTION

The study was supported by National Institutes of Health grant AI 34885 (to G. H. P.) and joint inventors G. H. P. and P. P. have assigned their rights to the Johns Hopkins University.

BACKGROUND OF THE INVENTION

1. Field of the Invention

The present invention relates to a novel class of trioxane dimers which demonstrate potent and potentially therapeutically valuable antiproliferative and antitumor activities.

2. Description of the State of Art

*Artemisia annua* L., also known as qing hao or sweet wormwood, is a pervasive weed that has been used for many centuries in Chinese traditional medicine as a treatment for fever and malaria. Its earliest mention, for use in hemorrhoids, occurs in the *Recipes for 52 Kinds of Diseases* found in the Mawangdui Han dynasty tomb dating from 168 B.C. Nearly, five hundred years later Ge Hong wrote the *Zhou Hou Bei Ji Fang* (Handbook of Prescriptions for Emergency Treatments) in which he advised that a water extract of qing hao was effective at reducing fevers. In 1596, Li Shizhen, the famous herbalist, wrote that chills and fever of malaria can be combatted by qing hao preparations. Finally, in 1971, Chinese chemists isolated from the leafy portions of the plant the substance responsible for its reputed medicinal action. This crystalline compound, called qinghaosu, also referred to as QHS or artemisinin, is a sesquiterpene lactone with an internal peroxide linkage.

Artemisinin (3,6,9-trimethyl-9,10b-epi-dioxyperhydropyranol[4,3,2-jk]benzoxepin-2-one) is a member of the amorphane subgroup of cadinenes and has the following structure (I).

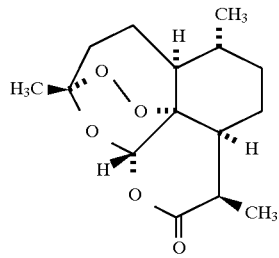

I

Artemisinin or QHS was the subject of a 1979 study conducted by the Qinghaosu Antimalarial Coordinating Research Group involving the treatment of 2099 cases of malaria (*Plasmodium vivax* and *Plasmodium falciparum* in a ratio of about 3:1) with different dosage forms of QHS, leading to the clinical cure of all patients. See, Qinghaosu Antimalarial Coordinating Research Group, *Chin. Med. J.*, 92:811 (1979). Since that time QHS has been used successfully in several thousand malaria patients throughout the world including those infected with both chloroquine-sensitive and chloroquine-resistant strains of *P. falciparum*. Assay of QHS against *P. falciparum*, in vitro, revealed that its potency is comparable to that of chloroquine in two Hanian strains (Z. Ye, et al., *J. Trad. Chin. Med.*, 3:95 (1983)) and of mefloquine in the Camp (cholorquine-susceptible) and Smith (chloroquine-resistant) strains, D. L. Klayman, et al., *J. Nat. Prod.*, 47:715 (1984).

Although QHS is effective at suppressing the parasitemias of *P. vivax* and *P. falciparum*, the problems encountered with recrudescence, and the compound's insolubility in water, led scientists to modify QHS chemically, a difficult task because of the chemical reactivity of the peroxide linkage which is an essential moiety for antimalarial activity.

Reduction of QHS in the presence of sodium borohydride results in the production of dihydroartemesinin (II-1) or DHQHS, (illustrated in structure II below), in which the lactone group is converted to a lactol (hemiacetal) function, with properties similar to QHS. QHS in methanol is reduced with sodium borohydride to an equilibrium mixture of α- and β-isomers of dihydroartemisinin. The yield under controlled conditions is 79% (QHS, 0.85M with NaBH$_4$ 6.34M. 7.5 equivalents in methanol, 12 L at 0°–5° C. for about 3 hours followed by quenching with acetic acid to neutrality at 0°–5° C. and dilution with water to precipitate dihydroartemisinin), A. Brossi, et al., *Journal of Medicinal Chemistry*, 31:645–650 (1988). Using DHQHS as a starting compound a large number of other derivatives, such as,

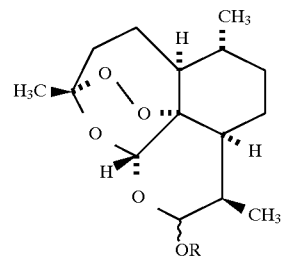

II

1  R = H
2  R = CH$_3$
3  R = CH$_2$CH$_3$
4  R = COCH$_2$CH$_2$COONa
5  R = CH$_2$C$_6$H$_4$COOH
6  R = CH$_2$CC$_6$H$_4$COONa
7  R =

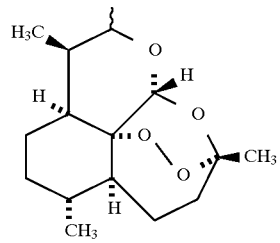

artemether (compound II-2), arteether (II-3), sodium artesunate (II-4), artelinic acid (II-5), sodium artelinate (II-6), DHQHS condensation by-product (II-7) and the olefinic compound, structure III,

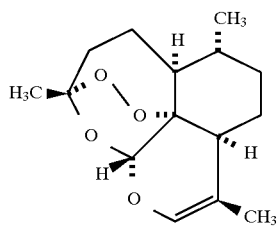

have been produced.

Artemether (II-2) is produced by reacting β-DHQHS with boron trifluoride (BF₃) etherate or HCl in methanol:benzene (1:2) at room temperature. A mixture of β- and α-artemether (70:30) is obtained, from which the former is isolated by column chromatography and recrystallized from hexane or methanol, R. Hynes, *Transactions of the Royal Society of Tropical Medicines and Hygiene*, 88(1): S1/23–S1/26 (1994). For arteether (II-3), (Brossi, et al., 1988), the α-isomer is equilibrated (epimerized) to the β-isomer in ethanol:benzene mixture containing BF₃ etherate. Treatment of DHQHS with an unspecified dehydrating agent yields both the olefinic compound, (III), and the DHQHS condensation by-product (II-7), formed on addition of DHQHS to (III), M. Cao, et al., *Chem. Abstr.*, 100:34720k (1984). Until recently, the secondary hydroxy group in DHQHS (II-1) provided the only site in an active QHS related compound that had been used for derivatization. See B. Venugopalan "Synthesis of a Novel Ring Contracted Artemisinin Derivative," *Bioorganic & Medicinal Chemistry Letters*, 4(5):751–752 (1994).

The potency of various QHS-derivatives in comparison to QHS as a function of the concentration at which the parasitemia is 90 percent suppressed ($SD_{90}$) was reported by D. L. Klayman, "Qinghaosu (Artemisinin): An Antimalarial Drug from China, " *Science* 228:1049–1055 (1985). Dr. Klayman reported that the olefinic compound III, is inactive against *P. berghei*-infected mice, whereas, the DHQHS condensation by-product (II-7), has an $SD_{90}$ of 10 mg/Kg, in *P. berghei-infected* mice. Thus, the DHQHS ether dimer proved to be less potent than QHS, which has an $SD_{90}$ of 6.20 mg/Kg. Following, in order of their overall antimalarial efficacy, are the three types of derivatives of DHQHS (II-1) that have been produced: (QHS)<ethers (II, R=alkyl)<esters [II, R=C(=O)-alkyl or -aryl]<carbonates [II,R=C(=O)0-alkyl or -aryl].

Other rational designs of structurally simpler analogs of artemisinin has led to snythesis of various trioxanes, some of which possess excellent antimalarial activity. Posner, G. H., et al., reported the chemistry and biology of a series of new structurally simple, easily prepared, racemic 1,2,4-trioxanes (disclosed in U.S. Pat. No. 5,225,437 and incorporated herein by reference) that are tricyclic (lacking the lactone ring present in tetracyclic artemisinin I) and that are derivatives of trioxane alcohol IV

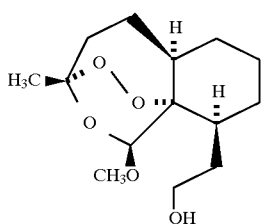

having the relative stereochemistry shown above. Especially attractive features of trioxane alcohol IV are the following: (1) its straightforward and easy preparation from cheap and readily available starting materials, (2) its availability on gram scale, and (3) its easy one-step conversion, using standard chemical transformations, into alcohol derivatives such as esters and ethers, without destruction of the crucial trioxane framework. See, Posner, G. H., et al., J. Med. Chem., 35:2459–2467 (1992), incorporated herein by reference.

Over the past twenty years only a few drugs isolated from higher plants have yielded clinical agents, the outstanding examples being vinblastine and vincristine from the Madagascan periwinkle, *Catharanthus roseus*, etoposide, the semi-synthetic lignan, from May-apple *Podophyllum peltatum* and the diterpenoid taxol, commonly referred to as paclitaxel, from the Pacific yew, *Taxus brevifolia*. Of these agents, paclitaxel is the most exciting, recently receiving approval by the Food and Drug Administration for the treatment of refractory ovarian cancer. Since the isolation of QHS, there has been a concerted effort by investigators to study other therapeutic applications of QHS and its derivatives.

National Institutes of Health reported that QHS is inactive against P388 leukemia. See NCI Report on NSC 369397 (tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that QHS displays very little anticancer activity. A series of artemisinin-related endoperoxides were tested for cytoxicity to Ehrlich ascites tumor (EAT) cells using the microculture tetrazolum (MTT) assay, H. J. Woerdenbag, et al. "Cytotoxicity of Artemisinin-Related Endoperoxides to Ehrlich Ascites Tumor Cells," *Journal of Natural Products*, 56(6):849–856 (1993). The MTT assay, used to test the artemisinin-related endoperoxides for cytoxicity, is based on the metabolic reduction of soluble tetrazolium salts into insoluble colored formazan products by mitochondrial dehydrogenase activity of the tumor cells. As parameters for cytoxicity, the $IC_{50}$ and $IC_{80}$ values, the drug concentrations causing respectively 50% and 80% growth inhibition of the tumor cells, were used. QHS (I), had an $IC_{50}$ value of 29.8 μM. Derivatives of DHQHS (II-1) being developed as antimalarial drugs (artemether (II-2), arteether (III-3), sodium artesunate (II-4), artelinic acid (II-5) and sodium artelinate (II-6)), exhibited a somewhat more potent cytoxicity. Their $IC_{50}$ values ranged from 12.2 μM to 19.9 μM. The DHQHS condensation by-product (II-7), disclosed previously by M. Cao, et al., 1984, was the most potent cytotoxic agent, its $IC_{50}$ being 1.4 μM. At this drug concentration the condensation by-product (II-7), is approximately twenty-two times more cytoxic than QHS and sixty times more cytotoxic than DHQHS (II-1), the parent compound.

There is still a need, therefore, for developing structural analogs of QHS having antiproliferative and antitumor agents that have potency equivalent or greater than known anticancer antiproliferative and antitumor agents.

SUMMARY OF THE INVENTION

Accordingly, it is an object of this invention to provide a class of artemisinin related dimers which demonstrate antiproliferative and antitumor activities.

More specifically, it is an object of this invention to provide a class of trioxane dimers which demonstrate antiproliferative and antitumor activities.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the compositions of this invention comprise 1,2,4-trioxane dimers, of the following structure or diastereomers thereof, having antiproliferative and antitumor activities;

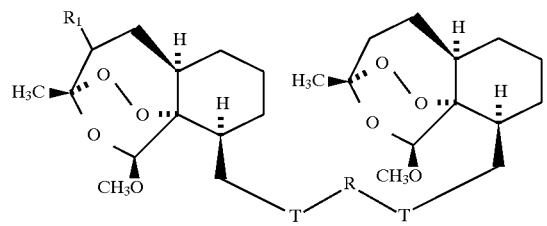

when T is $CH_2O$ and R, being attached to the oxygen, is a linker such as an arylene, hetero-arylene, lower alkylene, lower alkenylene, a bivalent phosphate species, sulfur, oxygen, —$(CH_2CH_2O)_n$— wherein n is 1–20, —$CH_2CH_2$—$(XCH_2CH_2)_n$— where X is O, S or NY where Y is H (hydrogen) or alkyl and n is 0–20, or R is —W—Z—W— where W is a bivalent ester, carbamate or carbonate species and Z is arylene, polyethylene glycol (PEG), hetero-arylene, lower alkylene, or lower alkenylene, and $R_1$ is hydrogen, a methyl group, chloromethylphenyl ($PhCH_2Cl$), dichlorophenyl ($PhCl_2$) or a benzyl group ($PhCH_2$) or in the alternative when T is $CH_2$, R is oxygen and $R_1$ is hydrogen, a methyl group, chloromethylphenyl ($PhCH_2Cl$), dichlorophenyl ($PhCl_2$) or a benzyl group ($PhCH_2$).

BRIEF DESCRIPTION OF THE DRAWINGS

The accompanying drawings, which are incorporated in and form a part of the specification, illustrate the preferred embodiments of the present invention, and together with the description serve to explain the principles of the invention.

In the drawings, FIGS. 1–9, the horizontal axis depicts various dilutions of the test compound, ranging from $10^{-3}$ to $10^{-9}$ molar, that were exposed to murine keratinocytes. The vertical axis (cell number) depicts the number of murine keratinocyte cells present when exposed to a specific concentration of the tested compound as compared to the growth of the same keratinocyte cells not exposed to any compound.

Figure 1:
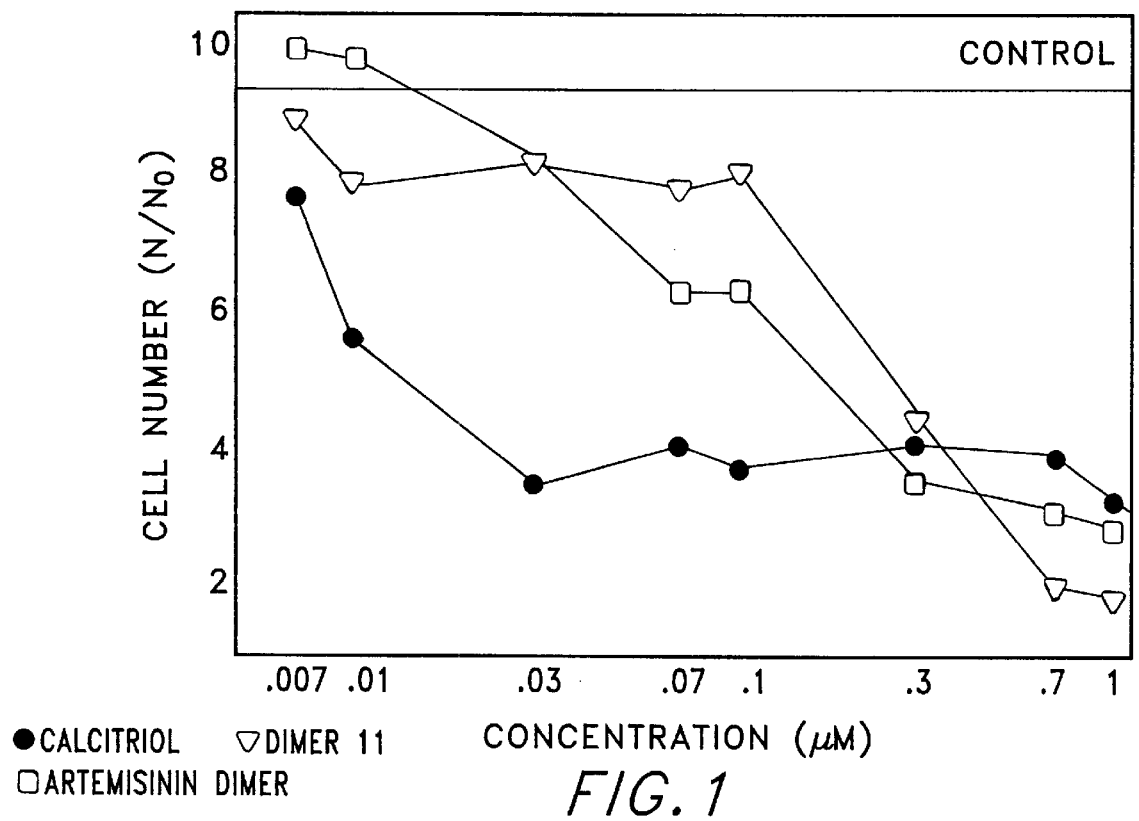

In the drawings, FIGS. 10a–e–18a–e, the horizontal axis depicts various dilutions of the test compound, ranging from $10^{-4}$ to $10^{-9}$ molar, that were exposed to the specified cancer cell lines. The vertical axis (percentage growth) depicts the growth of the specified cancer cell line when exposed to a specific concentration of the tested compound as compared to the growth of the same cancer cell line not exposed to any compound.

In the Drawings

FIG. 1 depicts the dose response curves generated by exposing murine keratinocytes to various concentrations of the trioxane dimer 11 of the present invention versus selected control compounds.

Figure 2:
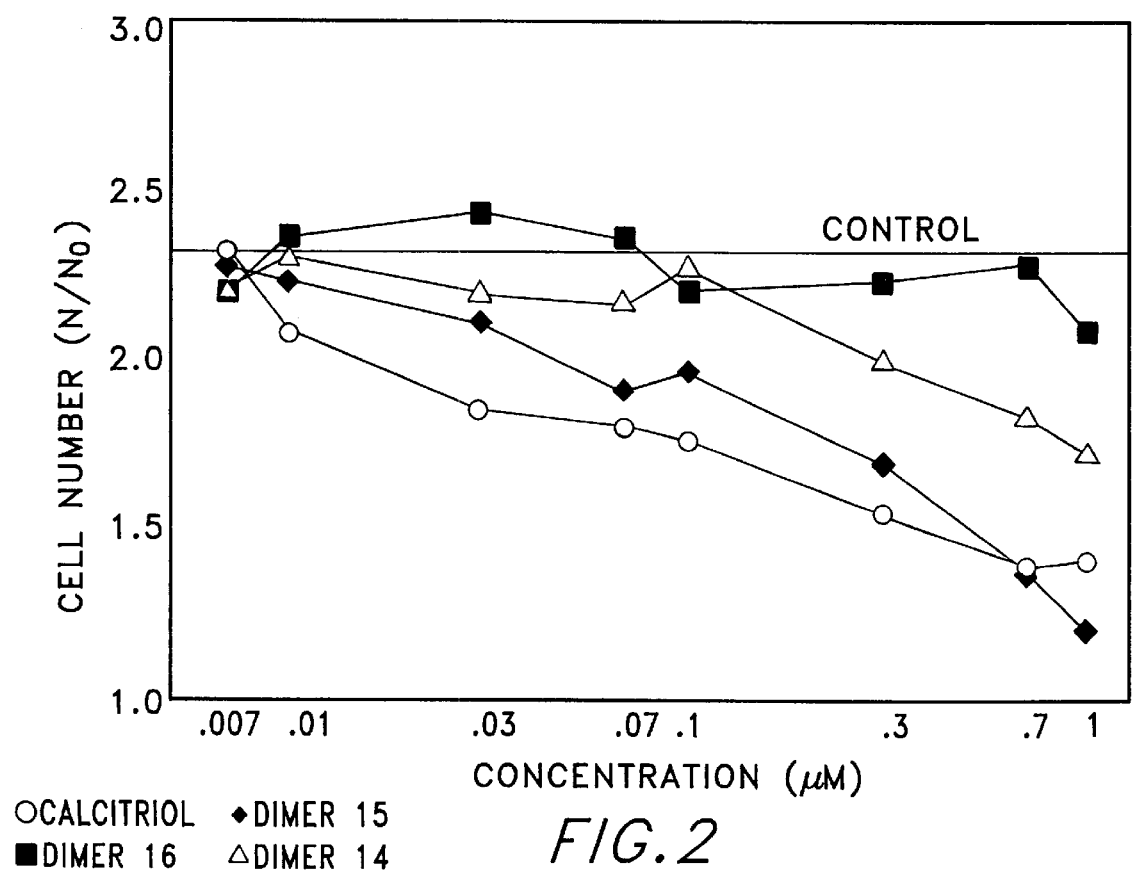

FIG. 2 depicts the dose respose curves generated by exposing murine keratinocytes to various concentrations of the trioxane dimers 14, 15, and 16 of the present invention versus a selected control compound.

Figure 3:
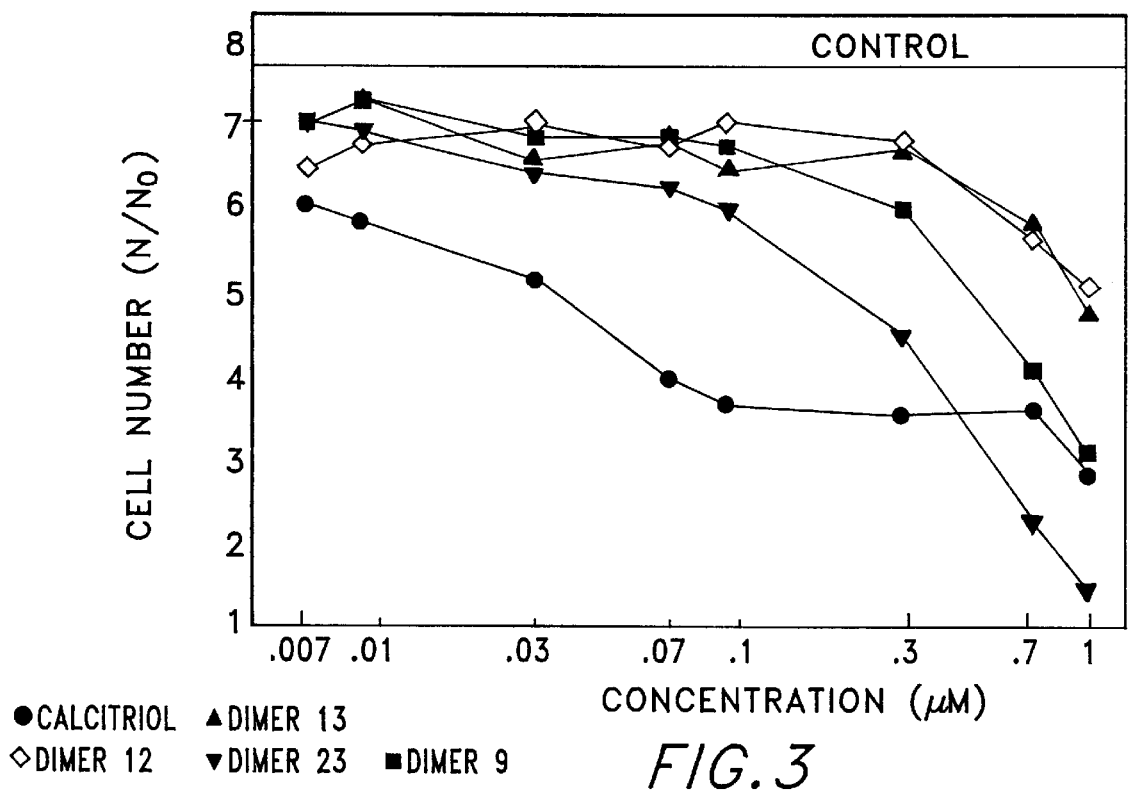

FIG. 3 depicts the dose respose curves generated by exposing murine keratinocytes to various concentrations of the trioxane dimers 9, 12, 13, and 23 of the present invention versus a selected control compound.

Figure 4:
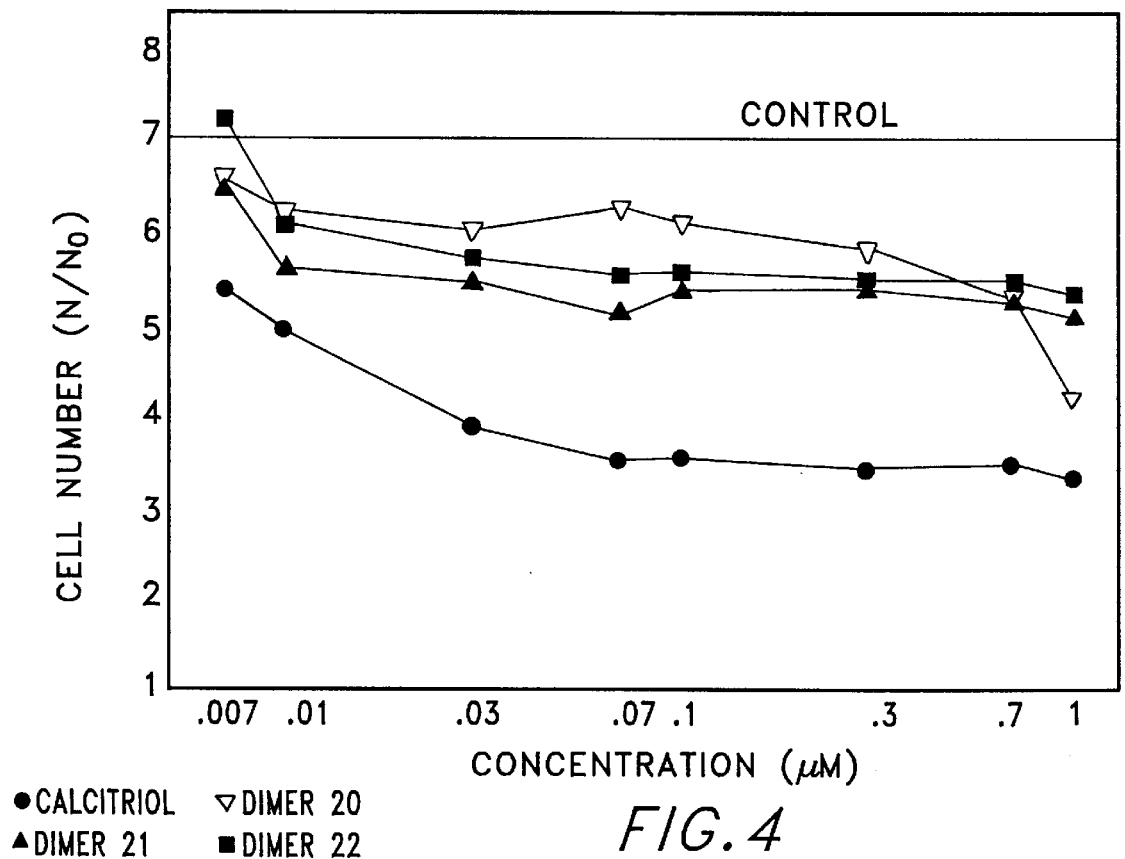

FIG. 4 depicts the dose respose curves generated by exposing murine keratinocytes to various concentrations of the trioxane dimers 20, 21, and 22 of the present invention versus a selected control compound.

Figure 5:
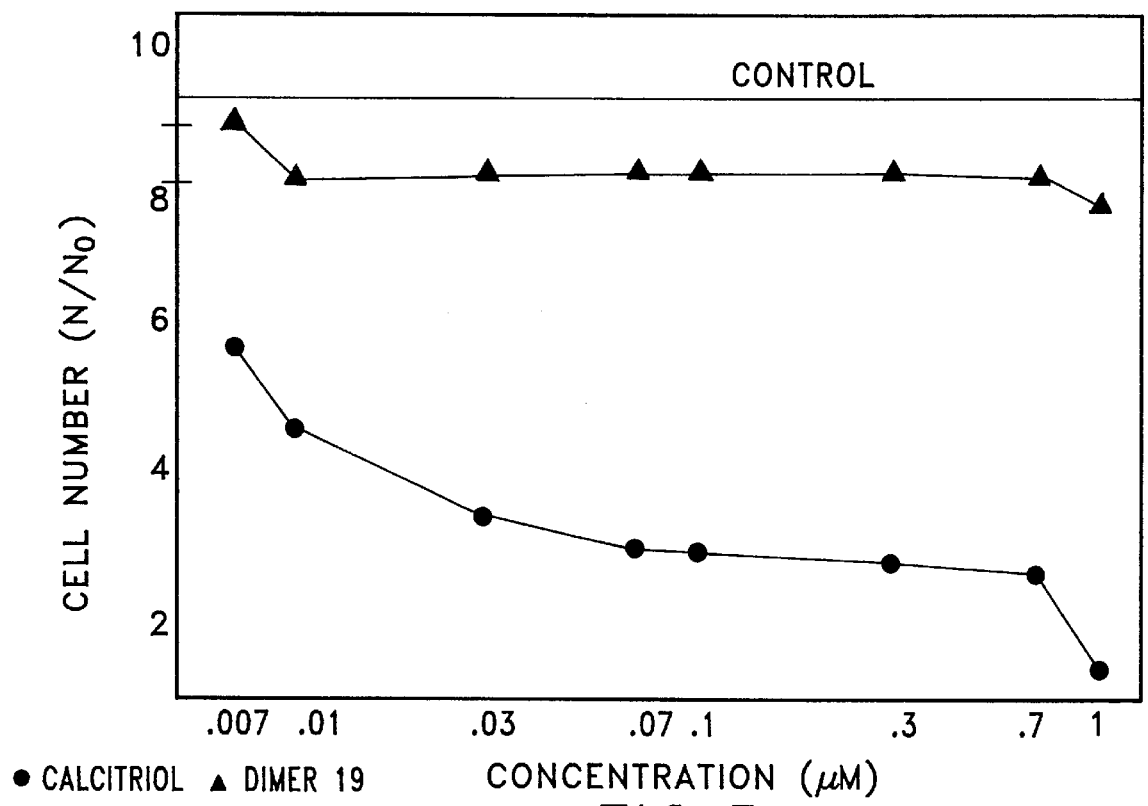

FIG. 5 depicts the dose respose curves generated by exposing murine keratinocytes to various concentrations of the trioxane dimer 19 of the present invention versus a selected control compound.

Figure 6:
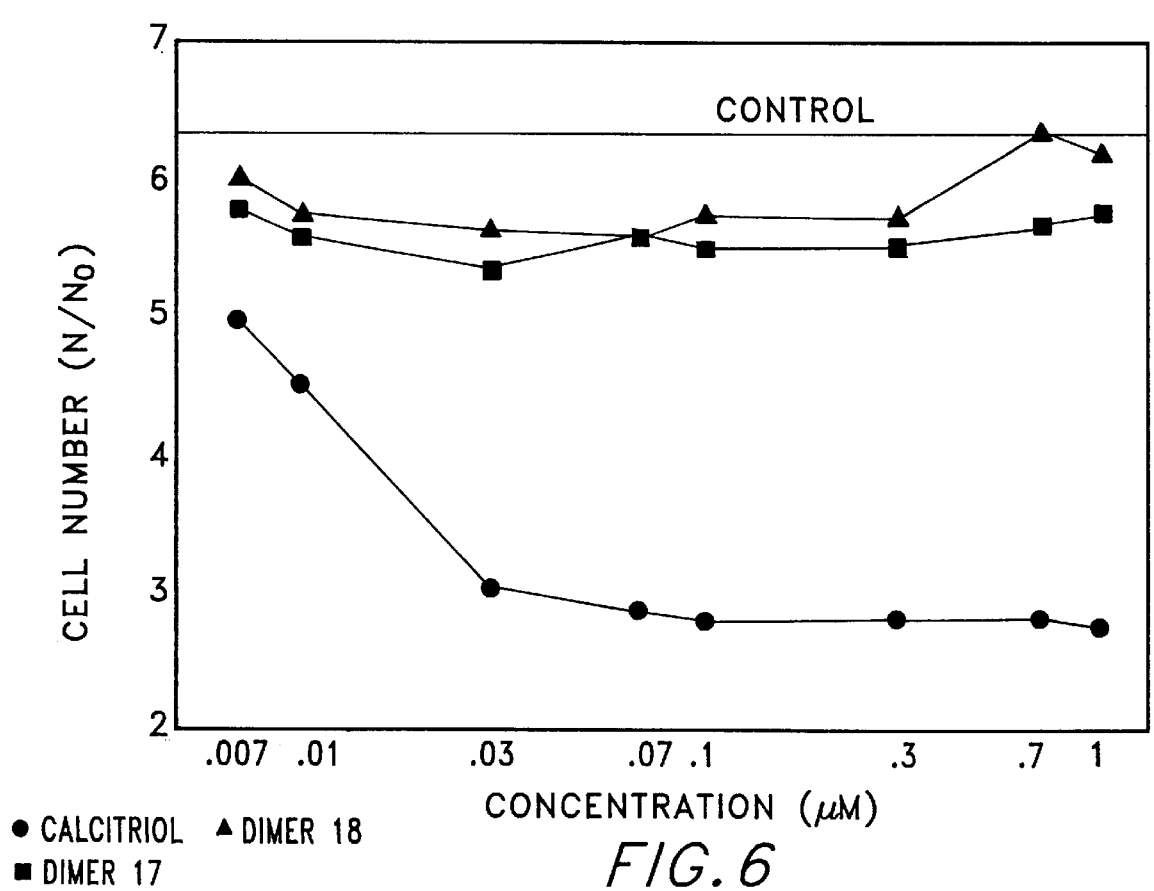

FIG. 6 depicts the dose respose curves generated by exposing murine keratinocytes to various concentrations of the trioxane dimers 17 and 18 of the present invention versus a selected control compound.

Figure 7:
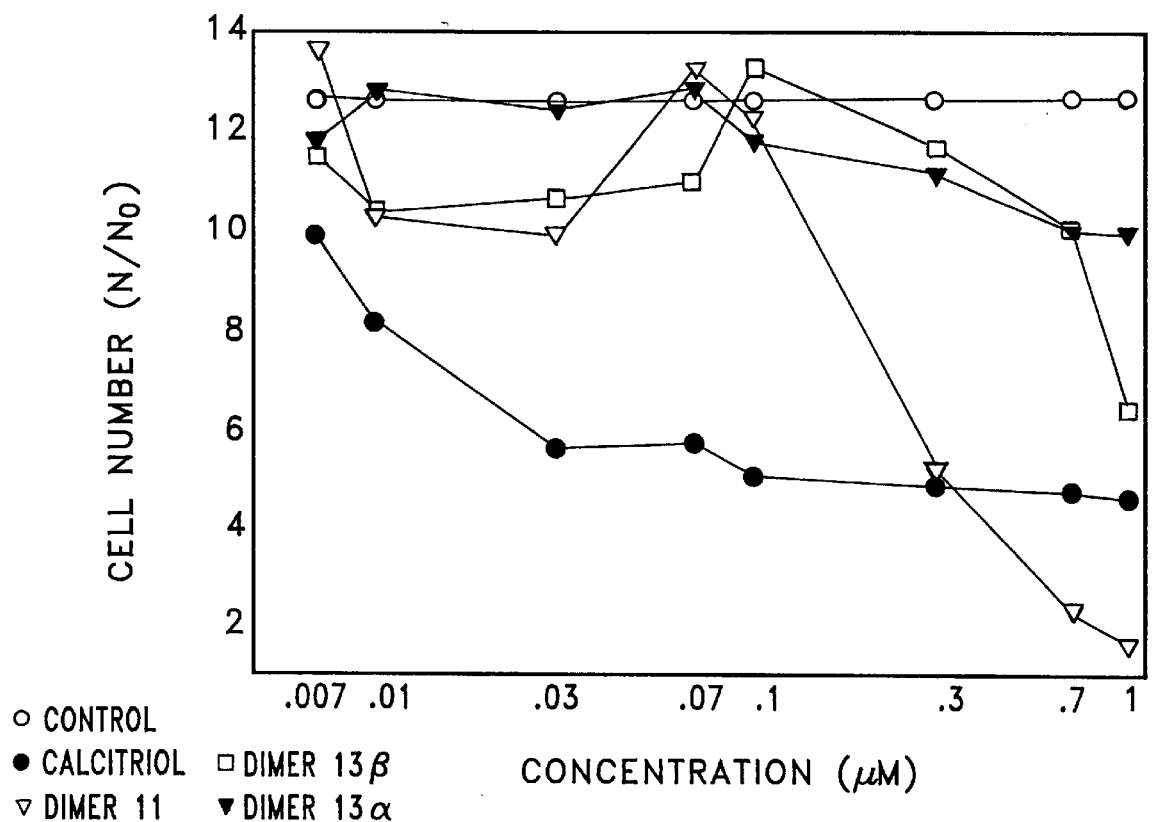

FIG. 7 depicts the dose respose curves generated by exposing murine keratinocytes to various concentrations of the trioxane dimers 11, 13β, and 13α of the present invention versus selected control compounds.

Figure 8:
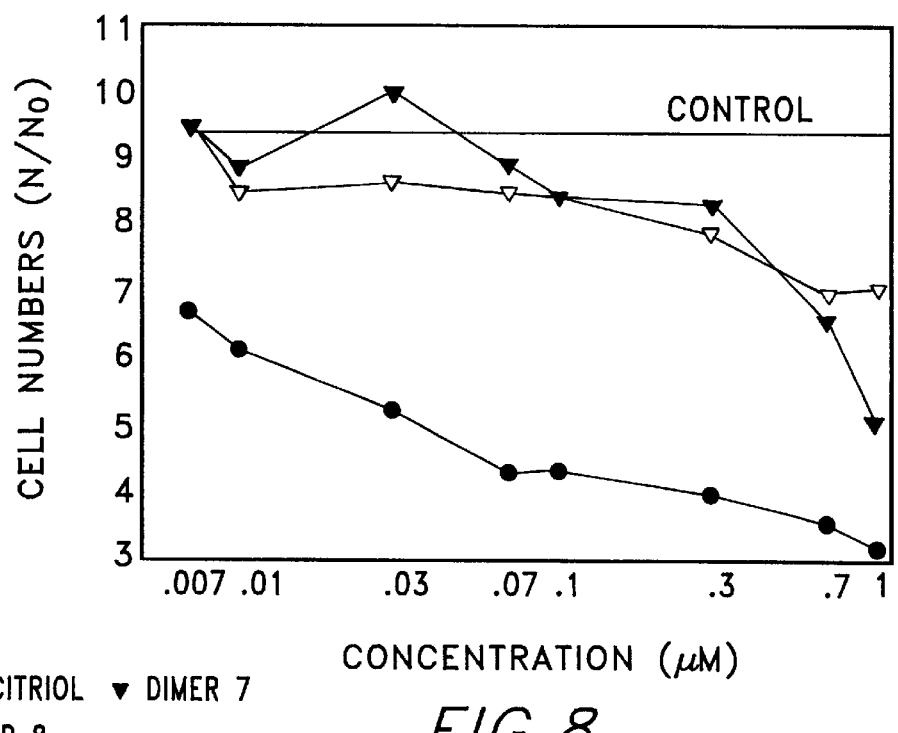

FIG. 8 depicts the dose respose curves generated by exposing murine keratinocytes to various concentrations of the trioxane dimers 7 and 8 of the present invention versus a selected control compound.

Figure 9:
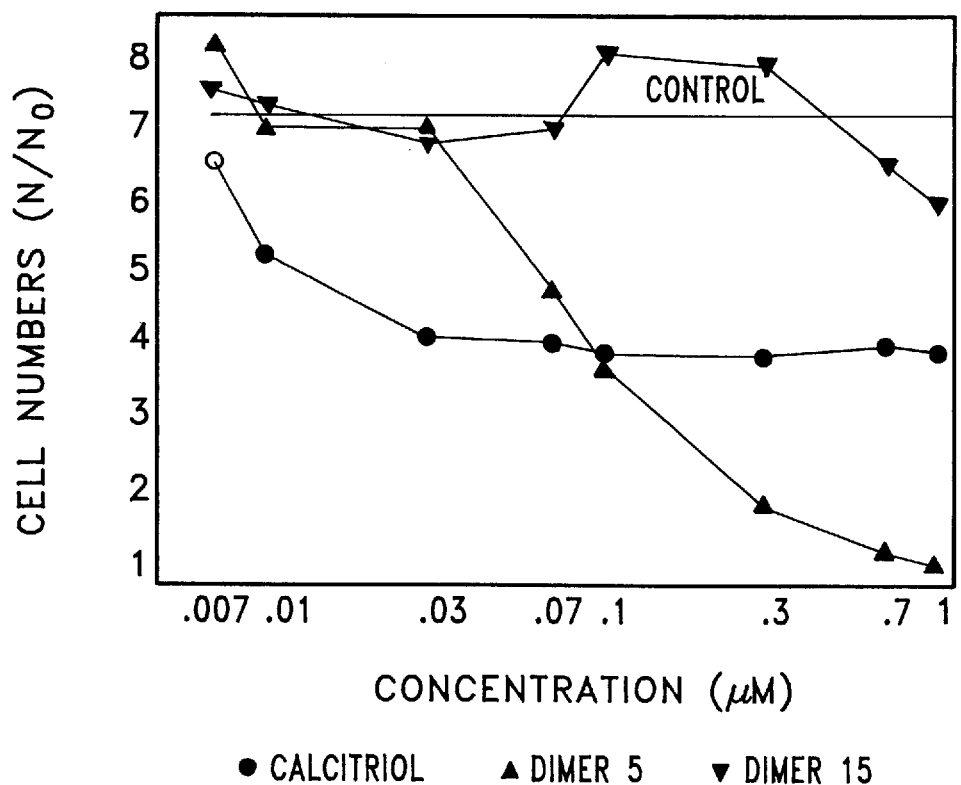

FIG. 9 depicts the dose respose curves generated by exposing murine keratinocytes to various concentrations of the trioxane dimers 5 and 15 of the present invention versus a selected control compound.

Figure 10A:
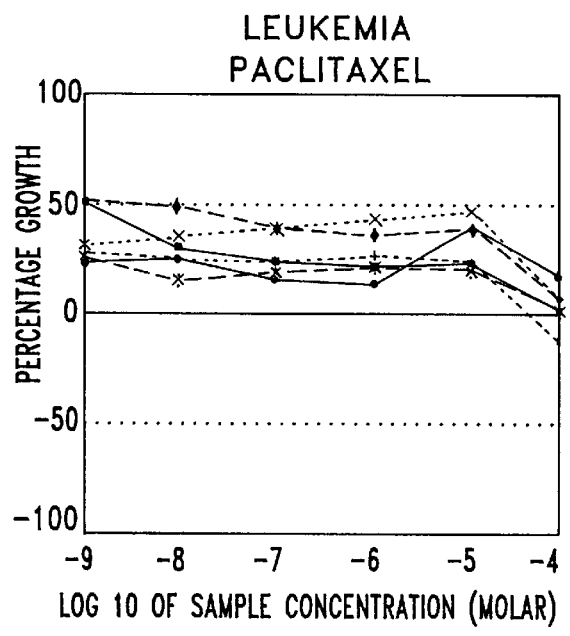

FIG. 10a depicts the dose response curves generated by exposing various leukemia cancer cell lines to various concentrations of paclitaxel.

Figure 10B:
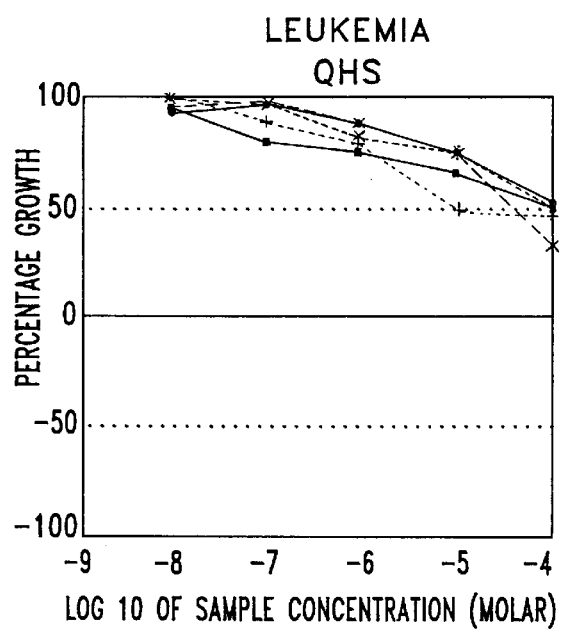

FIG. 10b depicts the dose response curves generated by exposing various leukemia cancer cell lines to various concentrations of QHS.

Figure 10C:
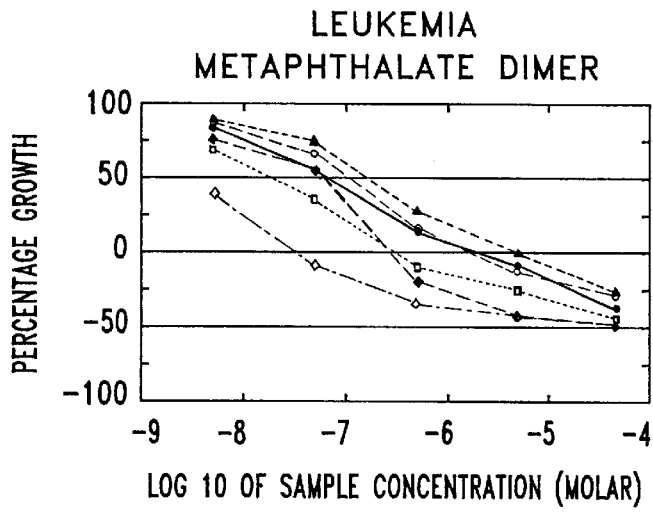

FIG. 10c depicts the dose response curves generated by exposing various leukemia cancer cell lines to various concentrations of the metaphthalate dimer of the present invention.

Figure 10D:
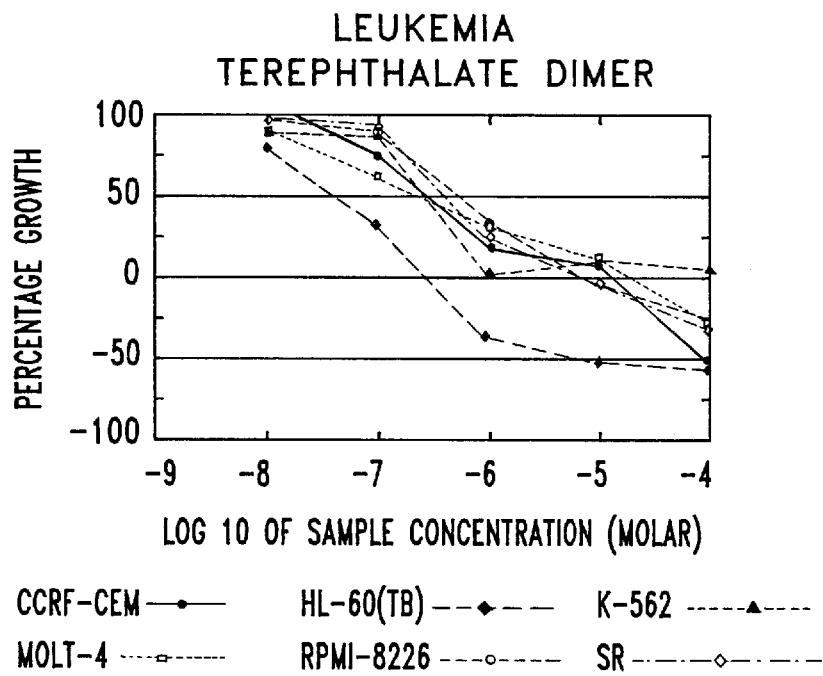

FIG. 10d depicts the dose response curves generated by exposing various leukemia cancer cell lines to various concentrations of the terephthalate dimer of the present invention.

Figure 10E:
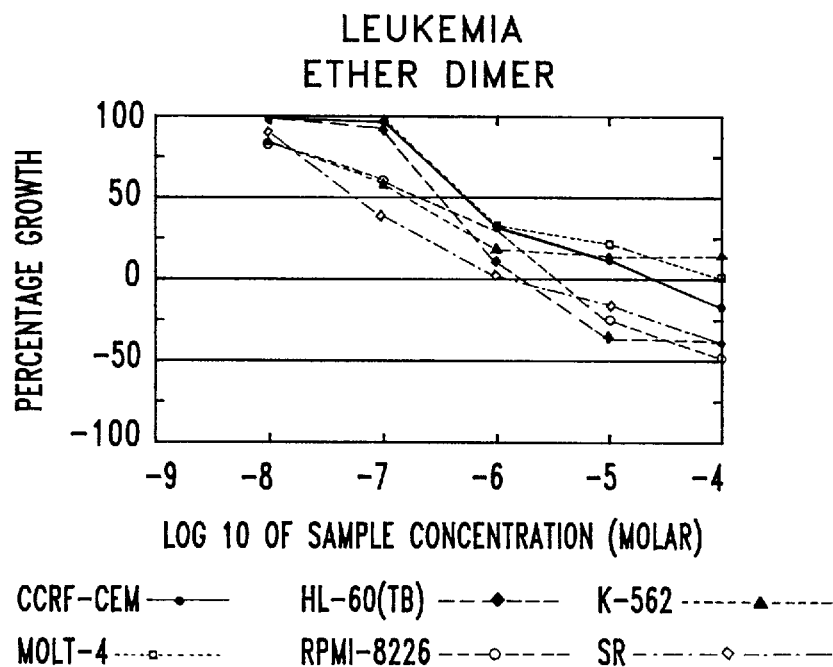

FIG. 10e depicts the dose response curves generated by exposing various leukemia cancer cell lines to various concentrations of the ether dimer of the present invention.

Figure 11A:
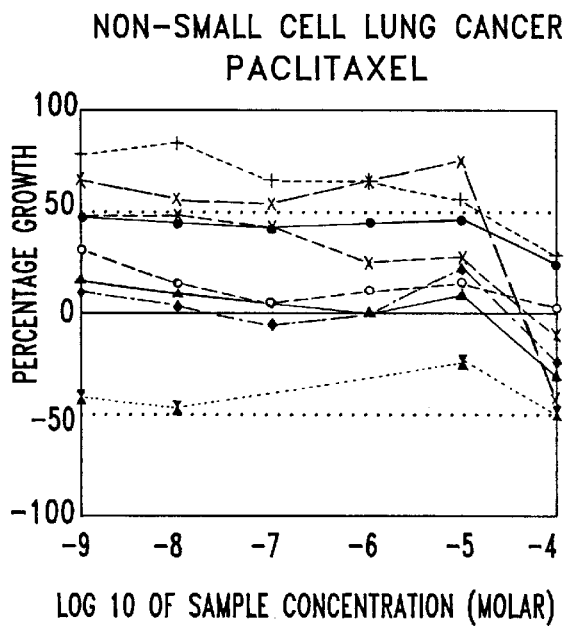

FIG. 11a depicts the dose response curves generated by exposing various non-small cell lung cancer cell lines to various concentrations of paclitaxel.

Figure 11B:
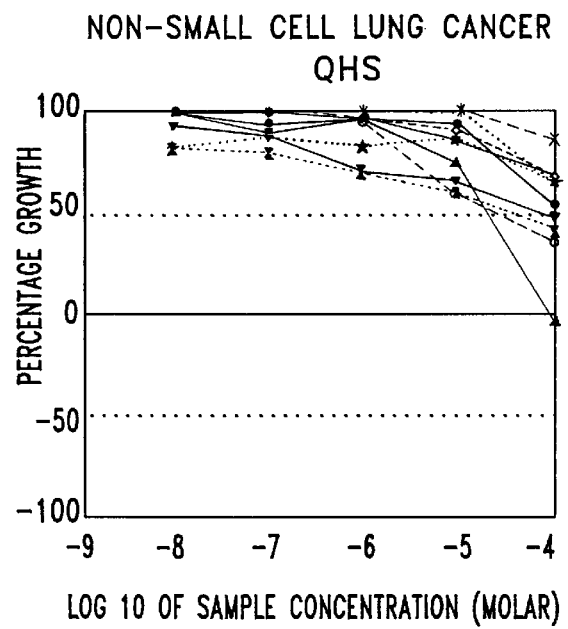

FIG. 11b depicts the dose response curves generated by exposing various non-small cell lung cancer cell lines to various concentrations of the QHS.

Figure 11C:
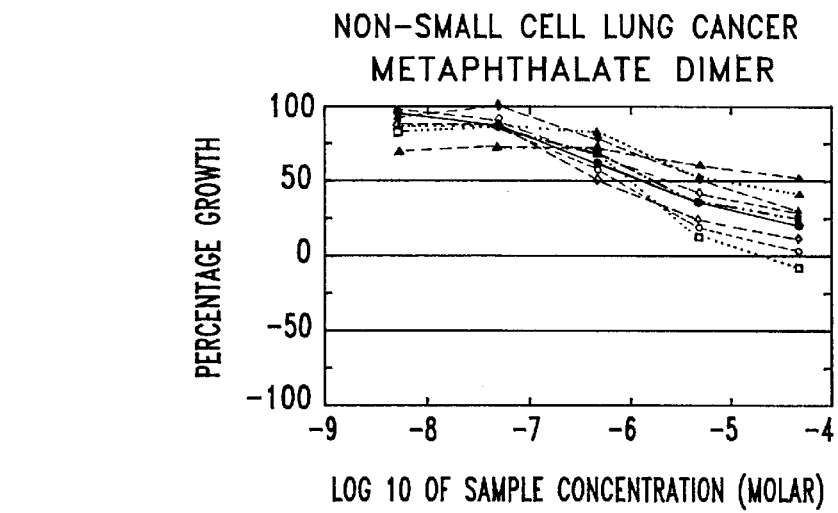

FIG. 11c depicts the dose response curves generated by exposing various non-small cell lung cancer cell lines to various concentrations of the metaphthalate dimer of the present invention.

Figure 11D:
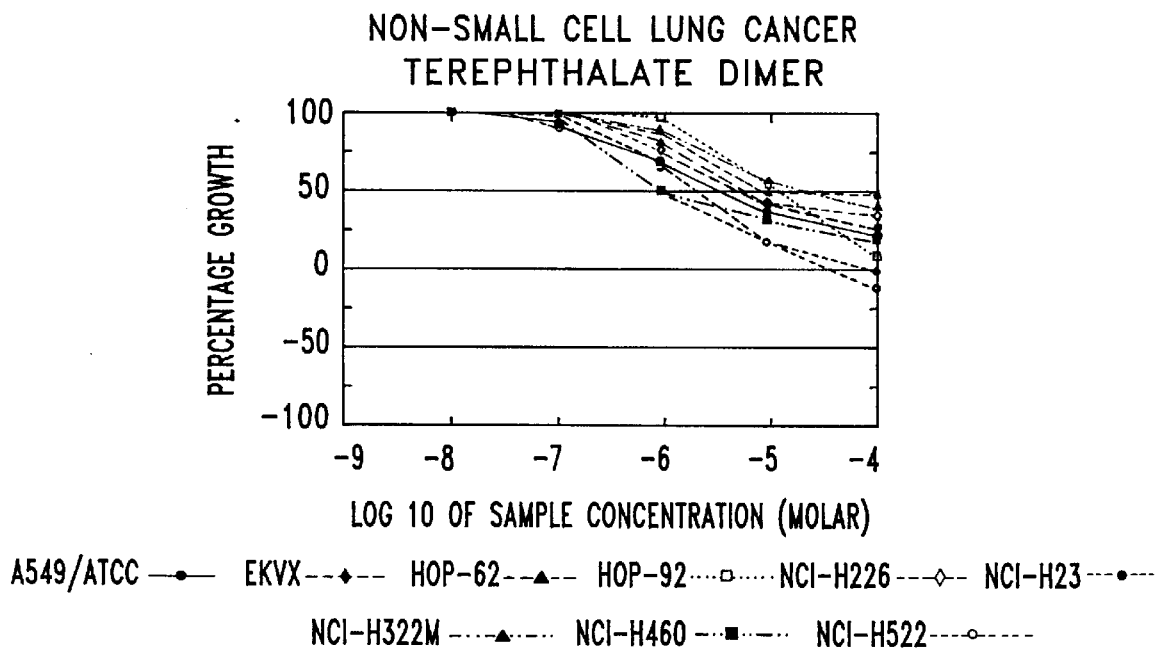

FIG. 11d depicts the dose response curves generated by exposing various non-small cell lung cancer cell lines to various concentrations of the terephthalate dimer of the present invention.

Figure 11E:
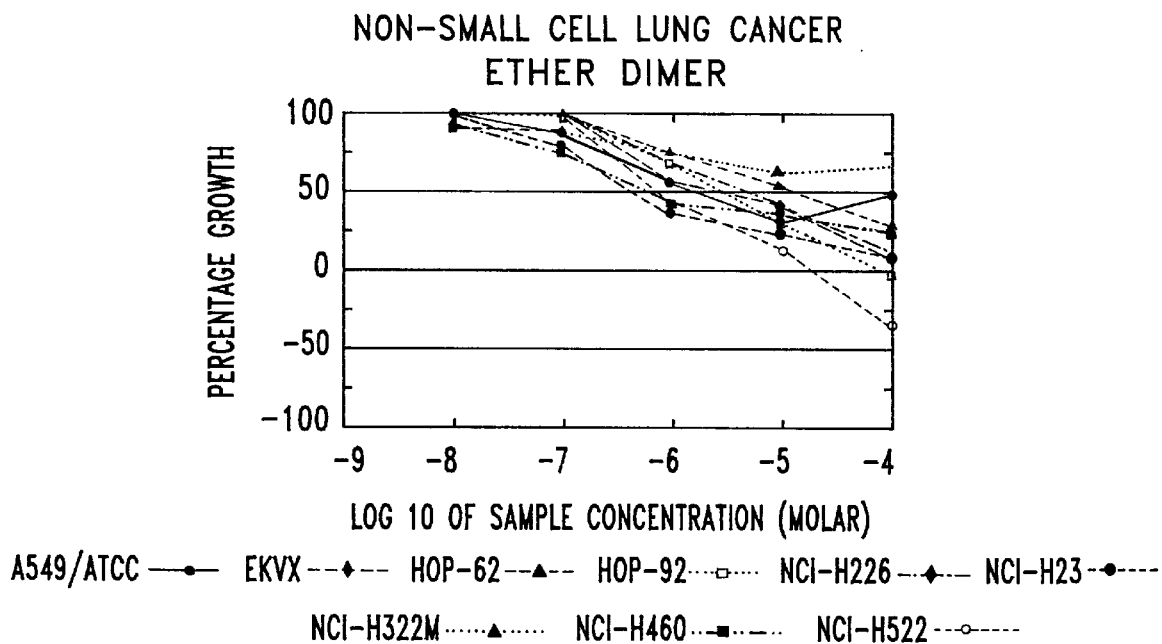

FIG. 11e depicts the dose response curves generated by exposing various non-small cell lung cancer cell lines to various concentrations of the ether dimer of the present invention.

Figure 12A:
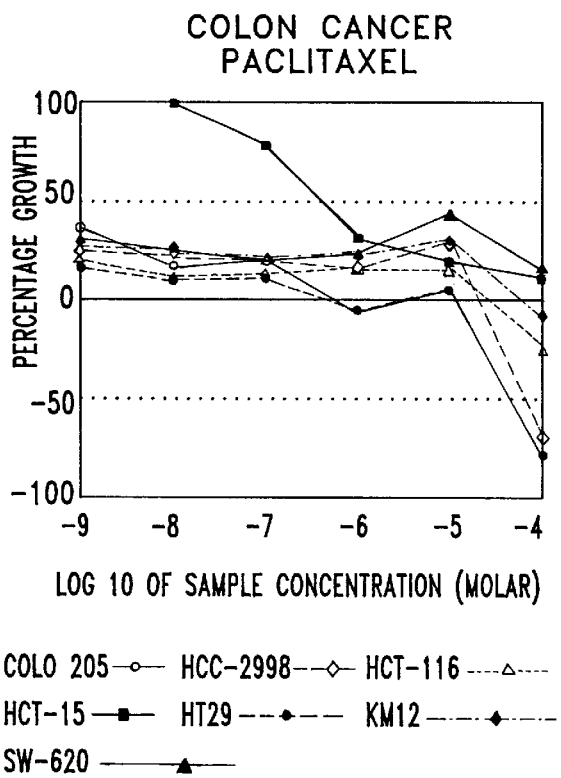

FIG. 12a depicts the dose response curves generated by exposing various colon cancer cell lines to various concentrations of paclitaxel.

Figure 12B:
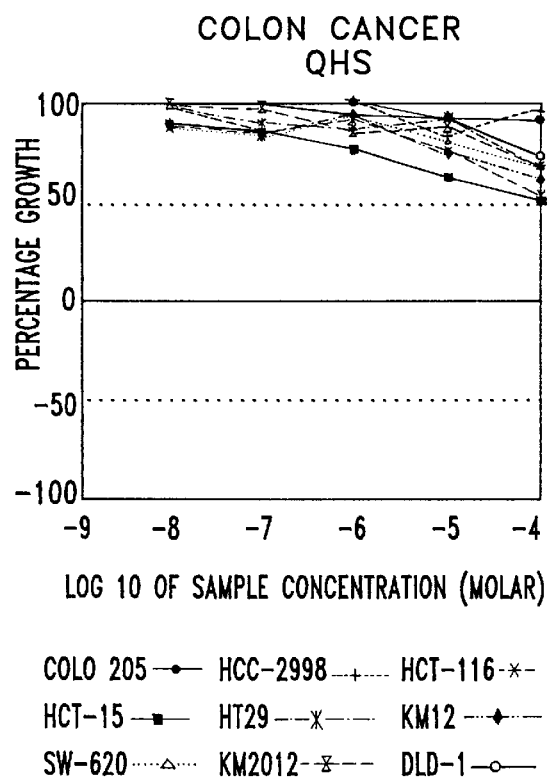

FIG. 12b depicts the dose response curves generated by exposing various colon cancer cell lines to various concentrations of QHS.

Figure 12C:
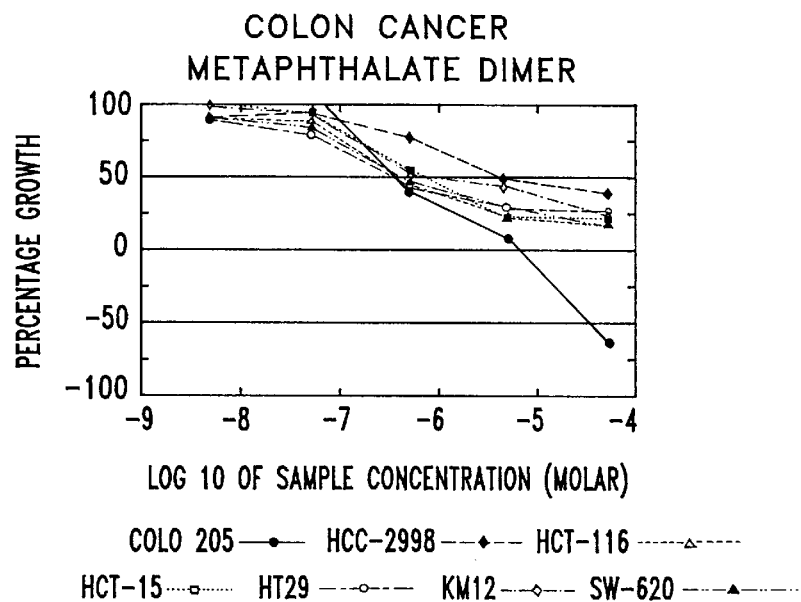

FIG. 12c depicts the dose response curves generated by exposing various colon cancer cell lines to various concentrations of the metaphthalate dimer of the present invention.

Figure 12D:
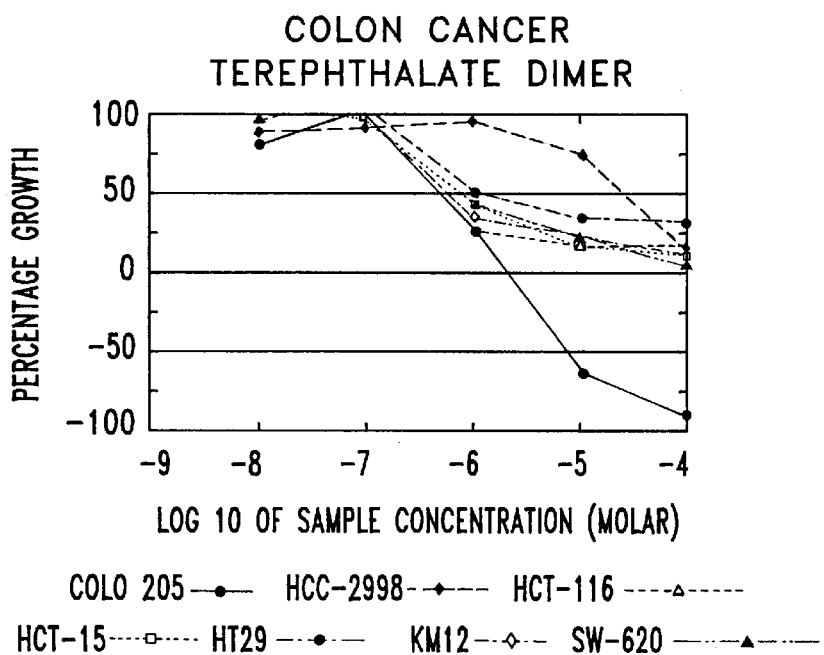

FIG. 12d depicts the dose response curves generated by exposing various colon cancer cell lines to various concentrations of the terephthalate dimer of the present invention.

Figure 12E:
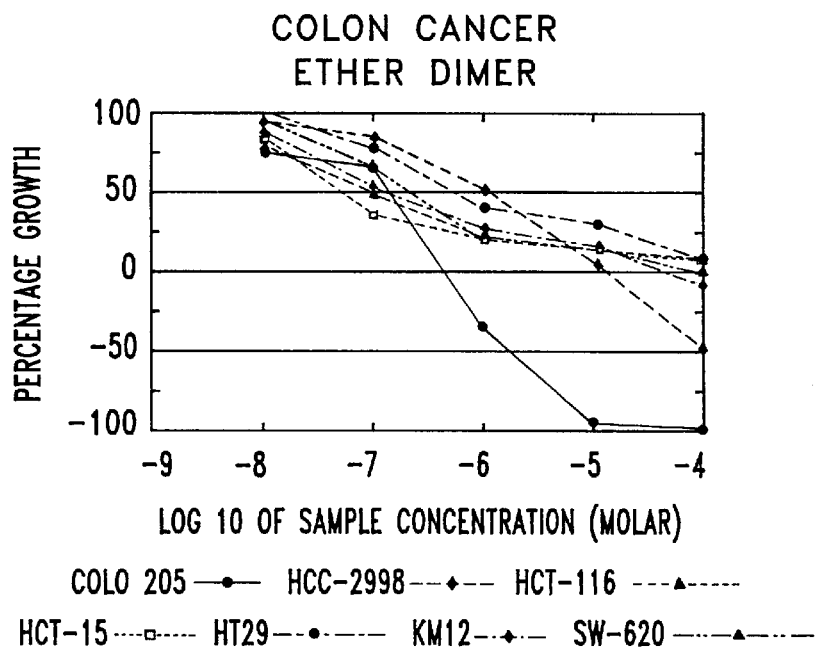

FIG. 12e depicts the dose response curves generated by exposing various colon cancer cell lines to various concentrations of the ether dimer of the present invention.

Figure 13A:
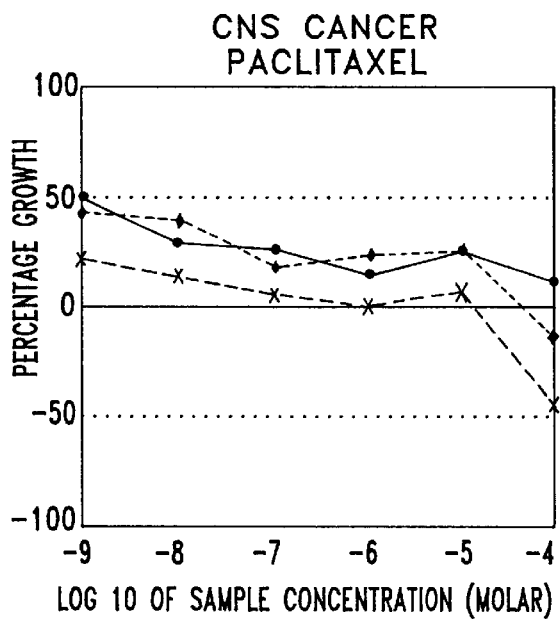

FIG. 13a depicts the dose response curves generated by exposing various CNS cancer cell lines to various concentrations of paclitaxel.

Figure 13B:
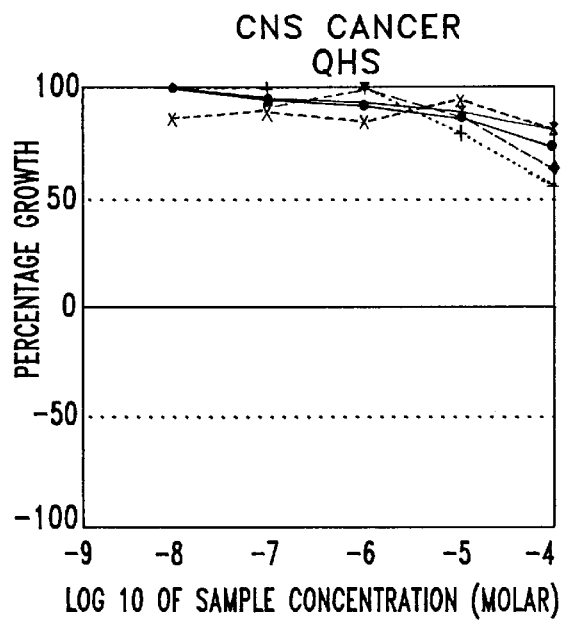

FIG. 13b depicts the dose response curves generated by exposing various CNS cancer cell lines to various concentrations of QHS.

Figure 13C:
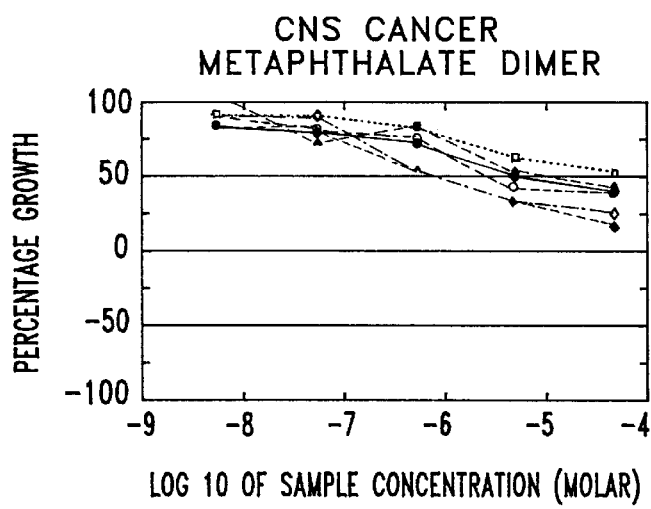

FIG. 13c depicts the dose response curves generated by exposing various CNS cancer cell lines to various concentrations of the metaphthalate dimer of the present invention.

Figure 13D:
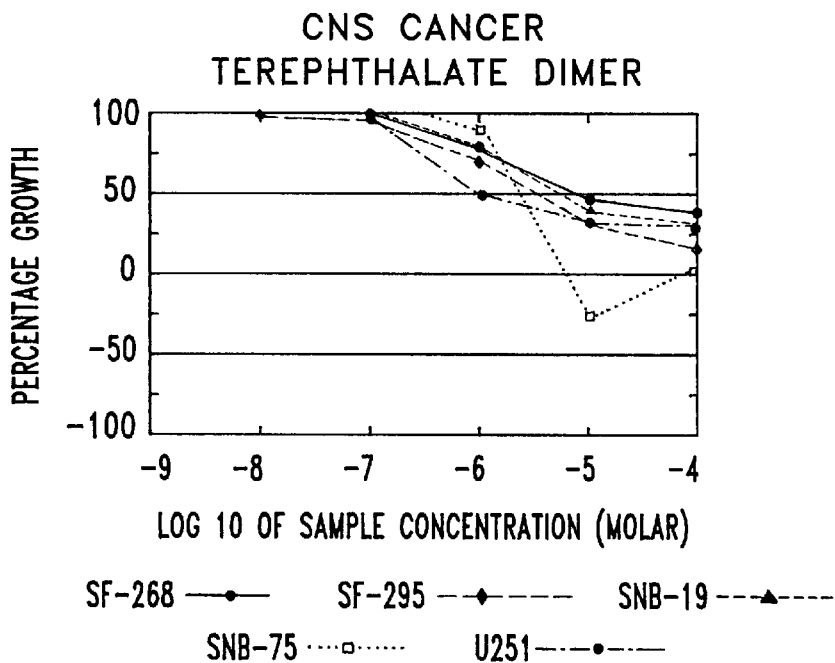

FIG. 13d depicts the dose response curves generated by exposing various CNS cancer cell lines to various concentrations of the terephthalate dimer of the present invention.

Figure 13E:
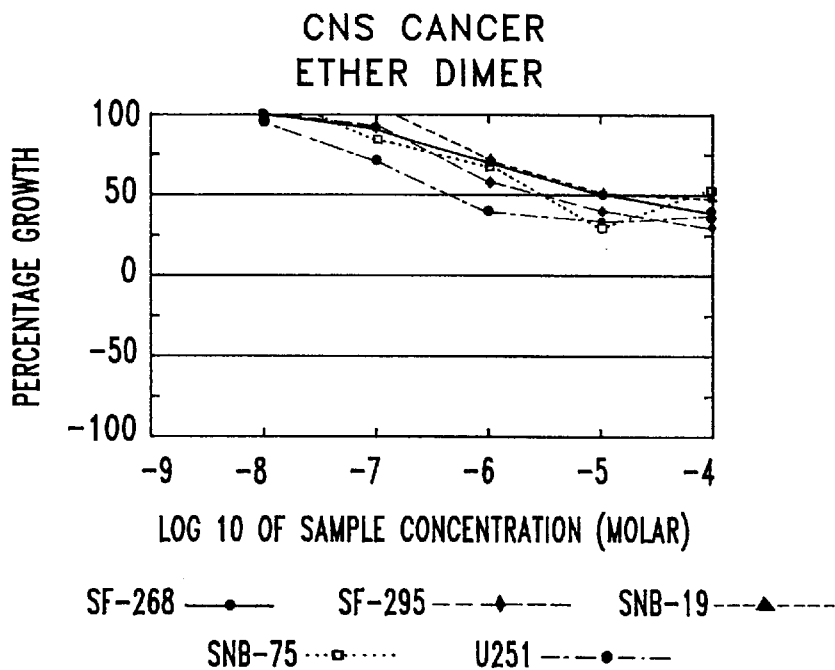

FIG. 13e depicts the dose response curves generated by exposing various CNS cancer cell lines to various concentrations of the ether dimer of the present invention.

FIG. 14a depicts the dose response curves generated by exposing various melanoma cancer cell lines to various concentrations of paclitaxel.

FIG. 14b depicts the dose response curves generated by exposing various melanoma cancer cell lines to various concentrations of QHS.

FIG. 14c depicts the dose response curves generated by exposing various melanoma cancer cell lines to various concentrations of the metaphthalate dimer of the present invention.

Figure 14D:
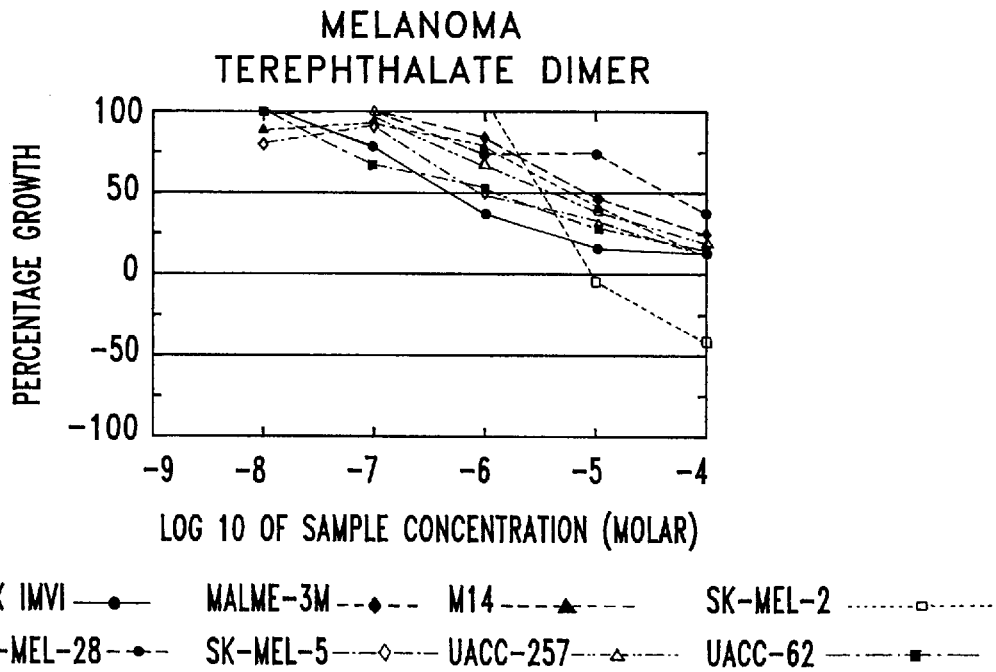

FIG. 14d depicts the dose response curves generated by exposing various melanoma cancer cell lines to various concentrations of the terephthalate dimer of the present invention.

Figure 14E:
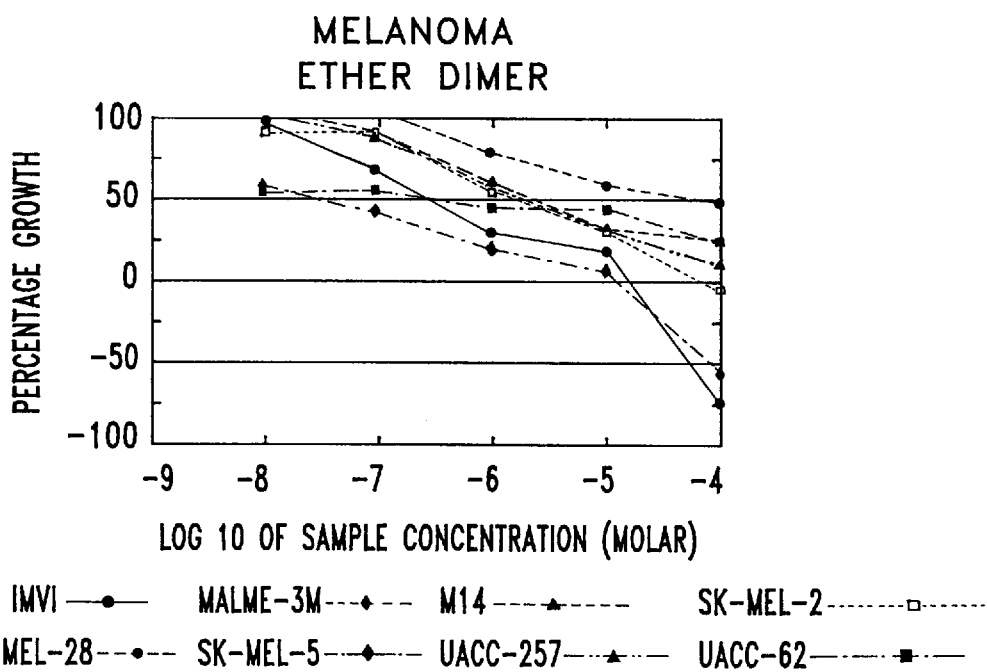

FIG. 14e depicts the dose response curves generated by exposing various melanoma cancer cell lines to various concentrations of the ether dimer of the present invention.

FIG. 15a depicts the dose response curves generated by exposing various ovarian cancer cell lines to various concentrations of paclitaxel.

FIG. 15b depicts the dose response curves generated by exposing various ovarian cancer cell lines to various concentrations of QHS.

FIG. 15c depicts the dose response curves generated by exposing various ovarian cancer cell lines to various concentrations of the metaphthalate dimer of the present invention.

Figure 15D:
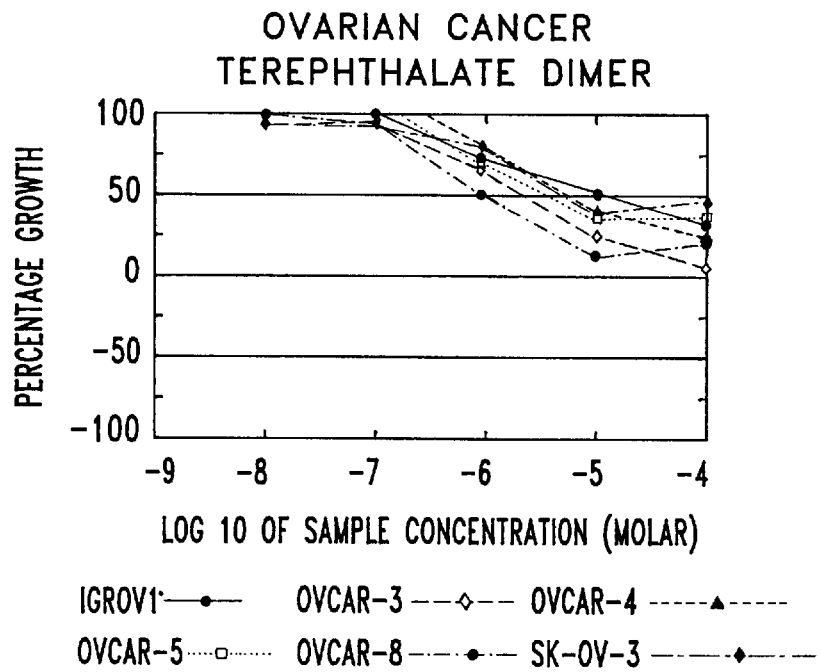

FIG. 15d depicts the dose response curves generated by exposing various ovarian cancer cell lines to various concentrations of the terephthalate dimer of the present invention.

Figure 15E:
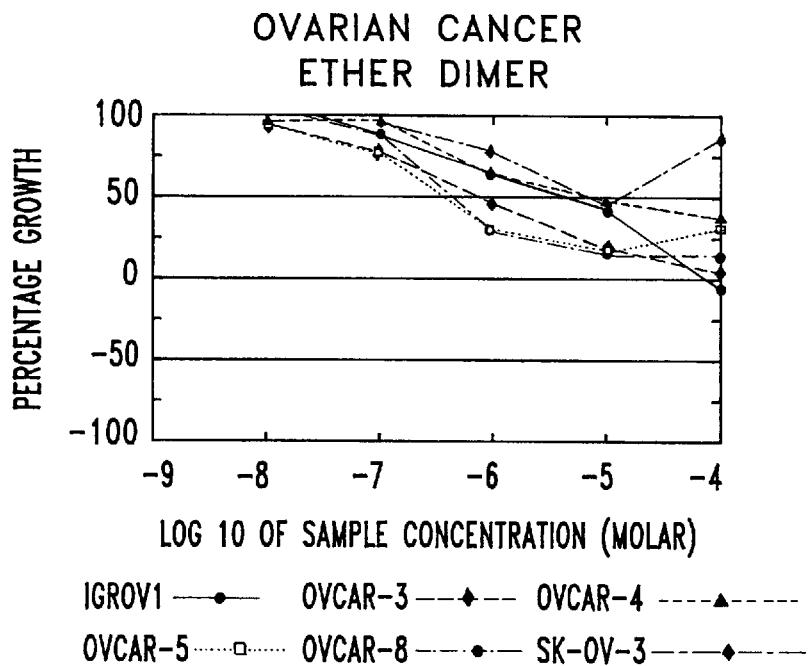

FIG. 15e depicts the dose response curves generated by exposing various ovarian cancer cell lines to various concentrations of the ether dimer of the present invention.

Figure 16A:
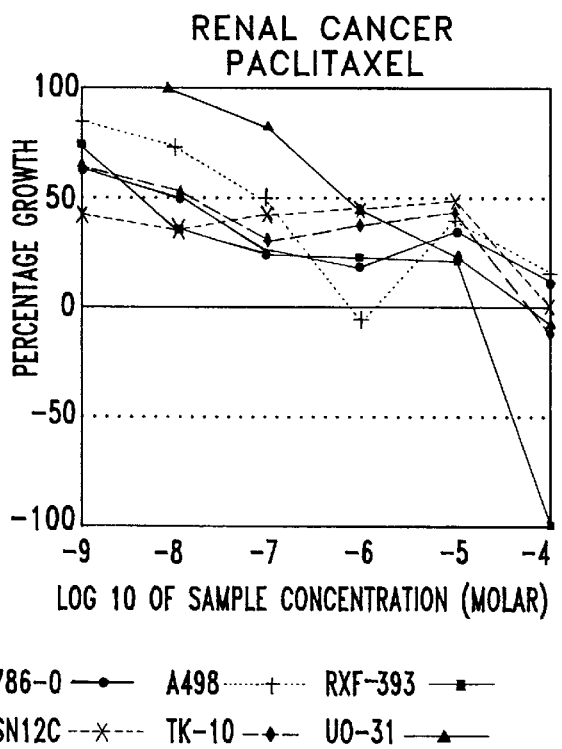

FIG. 16a depicts the dose response curves generated by exposing various renal cancer cell lines to various concentrations of paclitaxel.

Figure 16B:
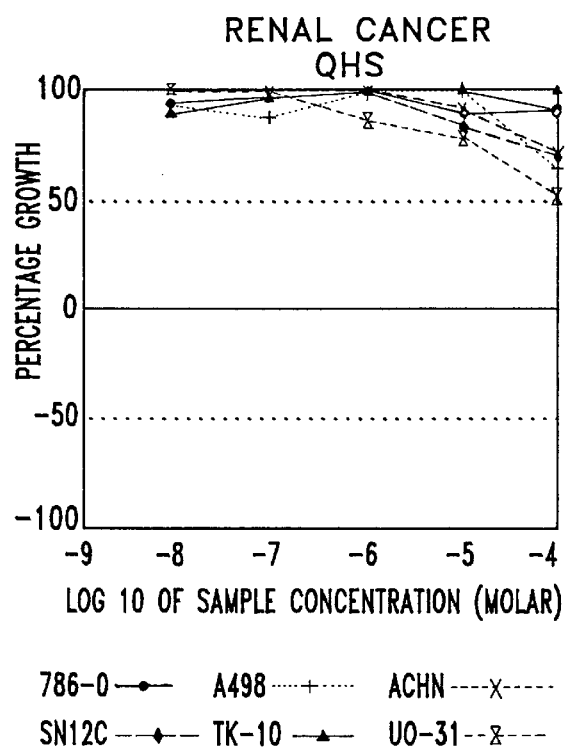

FIG. 16b depicts the dose response curves generated by exposing various renal cancer cell lines to various concentrations of QHS.

Figure 16C:
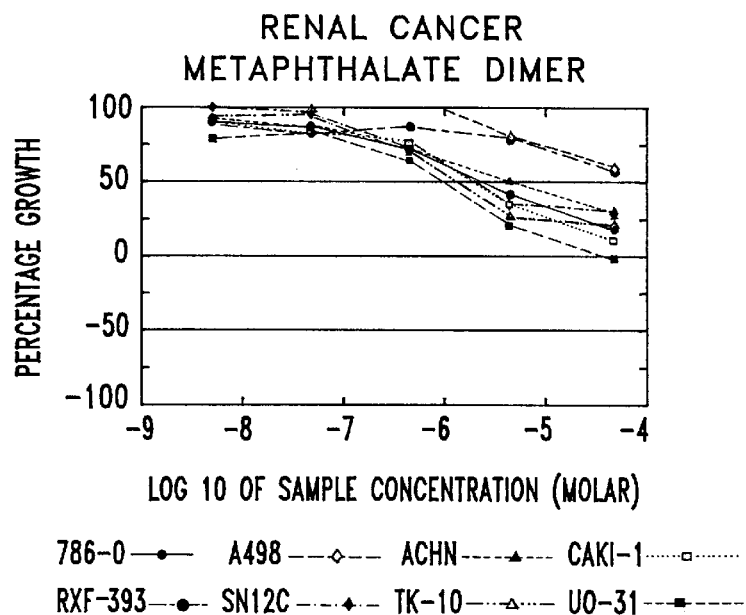

FIG. 16c depicts the dose response curves generated by exposing various renal cancer cell lines to various concentrations of the metaphthalate dimer of the present.

Figure 16D:
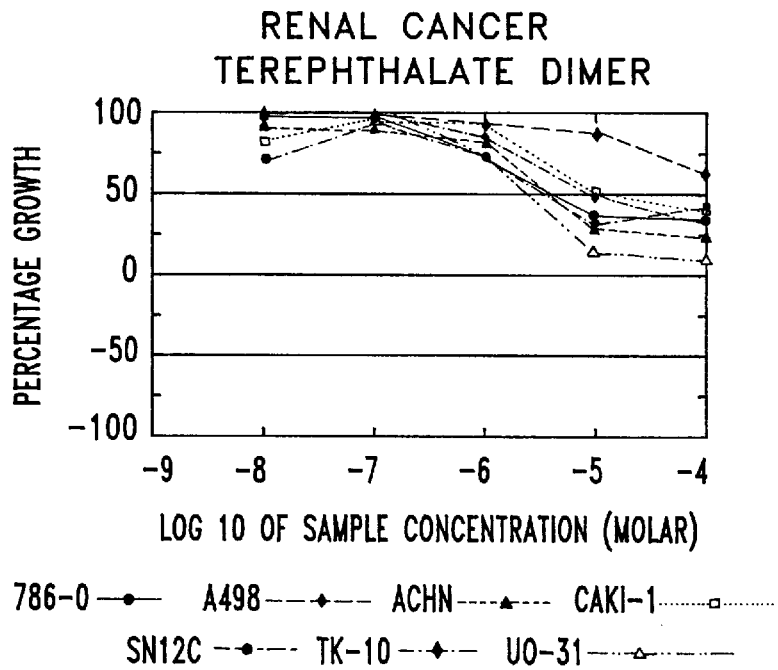

FIG. 16d depicts the dose response curves generated by exposing various renal cancer cell lines to various concentrations of the terephthalate dimer of the present.

Figure 16E:
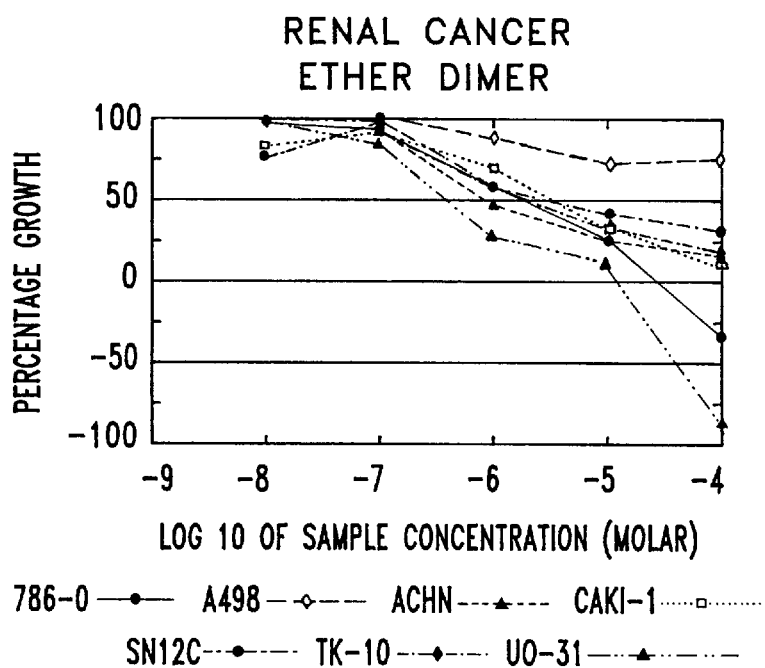

FIG. 16e depicts the dose response curves generated by exposing various renal cancer cell lines to various concentrations of the ether dimer of the present invention.

FIG. 17a depicts the dose response curves generated by exposing various prostate cancer cell lines to various concentrations of paclitaxel.

FIG. 17b depicts the dose response curves generated by exposing various prostate cancer cell lines to various concentrations of QHS.

FIG. 17c depicts the dose response curves generated by exposing various prostate cancer cell lines to various concentrations of the metaphthalate dimer of the present.

Figure 17D:
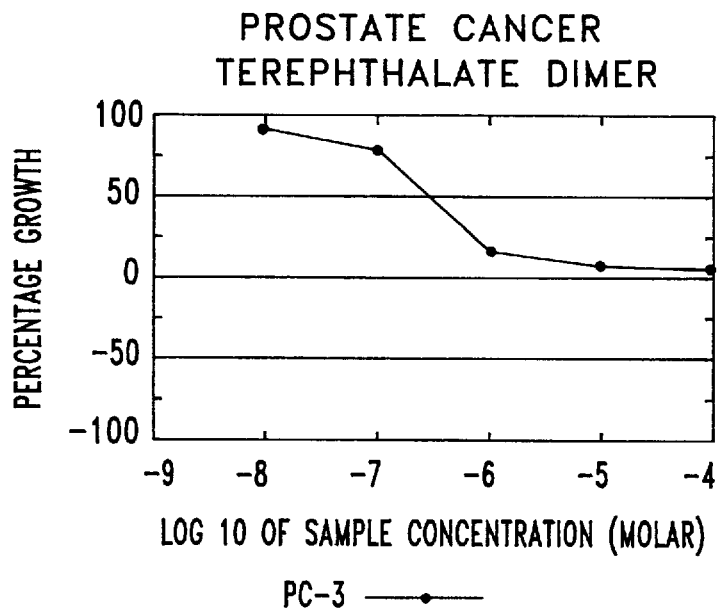

FIG. 17d depicts the dose response curves generated by exposing various prostate cancer cell lines to various concentrations of the terephthalate dimer of the present.

Figure 17E:
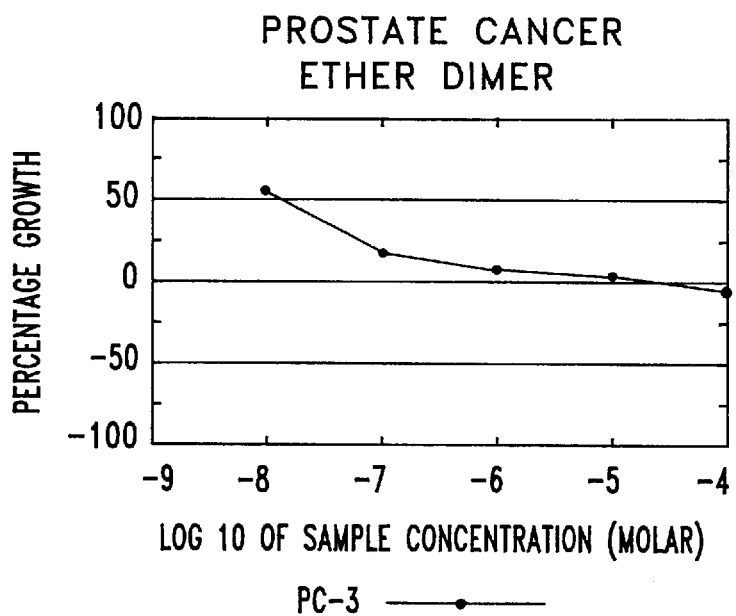

FIG. 17e depicts the dose response curves generated by exposing various prostate cancer cell lines to various concentrations of the ether dimer of the present invention.

FIG. 18a depicts the dose response curves generated by exposing various breast cancer cell lines to various concentrations of paclitaxel.

FIG. 18b depicts the dose response curves generated by exposing various breast cancer cell lines to various concentrations of QHS.

FIG. 18c depicts the dose response curves generated by exposing various breast cancer cell lines to various concentrations of the metaphthalate dimer of the present.

Figure 18D:
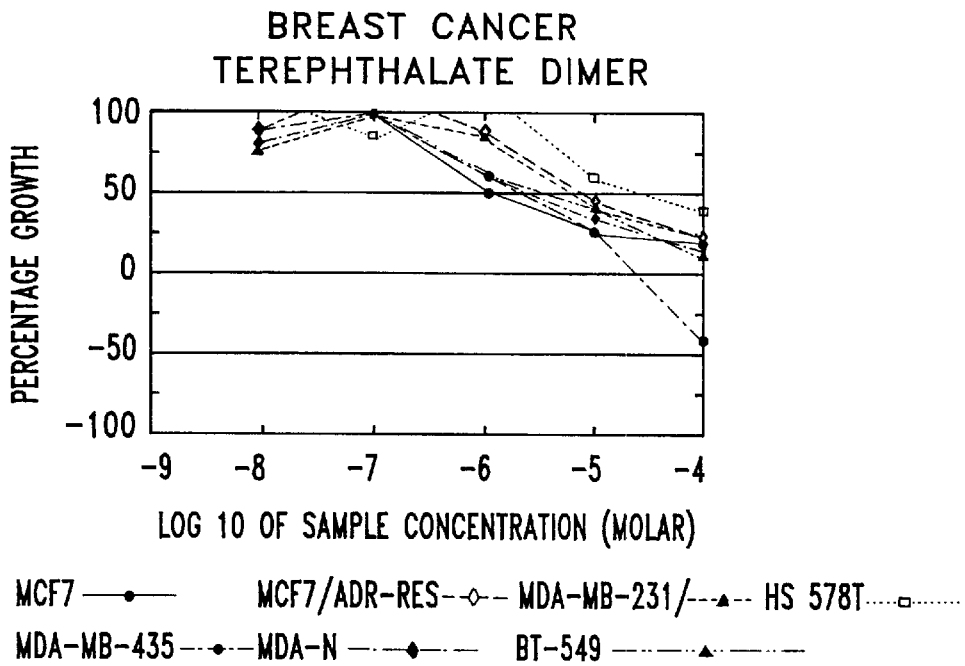

FIG. 18d depicts the dose response curves generated by exposing various breast cancer cell lines to various concentrations of the terephthalate dimer of the present.

Figure 18E:
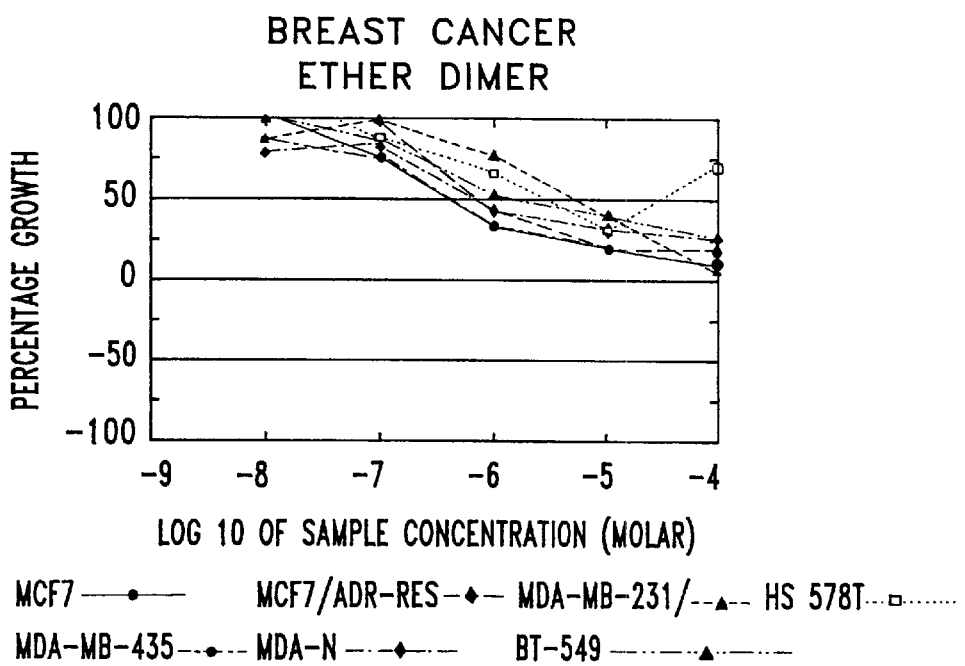

FIG. 18e depicts the dose response curves generated by exposing various breast cancer cell lines to various concentrations of the ether dimer of the present invention.

DETAILED DESCRIPTION OF THE PREFERRED EMBODIMENT

The present invention provides a novel class of 1,2,4-trioxane dimers of formula V:

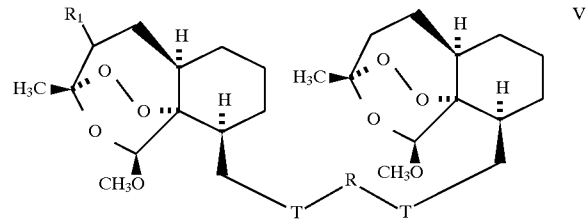

when T is $CH_2O$ and R, being attached to the oxygen is a linker such as an arylene, hetero-arylene, lower alkylene, lower alkenylene, a bivalent phosphate species, sulfur, oxygen, —$(CH_2CH_2O)_n$— wherein n is 1–20, —$CH_2CH_2$—$(XCH_2CH_2)_n$— where X is O, S or NY where Y is H (hydrogen) or alkyl and n is 0–20, or R is —W—Z—W— where W is a bivalent ester, carbamate or carbonate species and Z is arylene, polyethylene glycol (PEG), hetero-arylene, lower alkylene, or lower alkenylene and $R_1$ is hydrogen, a methyl group, chloromethylphenyl ($PhCH_2Cl$), dichlorophenyl ($PhCl_2$) or a benzyl group ($PhCH_2$) or in the alternative when T is $CH_2$, R is oxygen and $R_1$ is hydrogen, a methyl group, chloromethylphenyl ($PhCH_2Cl$), dichlorophenyl ($PhCl_2$) or a benzyl group ($PhCH_2$). References to "lower alkylene," "lower alkenylene," represent alkanes or alkenes of 1 to 20 carbon atoms. References to "halide" are compounds containing only carbon, hydrogen, and halogen, which fall into one of three general categories: Alkyl halides, aryl halides (in which a halogen is bonded to a carbon of an aromatic ring), and vinylic halides (in which a halogen is bonded to a double-bonded carbon). Within these general categories of halides are specific halides, such as, allylic halides and benzylic halides. An atom or group that is attached to the carbon atom adjacent to one of the sp² carbon atoms is said to be in the allylic position or the benzylic position, respectively. The isomers of the invention include the αα, αβ, and ββ configurations.

Examples of aryl substituents include, but are not limited to, phenol, and biphenol. Typical alkanes include, but not limited to, methane, ethane, propane, and butane. Examples of halides include, but are not limited to, 2-chlorobutane, 4-chloro-2-pentene, and 1-bromo-4-methyl-1-phenyl pentane.

The synthesis of a compound of structure V can be accomplished by a wide variety of methods. Preferably, the trioxane dimers of the present invention are synthesized in one chemical operation with the corresponding trioxane alcohol as shown schematically in Table 1 below:

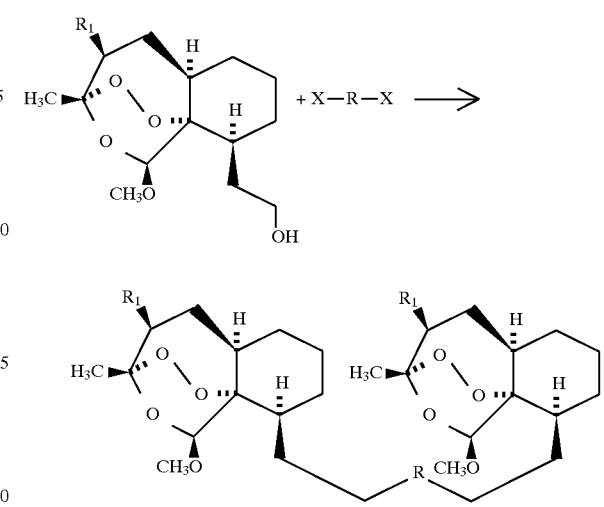

TABLE I

| Compound No. | R₁ | X | R | |
|---|---|---|---|---|
| 6 | H | Cl | —O— | |
| 7 | Me | Cl | —O— | |
| 8 | PhCl₂ | Cl | —O— | |
| 9 | H | Cl | phthalate (1,2-benzenedicarboxylate) | ortho |
| 10 | H | Cl | isophthalate (1,3-benzenedicarboxylate) | (meta) |
| 11 | H | Cl | terephthalate (1,4-benzenedicarboxylate) | (para) |
| 12 | H | Cl | 2,6-naphthalenediyl-bis(carbonyl) | |
| 13 | H | Cl | 2,6-pyridinedicarboxylate | |

TABLE I-continued

| Compound No. | R₁ | X | R | |
|---|---|---|---|---|
| 14 | H | Cl | −O−C(=O)−CH₂−CH₂−C(=O)−O− | |
| 15 | H | Cl | −O−C(=O)−(CH₂)₃−C(=O)−O− | |
| 16 | H | Cl | −O−C(=O)−(CH₂)₄−C(=O)−O− | |
| 17 | H | Cl | 1,3-cyclohexane dicarboxylate | 1,3-cis |
| 18 | H | Cl | 1,3-cyclohexane dicarboxylate | 1,3-trans |
| 19 | H | Cl | norbornene dicarboxylate | |
| 20 | H | Cl | −O−P(=O)(OPh)−O− | |
| 21 | H | Cl | −O−P(=O)(OCH₃)−O− | |
| 22 | H | Cl | −O−P(=O)(CH₃)−O− | |
| 23 | H | Cl | −O−C(=O)−CH₂−O−CH₂−CH₂−O−CH₂−CH₂−O−CH₂−C(=O)−O− | |

Compound 24 can also be synthesized in one chemical operation as shown schematically below and discussed in detail in Example 19 below:

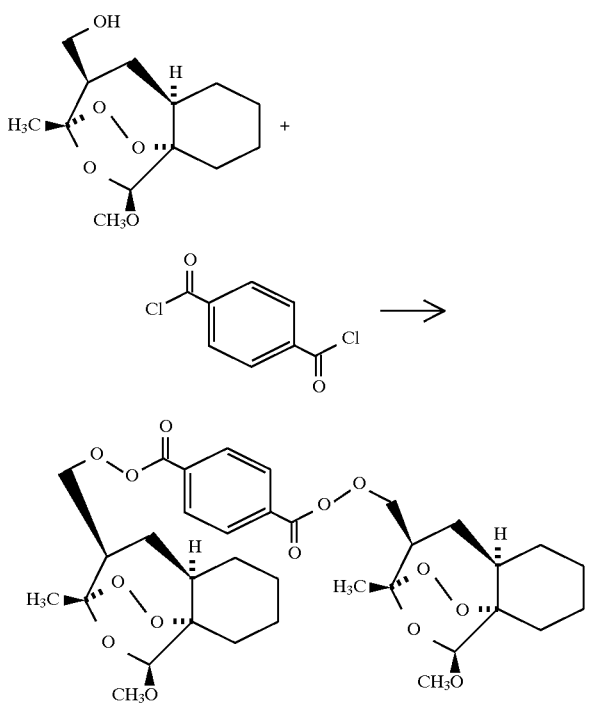

To determine the inhibitory effect of the trioxane dimers of the present invention on cell proliferation, screening assays were performed on a murine keratinocyte cell line PE. Cell line PE was chosen for its particular sensitivity to the induction of ornithine decarboxylase (ODC) activity by the extensively characterized tumor promoter TPA, cell line PE was derived from a papilloma-induced in female SEN-CAR mice by a standard skin initiation/promotion protocol, see Yupsa, S. H., et al., *Carcinogenesis,* 7:949–958 (1986). PE cell culture medium consisted of Eagle's minimal essential medium without calcium chloride (Whittaker Bioproducts, Walkersville, Ma.) supplemented with 8% chelexed fetal calf serum and 1% antibiotic-antimycotic (Gibco BRL) and the addition of $CaCl_2$ to 0.05 mM $Ca^{++}$.

MTT [3-(4,5-dimethylthiazol-2-yl)-2,5-diphenyltetraxolium bromide] was purchased from Sigma Chemical Co. (St. Louis, Mo.), and TPA was supplied by L. C. Services (Woburn, Ma.). L-[$^{14}$C]ornithine (56 μCi/mol) was from Amersham/Searle Corp. (Arlington Heights, Ill.). Chemical solvents used in all assays of biological activity were of the highest grade commercially available.

Growth Inhibition. Growth curves, shown in FIGS. 1–6, for PE cells treated with calcitriol and the trioxane dimers were generated by assay for the reduction of the tetrazolium-based compound MTT, see Charmichael, et al., *Cancer Res.,* 47:936–942 (1987). A mitochondrial dehydrogenase reduces MTT to a blue formazan product with an absorbance maximum of 505 nm in DMSO; the number of viable cells can thus be determined spectrophotometrically. PE cells were seeded at a density of 5,000 cells/well in 50 μL of medium into 96-well microtiter plates. Twelve hours later, the medium was removed, and cells were treated with 100 μL of fresh medium into which the appropriate amount of calcitriol or analog dissolved in dimethyl sulfoxide (DMSO) had been added, with the concentration of DMSO held constant at 0.1%. The plates were fed once at 48 h, with the readdition of the vitamin $D_3$ analogs at this time. At 24-h intervals following the initial treatment of the cells with compounds, 0.1 mg (50 μL of a 2 mg/mL solution) of MTT was added to each well. After 4 h, the MTT was removed and DMSO added to dissolve the blue formazan dye. Using a microtiter plate reader, the $A_{505}$ was then determined and cell number calculated from blank-subtracted absorbance values. Results from the MTT assay for the inhibition of cell growth were independently confirmed by treating 100-$cm^2$ dishes of cells in an analogous manner for 96 h, whereupon the cells were harvested by trypsinization and counted. Further, the viability of the cells treated with calcitriol or trioxane dimers was determined to be identical to control cells at 96 h by trypan blue exclusion.

Inhibition of TPA-Induced ODC Activity. The 100-$cm^2$ dishes of PE cells were treated with calcitriol or analogs dissolved in DMSO by direct addition into the culture medium. Fifteen minutes later, the plates were treated with 100 ng/mL TPA dissolved in ethanol. For both additions, the solvent concentration was held constant at 0.1%, and control values represent the results from plates treated with these solvents. Three plates were used for each experimental group. Following incubation for 4 h after addition of TPA, the medium was removed and the dishes washed with ice cold phosphate-buffered saline (PBS). The excess PBS was then removed, and the dishes were rinsed with an ice cold solution of pyridoxal phosphate in PBS (50 μg/mL). The excess liquid was removed, and the dishes were frozen at −80° C. The dishes were scraped into Eppendorf tubes while still partially frozen and the cells further lysed by freeze-thawing for generation of the 12000 g cytosol. Cytosolic ODC activity was determined in triplicate by measuring the release of $^{14}CO_2$ from L-[$^{14}$C]-ornithine using an Eppendorf microvessel assay as described by Kozumb, W. J., et al., *Cancer Res.,* 43:2555–2559 (1983).

Antiproliferative activities, measured in vitro using murine keratinocytes as described previously, are shown in FIGS. 1–9. Note that some of these trioxane dimers, even at physiologically relevant 10–100 nanomolar concentrations, are as antiproliferative as calcitriol (1α, 25-dihydroxyvitamin $D_3$) that is the hormonally active form of vitamin D and that is used clinically as a drug to treat psoriasis, a skin disorder characterized by uncontrolled proliferation of cells. Of the trioxane ether dimers of the present invention 6–8, the 4-unsubstituted dimer 6 and 4β-methyl substituted dimer 7 are the most antiproliferative, consistent with the highest antimalarial activity of the 4β-methyl alcohol monomer, see FIG. 7. Of the aromatic carboxylate ester dimers 9–13, both the meta-phthalate dimer 10 and the terephthalate dimer 11 have high antiproliferative activity as shown in FIG. 1 and 7, respectively. meta-phthalate dimer 10 has the highly desireable practical characteristics of being a crystalline solid that is stable for prolonged periods at room temperature. Of the aliphatic carboxylate ester dimers 14–16, the glutarate diester 15 is the most active, see FIGS. 2 and 9. Neither phosphate dimers 20, and 21 nor phosphonate dimer 22 has significant antiproliferative activity. 4β-Hydroxymehtyl terephthalate dimer 24 has significant antiproliferative activity. The high activities of glutarate diester 15 and meta-phthalate diester 10, each with a 3-carbon linker group, mirror the high activity of a glutarate diester of dihydroartemisinin; also a pentamidine analog having a 3-carbon linker having a very strong DNA-binding affinity.

To determine the cytotoxicity of the trioxane dimers of the present invention, screening assays were performed by the National Cancer Institute using a 60 cell line panel; some of these activities are summarized in Tables II, III and IV (set out below). The screening assay is performed on 96-well microtitre plates. Relatively high initial inoculation densities are used, in order to permit measurement of "time-zero"

values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a nonroutine basis if appropriate solubility and/or prior biological information or other screening data so dictate. Duplicate wells are prepared for all concentrations, (concentration is often denoted by placing brackets around a number); "time-zero" and "no drug" controls are also provided for each test. The minimum amount of compound required for a one-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$M) is: molecular weight of compound× $10^{-4}$×0.04. After a 48 hour incubation (37° C.) with the test compound, the cells are fixed in situ to the bottoms of the microtitre wells by addition of 50 ul of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50, respectively:

$GI_{50}$ is the concentration for which the PG=+50. At this value the increase from time $t_{zero}$ in the number or mass of cells in the test well is only 50% as much as the corresponding increase in the control well during this period of the experiment, see Table II. A drug effect of this intensity is interpreted as primary growth inhibition.

TGI is the concentration for which PG=0. At this value the number or mass of cells in the well at the end of the experiment equals the number or mass of cells in the well at time $t_{zero}$, see Table III. A drug effect of this intensity is regarded as cytostasis.

$LC_{50}$ is the concentration for which the PG=−50. At this value, the number or mass of cells in the test well at the end of the experiment is half that at time $t_{zero}$, see Table IV. This is interpreted as cytotoxicity.

TABLE II

| | | $Log_{10}GI_{50}$ | | | |
| | | Trioxane Dimers | | | |
| Panel/ Cell Line | QHS | Metaphtalate Dimer | Terephtalate Dimer | Ether Dimer | Pac- litaxel |
| --- | --- | --- | --- | --- | --- |
| Leukemia | | | | | |
| CCRF-CEM | — | −7.15 | −6.57 | −6.27 | −11.61 |
| HL-60(TB) | −4.26 | −7.21 | −7.42 | −6.48 | −11.57 |
| K-562 | −4.33 | −6.79 | −6.57 | −6.75 | −10.83 |
| MOLT-4 | −4.73 | −7.68 | −6.67 | −6.27 | −11.07 |
| RPMI-8226 | >−4.00 | −6.97 | −6.33 | −6.69 | <−13.00 |
| SR | >−4.00 | <−8.30 | −6.38 | −7.19 | 8.34 |
| Non-Small Cell Lung Cancer | | | | | |
| A549/ATCC | −4.17 | −5.89 | −5.42 | −5.79 | — |
| EKVX | >−4.00 | −5.31 | −5.20 | −5.56 | — |
| HOP-62 | >−4.00 | −5.11 | −5.01 | −4.92 | −9.67 |
| HOP-92 | >−4.00 | −6.01 | −4.91 | −5.51 | — |
| NCI-H226 | >−4.00 | −5.64 | −5.26 | −5.36 | — |
| NCI-H23 | >−4.00 | −6.29 | −6.03 | −6.34 | — |
| NCI-H322M | — | >−4.30 | −4.69 | >−4.00 | −10.12 |
| NCI-H460 | >−4.00 | −5.76 | −6.02 | −6.23 | −12.16 |
| NCI-H522 | — | −6.13 | −5.66 | −6.13 | <−13.00 |
| Colon Cancer | | | | | |
| COLO 205 | >−4.00 | −6.45 | −6.31 | −6.85 | −11.07 |
| HCC-2998 | >−4.00 | −5.32 | −4.56 | −5.94 | −12.34 |
| HCT-116 | −4.00 | −6.43 | −6.30 | −6.98 | <−13.00 |
| HCT-15 | >−4.00 | −6.14 | −6.12 | −7.28 | −6.37 |
| HT29 | >−4.00 | −6.35 | −5.90 | −6.24 | <−13.00 |
| KM12 | >−4.00 | −5.97 | −6.24 | −6.85 | −11.43 |
| SW-620 | >−4.00 | −6.47 | −6.12 | −6.66 | −11.60 |
| CNS Cancer | | | | | |
| SF-268 | — | −5.36 | −5.14 | −5.07 | — |
| SF-295 | — | −5.01 | −5.49 | −5.61 | — |
| SF-539 | — | −6.11 | — | — | −11.09 |
| SNB-19 | >−4.00 | >−4.30 | −5.31 | −5.01 | −8.98 |
| SNB-75 | >−4.00 | −5.56 | −5.66 | — | — |
| U251 | >−4.00 | −6.09 | −6.02 | −6.35 | −11.29 |
| Melanoma | | | | | |
| LOX IMVI | — | −6.27 | −6.28 | −6.52 | −11.80 |
| MALME-3M | — | −5.56 | −5.03 | −5.69 | — |
| M14 | — | −5.08 | −5.20 | −5.59 | −11.73 |
| SK-MEL-2 | — | −5.47 | −5.47 | −5.86 | −9.53 |
| SK-MEL-28 | >−4.00 | −4.94 | −4.31 | −4.24 | — |
| SK-MEL-5 | −4.10 | −5.57 | −6.00 | −7.39 | — |
| UACC-257 | >−4.00 | −5.03 | −5.36 | −5.68 | −10.30 |
| UACC-62 | >−4.00 | −5.68 | −5.87 | −6.46 | −10.46 |
| Ovarian Cancer | | | | | |
| IGROVI | −4.31 | −5.34 | −4.95 | −5.37 | −8.61 |
| OVCAR-3 | — | −5.53 | −5.63 | −6.10 | −10.40 |
| OVCAR-4 | — | >−4.0 | −5.26 | −5.11 | −5.00 |
| OVCAR-5 | >−4.00 | −5.68 | −5.45 | −6.39 | −9.38 |
| OVCAR-8 | >−4.00 | −6.13 | −6.03 | −6.33 | −10.75 |
| SK-OV-3 | — | >4.30 | −5.28 | — | — |
| Renal Cancer | | | | | |
| 786-0 | >−4.00 | −5.57 | −5.41 | −5.65 | −8.01 |
| A498 | >−4.00 | >−4.30 | >−4.00 | >−4.00 | −7.14 |
| ACHN | >−4.00 | −5.85 | −5.42 | −5.99 | — |
| CAKI-1 | — | −5.66 | −4.99 | −5.44 | — |
| RXF 393 | −4.08 | >−4.30 | — | — | −8.32 |
| SN12C | −4.21 | −5.73 | −5.46 | −5.46 | −9.53 |
| TK-10 | >−4.00 | −5.39 | −5.06 | −5.60 | −7.89 |
| UO-31 | −4.06 | −5.96 | −5.63 | −6.37 | −6.09 |
| Prostate Cancer | | | | | |
| PC-3 | −4.17 | −7.09 | −6.51 | −7.85 | −10.85 |
| DU-145 | — | −4.53 | — | — | −9.38 |
| Breast Cancer | | | | | |
| MCF7 | >−4.00 | −5.92 | −5.86 | −6.37 | −11.69 |

TABLE II-continued

| | | Log$_{10}$GI$_{50}$ | | | |
| | | Trioxane Dimers | | | |
| Panel/Cell Line | QHS | Metaphtalate Dimer | Terephtalate Dimer | Ether Dimer | Paclitaxel |
|---|---|---|---|---|---|
| MCF7/ADR-RES | — | −5.36 | −5.11 | −6.13 | −8.48 |
| MDA-MB231/ATCC | −4.20 | −5.27 | −5.18 | −5.25 | −8.54 |
| HS 578T | >−4.00 | −6.07 | −4.55 | — | — |
| MDA-MB-435 | — | −5.93 | −5.69 | −6.38 | <−13.00 |
| MDA-N | >−4.00 | −5.97 | −5.56 | −6.19 | <−13.00 |
| BT-549 | −4.06 | −5.47 | −5.44 | −5.89 | −9.31 |
| T-47D | — | −6.76 | — | — | −9.81 |
| MG MID | — | −5.77 | −5.59 | −5.99 | — |
| Delta | −4.07 | 2.53 | 1.82 | 1.85 | −10.15 |
| Range | 0.73 | 4.00 | 3.42 | 3.85 | 8.00 |

TABLE III

| | | Log$_{10}$TGI | | | |
| | | Trioxane Dimers | | | |
| Panel/Cell Line | QHS | Metaphtalate Dimer | Terephtalate Dimer | Ether Dimer | Paclitaxel |
|---|---|---|---|---|---|
| Leukemia | | | | | |
| CCRF-CEM | — | −5.70 | −4.89 | −4.61 | >−4.00 |
| HL-60(TB) | −4.00 | −6.56 | −6.58 | −5.77 | −4.53 |
| K-562 | −4.00 | −5.35 | >−4.00 | >−4.00 | >−4.00 |
| MOLT-4 | −4.00 | −6.53 | −4.70 | >−4.00 | >−4.00 |
| RPMI-8226 | >−4.00 | −5.73 | −5.10 | −5.47 | >−4.00 |
| SR | >−4.00 | −7.49 | −5.17 | −5.93 | >−4.00 |
| Non-Small Cell Lung Cancer | | | | | |
| A549/ATCC | >−4.00 | >−4.30 | >−4.00 | >−4.00 | — |
| EKVX | >−4.00 | >−4.30 | >−4.00 | >−4.00 | — |
| HOP-62 | >−4.00 | >−4.30 | >−4.00 | >−4.00 | −4.80 |
| HOP-92 | >−4.00 | −4.64 | >−4.00 | −4.17 | — |
| NCI-H226 | >−4.00 | >−4.30 | >−4.00 | >−4.00 | — |
| NCI-H23 | >−4.00 | >−4.30 | −4.19 | >−4.00 | — |
| NCI-H322M | — | >−4.0 | >−4.00 | >−4.00 | −4.46 |
| NCI-H460 | >−4.00 | >−4.30 | >−4.00 | >−4.00 | −4.92 |
| NCI-H522 | — | >−4.30 | −4.45 | −4.76 | −11.20 |
| Colon Cancer | | | | | |
| COLO 205 | >−4.00 | −5.18 | −5.71 | −6.36 | — |
| HCC-2998 | >−4.00 | >−4.30 | >−4.00 | −4.90 | −4.77 |
| HCT-116 | >−4.00 | >−4.30 | >−4.00 | >−4.00 | −4.82 |
| HCT-15 | >−4.00 | >−4.30 | >−4.00 | >−4.00 | >−4.00 |
| HT29 | >−4.00 | >−4.30 | >−4.00 | >−4.00 | — |
| KM12 | >−4.00 | >−4.30 | >−4.00 | −4.28 | −4.36 |
| SW-620 | >−4.00 | >−4.30 | >−4.00 | >−4.00 | >−4.00 |
| CNS Cancer | | | | | |
| SF-268 | — | >−4.30 | >−4.00 | >−4.00 | — |
| SF-295 | — | >−4.30 | >−4.00 | >−4.00 | — |
| SF-539 | — | >−4.30 | — | — | — |
| SNB-19 | >−4.00 | >−4.30 | >−4.00 | >−4.00 | >−4.00 |
| SNB-75 | >−4.00 | >−4.30 | — | >−4.00 | — |
| U251 | >−4.00 | >−4.30 | >−4.00 | >−4.00 | −4.32 |
| Melanoma | | | | | |
| LOX IMVI | — | >−4.30 | >−4.00 | −4.83 | −4.65 |
| MALME-3M | −4.06 | >−4.30 | >−4.00 | >−4.00 | −4.46 |
| M14 | >−4.00 | >−4.30 | >−4.00 | >−4.00 | −4.62 |
| SK-MEL-2 | >−4.00 | >−4.30 | −5.04 | −4.13 | — |
| SK-MEL-28 | >−4.00 | >−4.30 | >−4.00 | >−4.00 | — |
| SK-MEL-5 | >−4.00 | >−4.30 | >−4.00 | −4.90 | — |
| UACC-257 | >−4.00 | >−4.30 | >−4.00 | >−4.00 | −4.52 |
| UACC-62 | >−4.00 | >−4.30 | >−4.00 | >−4.00 | −4.71 |

TABLE III-continued

| | | Log$_{10}$TGI | | | |
| | | Trioxane Dimers | | | |
| Panel/Cell Line | QHS | Metaphtalate Dimer | Terephtalate Dimer | Ether Dimer | Paclitaxel |
|---|---|---|---|---|---|
| Ovarian Cancer | | | | | |
| IGROVI | >−4.00 | −4.42 | >−4.00 | −4.13 | −4.19 |
| OVCAR-3 | — | >−4.30 | >−4.00 | >−4.00 | −4.55 |
| OVCAR-4 | — | >−4.30 | >−4.00 | >−4.00 | −4.19 |
| OVCAR-5 | >−4.00 | >−4.30 | >−4.00 | >−4.00 | −4.92 |
| OVCAR-8 | >−4.00 | >−4.30 | >−4.00 | >−4.00 | — |
| SK-OV-3 | — | >−4.30 | >−4.00 | >−4.00 | — |
| Renal Cancer | | | | | |
| 786-0 | >−4.00 | >−4.30 | >−4.00 | −4.53 | >−4.00 |
| A498 | >−4.00 | >−4.30 | >−4.00 | >−4.00 | — |
| ACHN | >−4.00 | >−4.30 | >−4.00 | >−4.00 | −4.90 |
| CAKI-1 | — | >−4.30 | >−4.00 | >−4.00 | −4.04 |
| RXF 393 | >−4.00 | >−4.30 | — | — | >−4.00 |
| SN12C | >−4.00 | >−4.30 | >−4.00 | >−4.00 | −4.29 |
| TK-10 | >−4.00 | >−4.30 | >−4.00 | −4.88 | — |
| UO-31 | −4.00 | >−4.30 | >−4.00 | — | — |
| Prostate Cancer | | | | | |
| PC-3 | >−4.00 | >−4.30 | >−4.00 | −4.75 | >−4.00 |
| DU-145 | — | >−4.30 | — | — | >−4.00 |
| Breast Cancer | | | | | |
| MCF7 | >−4.00 | >−4.30 | >−4.00 | >−4.00 | −4.05 |
| MCF7/ADR-RES | — | >−4.0 | >−4.00 | >−4.00 | >−4.00 |
| MDA-MB231/ATCC | −4.00 | >−4.30 | >−4.00 | >−4.00 | −4.84 |
| HS 578T | >−4.00 | >−4.30 | >−4.00 | >−4.00 | — |
| MDA-MB-435 | — | >−4.30 | −4.63 | >−4.00 | — |
| MDA-N | >−4.00 | >−4.30 | >−4.00 | >−4.00 | — |
| BT-549 | −4.00 | >−4.30 | >−4.00 | >−4.00 | −6.32 |
| T-47D | >−4.00 | >−4.30 | — | — | −4.05 |
| MG MID | — | −4.52 | −4.19 | −4.26 | — |
| Delta | −4.00 | 2.97 | 2.39 | 2.10 | −4.54 |
| Range | 0.06 | 3.19 | 2.58 | 2.36 | 7.20 |

*NCI indicates these values are not relevant

TABLE IV

| | | Log$_{10}$LC$_{50}$ | | | |
| | | Trioxane Dimers | | | |
| Panel/Cell Line | QHS | Metaphtalate Dimer | Terephtalate Dimer | Ether Dimer | Paclitaxel |
|---|---|---|---|---|---|
| Leukemia | | | | | |
| CCRF-CEM | — | >−4.30 | −4.05 | >−4.00 | >−4.00 |
| HL-60(TB) | >−4.00 | >−4.30 | −5.26 | >−4.00 | >−4.53 |
| K-562 | >−4.00 | >−4.30 | >−4.00 | >−4.00 | >−4.00 |
| MOLT-4 | >−4.00 | >−4.30 | >−4.00 | >−4.00 | >−4.00 |
| RPMI-8226 | >−4.00 | >−4.30 | >−4.00 | >−4.00 | >−4.00 |
| SR | >−4.00 | >−4.30 | >−4.00 | >−4.00 | >−4.00 |
| Non-Small Cell Lung Cancer | | | | | |
| A549/ATCC | >−4.00 | >−4.30 | >−4.00 | >−4.00 | — |
| EKVX | >−4.00 | >−4.30 | >−4.00 | >−4.00 | — |
| HOP-62 | >−4.00 | >−4.30 | >−4.00 | >−4.00 | −4.10 |
| HOP-92 | >−4.00 | >−4.30 | >−4.00 | >−4.00 | — |
| NCI-H226 | >−4.00 | >−4.30 | >−4.00 | >−4.00 | — |
| NCI-H23 | >−4.00 | >−4.30 | >−4.00 | >−4.00 | — |
| NCI-H322M | — | >−4.30 | >−4.00 | >−4.00 | >−4.00 |
| NCI-H460 | >−4.00 | >−4.30 | >−4.00 | >−4.00 | >−4.00 |
| NCI-H522 | — | >−4.30 | >−4.00 | >−4.00 | >−4.00 |

TABLE IV-continued

| | | $Log_{10}LC_{50}$ | | | |
| | | Trioxane Dimers | | | |
| Panel/ Cell Line | QHS | Metaphtalate Dimer | Terephtalate Dimer | Ether Dimer | Paclitaxel |
|---|---|---|---|---|---|
| Colon Cancer | | | | | |
| COLO 205 | >−4.00 | −4.48 | −5.17 | −5.77 | >−4.41 |
| HCC-2998 | >−4.00 | >−4.30 | >−4.00 | −4.04 | −4.26 |
| HCT-116 | >−4.00 | >−4.30 | >−4.00 | >−4.00 | >−4.00 |
| HCT-15 | >−4.00 | >−4.30 | >−4.00 | >−4.00 | >−4.00 |
| HT29 | >−4.00 | >−4.30 | >−4.00 | >−4.00 | −4.39 |
| KM12 | >−4.00 | >−4.30 | >−4.00 | >−4.00 | >−4.00 |
| SW-620 | >−4.00 | >−4.30 | >−4.00 | >−4.00 | >−4.00 |
| CNS Cancer | | | | | |
| SF-268 | — | >−4.30 | >−4.00 | >−4.00 | — |
| SF-295 | — | >−4.30 | >−4.00 | >−4.00 | — |
| SF-539 | — | >−4.30 | >−4.00 | — | >−4.00 |
| SNB-19 | >−4.00 | >−4.30 | >−4.00 | >−4.00 | >−4.00 |
| SNB-75 | >−4.00 | >−4.30 | >−4.00 | >−4.00 | — |
| U251 | >−4.00 | >−4.30 | >−4.00 | >−4.00 | −4.15 |
| Melanoma | | | | | |
| LOX IMVI | — | >−4.30 | >−4.00 | −4.33 | >−4.15 |
| MALME-3M | >−4.00 | >−4.30 | >−4.00 | >−4.00 | −4.11 |
| M14 | >−4.00 | >−4.30 | >−4.00 | >−4.00 | −4.13 |
| SK-MEL-2 | >−4.00 | >−4.30 | >−4.00 | >−4.00 | >−4.00 |
| SK-MEL-28 | >−4.00 | >−4.30 | >−4.00 | >−4.00 | — |
| SK-MEL-5 | >−4.00 | >−4.30 | >−4.00 | −4.15 | — |
| UACC-257 | >−4.00 | >−4.30 | >−4.00 | >−4.00 | −4.03 |
| UACC-62 | >−4.00 | >−4.30 | >−4.00 | >−4.00 | −4.19 |
| Ovarian Cancer | | | | | |
| IGROVI | >−4.00 | >−4.30 | >−4.00 | >−4.00 | >−4.00 |
| OVCAR-3 | — | >−4.30 | >−4.00 | >−4.00 | >−4.00 |
| OVCAR-4 | — | >−4.30 | >−4.00 | >−4.00 | >−4.00 |
| OVCAR-5 | >−4.00 | >−4.30 | >−4.00 | >−4.00 | >−4.00 |
| OVCAR-8 | >−4.00 | >−4.30 | >−4.00 | >−4.00 | >−4.00 |
| SK-OV-3 | — | >−4.30 | >−4.00 | >−4.00 | — |
| Renal Cancer | | | | | |
| 786-0 | >−4.00 | >−4.30 | >−4.00 | >−4.00 | >−4.00 |
| A498 | >−4.00 | >−4.30 | >−4.00 | >−4.00 | −4.13 |
| ACHN | >−4.00 | >−4.30 | >−4.00 | >−4.00 | −4.45 |
| CAKI-1 | — | >−4.30 | >−4.00 | >−4.00 | >−4.00 |
| RXF 393 | >−4.00 | >−4.30 | — | — | >−4.00 |
| SN12C | >−4.00 | >−4.30 | >−4.00 | >−4.00 | >−4.00 |
| TK-10 | >−4.00 | >−4.30 | >−4.00 | >−4.00 | — |
| UO-31 | >−4.00 | >−4.30 | >−4.00 | −4.38 | — |
| Prostate Cancer | | | | | |
| PC-3 | >−4.00 | >−4.30 | >−4.00 | −4.00 | >−4.00 |
| DU-145 | — | >−4.30 | — | — | >−4.00 |
| Breast Cancer | | | | | |
| MCF7 | >−4.00 | >−4.30 | >−4.00 | >−4.00 | >−4.00 |
| MCF7/ADR-RES | — | >−4.30 | >−4.00 | >−4.00 | >−4.00 |
| MDA-MB231/ATCC | >−4.00 | >−4.30 | >−4.00 | >−4.00 | −4.29 |
| HS 578T | >−4.00 | >−4.30 | >−4.00 | >−4.00 | — |
| MDA-MB-435 | — | >−4.30 | >−4.00 | >−4.00 | — |
| MDA-N | — | >−4.30 | >−4.00 | >−4.00 | — |
| BT-549 | >−4.00 | >−4.30 | >−4.00 | >−4.00 | >−4.00 |
| T-47D | >−4.00 | >−4.30 | — | — | >−4.00 |
| MG MID | — | −4.30 | −4.04 | −4.05 | — |
| Delta | −4.00 | 0.17 | 1.21 | 1.72 | −4.06 |
| Range | 0.00 | 0.18 | 1.26 | 1.77 | 0.45 |

The trioxane dimers of the present invention in most instances are as potent and in some instances more potent than paclitaxel. The data in Tables II, III and IV are graphically represented in FIGS. 10a, b, c, d and e through FIGS. 18e. Dose response curves, shown in the above mentioned Figures, are obtained by exposing various cancer cell lines to compounds having a known concentration ($[log_{10}$ M]), as discussed in detail above, and then plotting the percentage growth of each cell line for each concentration. The drug concentration limits that are tested are between $10^{-4}$ or −4.00M and $10^{-8}$ or −8.00M. The −4.00M value being the high concentration and the −8.00M value being the low concentration. Percentage growth is determined by dividing the number or mass of cells in the test well by the number or mass of cells in a control well. Referring to the leukemia cell line MOLT-4 in FIGS. 10a, 10b, 10c, 10d and 10e the first comparison that is made between QHS, paclitaxel the trioxane dimers of the present invention (metaphtalate dimer, terephthalate dimer and ether dimer) are the drug concentrations which are necessary to inhibit growth, graphically represented in FIGS. 10a, 10b, 10c, 10d and 10e as the concentration necessary to achieve the percentage growth value of +50. As discussed previously, the five drug dilutions routinely tested range from $10^{-4}$ to $10^{-8}$ molar. Therefore, concentrations less than or greater than $10^{-8}$ and $10^{-4}$ molar, respectively, that are required to achieve a desired result are not determined. Referring now to FIG. 7a, some concentration of paclitaxel that is less than $10^{-8}$M is necessary to achieve primary growth inhibition; in fact the lower concentrations have been determined for this drug and the concentration at which primary growth inhibition occurs using paclitaxel is at −11.07 molar. FIG. 10b indicates that some concentration of QHS that is greater than $10^{-4}$ molar is necessary to achieve primary growth inhibition. Referring to the metaphthalate dimer, terephthalate dimer and ether dimer dose response curves in FIGS. 10c, 10d and 10e, respectively, the leukemia cell line MOLT-4 displays primary growth inhibition at drug concentrations that are less than $10^{-7}$, $10^{-6}$ and $10^{-6}$, respectively. The drug concentration at which QHS is considered cytostasis, i.e. percentage growth is equal to 0, is at a concentration of approximately −4.00 molar. The metaphthalate dimers, terephthalate dimers and ether dimers reach cytostasis at drug concentrations of −5.80M, 6.20M, 4.50M and 4.50M, respectively, while the paclitaxel concentration necessary to achieve cytostasis is some value greater than −4.00 molar. Cytotoxicity, i.e., the concentration for which the percentage growth is equal to −50, occurs at a concentration greater than −4.00M for paclitaxel and QHS, −4.05M for the metaphthalate dimer, and a concentration greater than −400.M for both the dimer and either dimer.

The potency of trioxane dimers of the present invention as compared to QHS and paclitaxel varies from cell line to cell line. However, the mean values for each drug are presented at the end of Tables II, III and IV and trioxane dimers of the present invention were more potent than QHS and equivalent to and in many instances greater than that for paclitaxel.

The DHQHS condensation by-product disclosed by M. Cao et al., and tested by D. L. Klayman and H. J. Woerdenbag, discussed previously, was approximately twenty-two times more potent at causing 50% growth inhibition in one cell line than QHS. With respect to the drug concentrations causing 50% growth inhibition, the trioxane dimers were at least 100 times more potent than QHS. When interpreting the mean values, it is important to take into consideration that drug concentrations less than $10^{-8}$M and greater then $10^{-4}$M were not collected, and this factor is reflected in the range.

For a further comparison on the effects of the trioxane dimers of the present invention on various cancer cell lines versus the effects of QHS and paclitaxel on the same cell lines see FIGS. 11a, b, c, d and e for non-small cell lung cancer cell lines, FIGS. 12a, b, c, d and e for colon cancer cell lines, FIGS. 13a, b, c, d and e for CNS cancer cell lines, FIGS. 14a, b, c, d and e for melanoma cancer cell lines, FIGS. 15a, b, c, d and e for ovarian cancer cell lines FIGS. 16a, b, c, d and e for renal cancer cell lines, FIGS. 17a, b, c, d and e for prostate cancer cell lines and FIGS. 18a, b, c, d and e for breast cancer cell lines.

The invention is further illustrated by the following non-limited examples. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art.

Unless otherwise noted: Reactions were run in flame-dried round-bottomed flasks under an atmosphere of ultra high purity (UHP) argon. Diethyl ether (ether) and tetrahydrofuran (THF) were distilled from sodium benzophenone ketyl prior to use. Methylene chloride ($CH_2Cl_2$) was distilled from calcium hydride prior to use. All other compounds were purchased from Aldrich Chemical Company and used without further purification. All temperatures are understood to be in Centigrade (0° C.) when not specified. Analytical thin-layer chromatography (t.l.c.) was conducted with Silica Gel 60 $F_{254}$ plates (250 micrometer thickness, Merck). Column chromatography was performed using short path silica gel (particle size<230 mesh), flash silica gel (particle size 400–230 mesh), or Florisil® (200 mesh). Yields are not optimized. High performance liquid chromatography (HPLC) was carried out with a Rainin HPLX system equipped with two 25 mL/min preparative pump heads using Rainin Dynamax 10 mm×250 mm (semi-preparative) columns packed with 60 Å silica gel (8 μm pore size), either as bare silica or as C-18-bonded silica. Melting points were measured using a Mel-Temp metal-block apparatus and are uncorrected. Nuclear magnetic resonance (NMR) spectra were obtained either on a Varian XL-400 spectrometer, operating at 400 MHz for $^1H$ and 125 MHz for $^{13}C$. Chemical shifts are reported in parts per million (ppm, δ) downfield from tetramethylsilane. Splitting patterns are described as broad singlet (bs), broad doublet (bd), broad triplet (bt), broad quartet (bq), singlet (s), multiple (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform) and other conventional deuterated solvents. Combination of $CH_3CN$ and $H_2O$ in different concentrations are used as HPLC solvent system. Infrared (IR) spectra were obtained using a Perkin-Elmer 1600 FT-IR spectrometer. Resonances are reported in wavenumbers ($cm^{-1}$). Low resolution (LRMS) and high resolution (HRMS) mass spectra were obtained on a VG Instruments 70-S spectrometer run at 70 eV for electronic ionization (EI) and run with ammonia ($NH_3$) as a carrier for chemical ionization (CI). Combustion analyses were conducted by Atlantic Microlab (Norcross, Ga.). Various methods of purifying the products of the present invention are known and understood by those skilled in the art and the purification methods presented in the Examples is solely listed by way of example and is not intended to limit the invention.

The synthetic descriptions and specific examples that follow are only intended for the purposes of illustration, and are not to be construed as limiting in any manner to make compounds of the present invention by other methods.

EXAMPLE 1

Preparation of Trioxane Ether Dimer (6)

A flame-dried 10 mL round-bottomed flask was charged with 2,6-di-tert-butyl-4-methylpyridine (30.0 mg, 0.15 mmole) and methylene chloride (2 mL) at room temperature. To this mixture at 0° C. was added trifluoromethanesulfonic anhydride (25.0 μL, 0.15 mmole) via gas-tight syringe. A solution of trioxane alcohol (20.0 mg, 0.07 mmole) in methylene chloride (0.5 mL) was cooled to 0° C. and added to the reaction mixture via cannula. The reaction was stirred at 0° C. for 3 hours. The reaction was monitored by TLC until all trioxane alcohol was consumed.

The reaction was quenched with saturated sodium bicarbonate (3 mL) at 0° C. and diluted with methylene chloride (5 mL). Two layers were separated and the aqueous phase was extracted with methylene chloride (3×5 mL). The combined organic layers were washed with brine (15 mL), dried over magnesium sulfate, filtered and concentrated under reduced pressure. The crude product was purified by column chromatography on florisil (ethyl acetate-hexane, 10:90) to furnish the product (12.0 mg, 64%) as a colorless oil: FT-IR ($CHCl_3$, $cm^{-1}$) 3018, 2932, 2862, 1451, 1443, 1408, 1376, 1266, 1224, 1218, 1210, 1136, 1121, 1101, 1078, 1007; $^1H$ NMR ($CDCl_3$, 400 MHz) δ 5.16 (s, 2H), 3.53–3.42 (m, 4H), 3.50 (s, 6H), 2.36–2.28 (m, 2H), 2.25–2.19 (m, 2H), 2.01 (ddd, J=14.4, 4.4, 2.8 Hz, 2H), 1.85–1.48 (m, 16H), 1.38 (s, 6H), 1.34–1.20 (m, 6H); $^{13}C$ NMR ($CDCl_3$, 100 MHz) δ 105.10, 100.34, 85.34, 69.70, 69.51, 56.75, 48.55, 48.53, 42.25, 42.20, 37.49, 31.10, 29.92, 29.87, 29.56, 29.51, 27.18, 25.96, 25.27, 25.26; LRMS (CI, $NH_3$, rel intensity) 544 (M+18, 13), 484 (10), 424 (10), 255 (19), 223 (11), 196 (14), 195 (100), 137 (7); HRMS (CI) m/z calculated for $C_{28}H_{46}O_9$ ($M+NH_4^+$) 544.3486, found 544.3489.

EXAMPLE 2

Preparation of Trioxane Dimer (7)

To a flame-dried round-bottomed flask charged with 2,6-di-t-butyl-4-methylpyridine (22 mg, 0.11 mmol) in dry methylene chloride (1 mL) at 0° C. was added freshly opened triflic anhydride (18 μL, 0.11 mmol) via a syringe under argon atmosphere. After being stirred for 5 minutes the reaction mixture was slowly treated with a precooled solution of 4β-methyltrioxane alcohol (15 mg, 0.053 mmol) in methylene chloride (0.5 mL) at 0° C. via a cannula. The resultant mixture was stirred for 2.5 hours at 0° C., quenched with water (3 mL) at 0° C. and diluted with ether (5 mL), the organic layer was separated, and the aqueous layer was extracted twice with ether (5 mL×2). The combined organic layer was washed with brine solution (5 mL), and dried over anhydrous magnesium sulfate, filtered, and concentrated under reduced pressure to yield a crude product which was purified by silica gel column chromatography using 2:98 ethyl acetate:hexane to afford the corresponding trioxane ether dimer (9.5 mg, 65%) as a colorless oil. FT-IR ($CHCl_3$, $cm^{-1}$) 3000, 2931, 2859, 1465, 1373, 1408, 1376, 1218, 1213, 1138, 1122, 1100, 1009, 998, 947; $^1H$ NMR ($CDCl_3$, 400 MHz) δ 5.16 (s, 2H), 3.48 (s, 6H), 3.47 (m,4H), 2.48–2.38 (m, 2H), 2.26–2.16 (m, 2H), 1.78–1.46 (m 16H), 1.35–1.17 (m,6H), 1.28 (s, 6H), 0.97 (d, J=7.2 Hz, 6H); $^{13}C$ NMR ($CDCl_3$, 100 MHz) δ 107.41, 100.34, 100.32, 84.65, 69.72, 69.54, 56.85, 47.46, 42.11, 42.05, 39.88, 37.37, 30.94, 29.88, 29.85, 29.60, 29.54, 25.28, 25.26, 23.30, 19.20; LRMS (CI, $NH_3$, rel intensity) 572 ($M+NH_4^+$, 11), 452 (9), 269 (17), 237 (16), 209 (100), 137 (12); HRMS (CI) m/z calculated for $C_{30}H_{54}O_9N$ ($M+NH_4+$) 544.3799, found 544.3808.

EXAMPLE 3

Preparation of Trioxane Dimer (8)

To a flame-dried round-bottomed flask charged with 2,6-di-t-butyl-4-methylpyridine (22 mg, 0.11 mmol) in dry methylene chloride (1 mL) at 0° C. was added freshly opened triflic anhydride (18 μL, 0.11 mmol) via a syringe under argon atmosphere. After being stirred for 5 minutes the reaction mixture was slowly treated with a precooled solution of 4β-benzyltrioxane alcohol (15 mg, 0.053 mmol) in methylene chloride (0.5 mL) at 0° C. via a cannula. The resultant mixture was stirred for 2.5 hours at 0° C., quenched with water (3 mL) at 0° C. and diluted with ether (5 mL), the organic layer was separated, and the aqueous layer was extracted twice with ether (5 mL×2). The combined organic layer was washed with brine solution (5 mL), and dried over anhydrous magnesium sulfate, filtered, and concentrated under reduced pressure to yield a crude product which was purified by silica gel column chromatography using 2:98 ethyl acetate:hexane to afford the corresponding trioxane ether dimer (4.0 mg, 19%) as a colorless oil. FT-IR ($CHCl_3$, $cm^{-1}$) 3001, 2931, 2860, 1670, 1465, 1409, 1374, 1215, 1137, 1122, 1008, 972, 948; $^1H$ NMR ($CDCl_3$, 400 MHz) δ 7.30–7.26 (m, 4H), 7.23–7.20 (m, 6H), 5.20 (s, 2H), 3.51–3.42 (m, 4H), 3.04 (dd, J=4 Hz, J=13.2 Hz, 2H), 2.66 (m, 2H), 2.3 (t, J=12.8, 2H), 2.20 (m, 2H), 1.80–1.10 (m, 18H), 1.42 (s, 3H), 0.88 (m, 4H); $^{13}C$ NMR ($CDCl_3$, 100 MHz) δ 140.68, 128.99, 128.30, 125.88, 107.34, 100.55, 90.74, 84.84, 69.71, 69.54, 56.98, 47.30, 46.40, 42.00, 41.95, 39.00, 33.18, 30.77, 29.88, 29.86, 29.59, 29.56, 25.17, 23.57; LRMS (CI, $NH_3$, rel intensity) 724 ($M+NH_4^+$, 10), 664 (33), 604 (31), 345 (12) 285 (100); HRMS calculated for $C_{42}H_{62}O_9N$ ($M+NH_4+$) 724.4425, found 724.4433.

EXAMPLE 4

Preparation of Trioxane Bis-ester Dimer (9)

Trioxane alcohol (30 mg, 0.110 mmoles) was dried on a vacuum pump, purged with argon, and charged with 4-(dimethylamino)pyridine (30 mg, 0.246 mmoles). At room temperature 500 μL of methylene chloride was added. Then the reaction mixture was cooled to 0° C., phthaloyl dichloride (8 μL, 0.055 mmoles) was added via syringe, and the reaction mixture stirred overnight. The next morning the crude reaction mixture was directly adsorbed onto coarse silica gel and loaded onto a column. Column chromatography using 50% ethyl acetates, 50% hexanes yielded desired product as an oil (15 mg, 40% yield).

FT-IR ($CDCl_3$, $cm^{-1}$) 2954.5, 2931.0, 2848.7, 2249.4, 1710.2, 1466.6, 1431.0, 1372.5, 1296.2–1260.9, 1143.4–1119.9, 1072.9, 1008.2, 926.0–890.7, 761.4–696.8, 643.9; $^1H$ NMR ($CDCl_3$, 400 MHz) 7.728–7.762 (m, 2H), 7.529–7.479 (m, 2H), 5.153 (s, 2H), 4.433–4.372 (m, 2H), 4.351–4.286 (m, 2H), 3.483 (s, 6H), 2.400–2.222 (m, 4H), 2.052–1.935 (m, 2H), 1.882–1.609 (m, 6H), 1.609–1.409 (m, 6H), 1.409–1.303 (m, 6H), 1.297–1.150 (m, 6H), 0.922–7.766 (m, 4H); $^{13}C$ NMR ($CDCl_3$, 400 MHz) 167.499, 132.149, 130.905, 128.834, 105.174, 100.107, 85.116, 64.597, 56.700, 48.522, 42.188, 37.462, 30.991, 29.322, 28.973, 27.107, 25.924, 25.158; HRMS calculated for $C_{36}H_{50}O_{12}$, 692.3646 found: 692.3663.

EXAMPLE 5

Preparation of Trioxane Bis-ester Dimer (10)

Trioxane alcohol (30 mg, 0.110 mmoles) was dried on a vacuum pump, purged with argon, and charged with 4-(dimethylamino)pyridine (45 mg, 0.36 mmoles). At room temperature, 500 μL of methylene chloride were added. The reaction mixture was cooled to 0° C., and isophthaloyl dichloride (11 mg, 0.055 mmoles) was added via syringe. The reaction mixture stirred overnight and the next morning the crude reaction mixture was directly adsorbed onto coarse silica gel and loaded onto a column. Column chromatography using 50% ethyl acetates, 50% hexanes yielded desired product as an oil (14.1 mg, 37% yield).

FT-IR ($CDCl_3$, $cm^{-1}$) 2928.2, 2856.7, 1717.8, 1242.7, 1210.0, 1136.2, 1008.2, 779.8, 771.9, 761.8, 756.2, 752.0, 746.3, 735.1, 667.8; $^1H$ NMR ($CDCl_3$, 400 MHz) 8.618 (t, J=1.4 Hz, 1H), 8.153 (dd, J=7.8 Hz, 1.8 Hz, 2H), 7.457 (t, J=7.8 Hz, 1H), 5.145 (d, J=0.8, 2H), 4.410–4.284 (m, 4H), 3.457 (s, 6H), 3.457 (s, 6H), 2.457–2.069 (m, 4H), 2.054–1.841 (m, 2H), 1.846–1.584 (m, 10H). 1.584–1.391 (m, 6H), 1.317 (2, 6H), 1.269–0.943 (m, 6H), $^{13}C$ NMR ($CDCl_3$, 400 MHz) 165.747, 133.712, 130.791, 130.175, 128.531, 105.250, 100.091, 85.185, 64.491, 56.731, 48.552, 42.424, 37.485, 31.007, 29.573, 29.300, 27.115, 25.932, 25.204; HRMS calculated for $C_{36}H_{50}O_{12}$:692.3646, found: 692.3656.

EXAMPLE 6

Preparation or Bis-ester Dimer (11)

An oven-dried 10 mL one-necked round-bottomed flask was charged with terephthaloyl chloride (95.7 mg, 0.05 mmol) and dry methylene chloride (1 mL) and cooled to 0° C. To this solution was added triethylamine (200 μL, 1.4 mmol) via a gas-tight syringe. After the reaction mixture was slowly warmed to room temperature over 0.5 hours and stirred for 0.5 hours, it was treated with trioxane alcohol (58.5 mg, 0.22 mmol) in methylene chloride (1 mL). This reaction mixture was stirred for 1 hour and the solvent was removed at reduced pressure to yield a crude product which was directly serparated by silica gel column chromatography to afford the corresponding pure bis-trioxane carboxylate ester (51.8 mg, 71%) as a coloress oil: FT-IR (neat) 1720; $^1H$ NMR ($CDCl_3$, 400 MHz) δ 8.10 (s, 4H), 5.21 (s, 2H), 4.48–4.35 (m, 4H), 3.53 (s, 6H), 2.45–2.30 (m, 4H), 2.06–2.00 (m, 2H), 1.91–1.66 (m, 4H), 1.65–1.50 (m, 14H), 1.45–1.34 (m, 2H), 1.39 (s, 6H), 1.34–1.21 (m, 2H); $^{13}C$ NMR ($CDCl_3$, 100 MHz) δ 166.85, 134.08 129.55, 105.29, 100.11, 85.19, 64.38, 56.71, 48.56, 42.33, 37.48, 31.00, 29.43, 29.18, 27.10, 25.93, 25.18; LRMS ($NH_3$, rel intensity) 692 (M+18, 9) 657 (1), 632 (11), 572 (64) 466 (11), 404 (12), 348 (22), 318 (17), 233 (16), 195 (100), 177 (11), 168 (24), 137 (14), 119 (35), 117 (23); HRMS (CI, $NH_3$) calculated for $C_{36}H_{54}NO_{12}$ ($M+NH_4$) 692.3646, found 692.3662.

EXAMPLE 7

Preparation of Trioxane Bis-ester Dimer (12)

The 2,6-naphalenedicarboxylic acid and stir bar was dried on a vacuum pump in a 50 mL round bottom flask. Under argon, methylene chloride (2.0 mL) was added via syringe, and then the reaction mixture was cooled to 0° C. The oxalyl chloride was added slowly by syringe, followed by a few drops of DMF. The reaction was allowed to stir for four hours. The crude product was rotovapped down three times with chloroform to yield a yellow solid. The acid chloride was used without purification in the next step.

The trioxane alcohol (40 mg, 0.147 mmoles) was dried on a vacuum pump with stir bar for several hours. The under argon, acid chloride (19 mg, 0.074 mmoles) and 4-(dimethylamino)pyridine (36 mg, 0.296 mmoles) were added. The mixture was cooled to 0° C. in an ice bath and methylene chloride (2.0 mL) was added via syringe. The mixture was allowed to stir about 24 hours with gradual warming to room temperature. Even after this amount of time, however, there was still some trioxane alcohol remaining by TLC. The methylene chloride was removed under vacuum and loaded directly onto a flash silica gel column. Column chromatography using 15% ethyl acetate and 85% hexanes yielded the product as a white solid. $R_f$=0.7 in 20% ethyl acetate and 80% hexanes. Recrystallization from 100% hexanes yielded a white solid (16 mg, 30% yield), mp 178°–180° C.

FT-IR (CDCl$_3$, cm$^{-3}$) 2919.2, 2848.7, 2355.1, 2249.4, 1707.5, 1601.7, 1460.7, 1443.1, 1401.9, 1378.4, 1337.3, 1280.0, 1262.4, 1209.5, 1183.0, 1134.6, 1118.4, 1096.4, 1077.3, 1006.8, 961.2, 950.9; $^1$H NMR (CDCl$_3$, 400 MHz) 8.63 (2H, s), 8.12 (2H, dd, J=8.4, 1.6 Hz), 8.01 (2H, d, J=8.4 Hz), 5.23 (2H, s), 4.58–4.34 (4H, m), 3.50 (6H, s), 2.59–2.40 (2H, m), 2.35 (2H, dt, J=14.2, 3.6 Hz), 2.11–1.96 (2H, m), 1.93–1.74 (6H, m), 1.74–1.66 (4H, m), 1.66–1.48 (8H, m), 1.40 (6H, s), 1.32–1.15 (4H, m); $^{13}$C NMR (CDCl$_3$, 400 MHz) 166.33, 134.52, 130.57, 129.64, 129.54, 125.97, 105.26, 100.10, 85.20, 64.36, 56.73, 48.56, 42.34, 37.48, 31.01, 29.46, 29.25, 27.11, 25.95, 25.20; HRMS calculated for C$_{40}$H$_{52}$O$_{12}$, 742.3803, found: 742.3814.

EXAMPLE 8

Preparation of Trioxane Bis-ester Dimer (13)

Trioxane alcohol (30 mg, 0.110 mmoles) was dried on a vacuum pump. Under argon, a stir bar, 4-(dimethylamino)pyridine (30 mg, 0.243 mmoles) and 2,6-pyridine dicarboxyl dichloride was added at room temperature, and the solution was cooled to 0° C. Methylene chloride (1.0 mL) was added via syringe. The reaction mixture stirred for 10 hours with gradual warming to room temperature. Then the methylene chloride was removed under light vacuum and the crude oil was loaded directly onto a flash silica gel column. Column chromatography using 10% ethyl acetates, 90% hexanes yielded desired product as an oil (10 mg, 27% yield). ($R_f$=0.7 in 50% ethyl acetates and 50% hexanes).

FT-IR (CDCl$_3$, cm$^{-1}$) 3683.1, 2989.1, 2919.2, 2860.5, 2363.9, 2334.4, 1736.9, 1719.2, 1601.7, 1584.1, 1448.9, 1319.7, 1284.4, 1243.3, 1219.9, 1215.7, 1210.0, 1142.3, 1121.2, 788.9–729.2, 663.4, 451.8; $^1$H NMR (CDCl$_3$, 400 MHz) 8.27 (2H, d, J=8.0 Hz), 7.99 (1H, t, J=8.0 Hz), 5.21 (2H, s), 4.51–4.47 (4H, m), 3.51 (6H, s), 2.51–2.37 (1H, m), 2.37–2.23 (2H, m), 2.08–1.93 (1H, m), 1.93–1.70 (6H, m), 1.70–1.46 (12H, m), 1.37 (6H, s), 1.29–1.16 (4H, s), 0.95–0.73 (2H, m); $^{13}$C NMR (CDCl$_3$, 400 MHz) 164.45, 148.55, 138.13, 127.75, 105.19, 100.06, 85.15, 65.50, 56.73, 48.54, 42.48, 37.46, 30.99, 29.70, 29.29, 27.10, 25.91, 25.19.

EXAMPLE 9

Preparation of Trioxane Bis-ester Dimer (14)

Trioxane alcohol (50 mg, 0.183 mmoles) was dried on a vacuum pump, purged with argon, and charged with 4-(dimethylamino)pyridine (45 mg, 0.36 mmoles). At room temperature, a few drops of triethylamine and 500 µL of methylene chloride were added. The reaction mixture was cooled to 0° C., and succinyl dichloride (10 µL, 0.092 mmoles) was added via syringe, after which time the solution turned from clear to deep purple and opaque. The reaction mixture stirred overnight and the next morning the crude reaction mixture was directly adsorbed onto coarse silica gel and loaded onto a column. Column chromatography using 20% ethyl acetates, 80% hexanes yielded desired product as an oil (8 mg, 14% yield).

FT-IR (CDCl$_3$, cm$^{-1}$) 3013.2, 2978.0, 2919.2, 2860.5, 1725.1, 1460.7, 1237.4, 1208.0, 1055.2, 1002.4, 896.6, 768.6, 766.8, 753.5, 743.3, 738.1, 734.1, 727.8, 671.6; $^1$H NMR (CDCl$_3$, 400 MHz) 5.122 (d, J=0.8 Hz, 2H), 4.204–4.065 (m, 4H), 3.478 (s, 6H), 2.602 (s, 4H), 2.588–2.430 (m, 12H), 2.430–2.294 (m, 6H), 2.294–2.089 (m, 12H), 1.953–1.690 (m, 4H); $^{13}$C NMR (CDCl$_3$, 400 MHz) 172.278, 105.212, 100.107, 85.147, 63.694, 56.715, 48.538, 42.181, 37.485, 31.007, 29.376, 29.179, 20.095, 27.115, 25.940, 25.173; HRMS calculated for C$_{32}$H$_{50}$O$_{12}$:626.3646, found:644.3649.

EXAMPLE 10

Preparation of Trioxane Bis-ester Dimer (15)

Trioxane alcohol (50 mg, 0.183 mmoles) was dried on a vacuum pump, purged with argon, and charged with 4-(dimethylamino)pyridine (45 mg, 0.36 mmoles). At room temperature, a few drops of triethylamine and 500 µL of methylene chloride were added. The reaction mixture was cooled to 0° C., and glutaryl dichloride (12/L, 0.092 mmoles) was added via syringe at which time the solution turned from clear to a bright yellow color. The reaction mixture stirred overnight and the next morning the crude reaction mixture was adsorbed onto coarse silica gel and loaded onto a column. Column chromatography using 50% ethyl acetates, 50% hexanes yielded desired product as an oil (7.2 mg, 12% yield).

FT-IR (CDCl$_3$, cm$^{-1}$) 3683.1, 3029.7, 2996.7, 2930.8, 2858.9, 1726.7, 1600.8, 1213.9, 1137.5, 1002.4, 755.6, 673.3; $^1$H NMR (CDCl$_3$, 400 MHz) 5.121 (d, J=1.2 Hz, 2H), 4.185–4.041 (m, 4H), 3.475 (s, 6H), 2.342 (t, J=7.4 Hz, 4H), 2.316–2.244 (m, 2H), 2.241–2.137 (m, 2H), 2.082–1.988 (m, 8H), 1.9825 (ddd, J=14.4, 4.6, 2.6, 2H), 1.916 (t, J=7.4 Hz, 2H), 1.857–1.730 (m, 2H), 1.730–1.615 (m, 4H), 1.615–1.441 (m, 8H), 1.353 (s, 6H); $^{13}$H NMR (CDCl$_3$, 400 MHz) 172.900, 105.181, 100.069, 85.117, 63.376, 56.685, 48.523, 42.166, 37.455, 33.351, 30.984, 29.368, 29.118, 27.093, 25.917, 25.158, 20.114; HRMS calculated for C$_{33}$H$_{52}$O$_{12}$ (M+NH$_4^+$): 658.3801, found: 658.3795.

EXAMPLE 11

Preparation of Trioxane Bis-ester Dimer (16)

Trioxane alcohol (50 mg, 0.183 mmoles) was dried on a vacuum pump, purged with argon, and charged with 4-(dimethylamino)pyridine (45 mg, 0.36 mmoles). At room temperature, a few drops of triethylamine and 500 µL of methylene chloride were added. The reaction mixture was cooled to 0° C., and adipoyl dichloride (13 µL, 0.092 mmoles) was added via syringe at which time the solution turned from clear to cloudy white. The reaction mixture stirred overnight and the next morning the crude reaction mixture was directly adsorbed onto coarse silica gel and loaded onto a column. Column chromatography using 50% ethyl acetates, 50% hexanes yielded desired product as an oil (13.7 mg, 14% yield).

FT-IR (CDCl$_3$, cm$^{-1}$) 3015.2, 2932.5, 2860.5, 1728.6, 1209.7, 1134.2, 1003.4, 780.4, 774.3, 770.2, 755.2, 752.2, 747.0, 740.7, 734.1, 728.0; $^1$H NMR (CDCl$_3$, 400 MHz)

5.123 (s, 2H), 4.240–4.123 (m, 4H), 3.476 (s, 6H), 3.131 (td, J=9.0 Hz, 2.4 Hz, 4H), 2.393–2.188 (m, 9H), 2.188–2.042 (m, 2H), 2.039–1.923 (m, 2H), 1.923–1.727 (m, 4H) 1.72–1.431 (m, 12H), 1.355 (s, 6H), 1.287–1.124 (m, 3H); $^{13}$C NMR (CDCl$_3$, 400 MHz) 169.320, 126.839, 117.084, 105.197, 100.053, 85.147, 64.280, 56.708, 54.804, 48.538, 42.079, 38.069, 37.470, 30.999, 29.330, 27.411, 25.940, 25.166, 20.979; HRMS calculated for C$_{33}$H$_{52}$O$_{12}$ (M+NH$_4{}^+$): 672.3959, found: 672.3948.

EXAMPLES 12 AND 13

Preparation of Trioxane Bis-ester Dimers (17 and 18)

The 1,3-cyclohexanedicarboxylicacid (500 mg, 2.90 mmoles) as a mixture of cis and trans isomers was placed in a 25 mL round bottom flask and dried on a vacuum pum. Then under argon, a stir bar and methylene chloride (1 mL) were added and the reaction flask was cooled to 0° C. Slowly the oxalyl chloride as 2.0M solution in methylene chloride (3.2 mL, 6.39 mmoles) was added via syringe, followed by a few drops of DMF. The reaction stirred warming gradually from 0° C. to room temperature over 10 hours. Then the methylene chloride was removed under vacuum and the product was used in next step without further purification.

The trioxane alcohol (47 mg, 0.172 mmoles) was dried on a vacuum pump for several hours. Then the flask was charged with the diacid chloride (18 mg, 0.086 mmoles) and 4-(dimethylamino) pyridine (42 mg, 0.346 mmoles) and cooled to 0° C. The methylene chloride (1 mL) was added via syringe and the reaction mixture stirred warming gradually from 0° C. to room temperature, over 10 hours. The reaction was quenched with water and extracted three times with ether. The organic layers were washed with brine solution, dried over magnesium sulphate and concentrated on the rotovap. Column chromatography using 5% ethyl acetate and 95% hexanes yielded the products as an oil. The isomers were separated by high pressure liquid chromatography.

compound 17

FT-IR (CDCl$_3$, cm$^{-1}$) 2931.0, 2860.5, 1716.3, 1454.4, 1374.4, 1359.4, 1264.4, 1204.4, 1137.0, 1119.5, 1007.0, 922.4, 915.9, 910.0, 901.6, 893.8, 757.4, 752.0, 746.9, 742.4, 737.0, 731.6, 726.0, 722.6; $^1$H NMR (CDCl$_3$, 400 MHz) 5.14 (2H, s), 4.27–3.98 (4H, m), 3.50 (6H, s), 2.77–2.61 (2H, m), 2.40–2.25 (4H, m), 2.25–2.19 (2H, m), 2.19.2.11 (2H, m), 2.07–1.91 (4H, m), 1.91–1.74 (4H, m), 1.73–1.63 (6H, m), 1.63–1.47 (14H, m), 1.37 (6H, s); $^{13}$H NMR (CDCl$_3$, 400 MHz) 164.22, 105.20, 100.08, 85.13, 63.25, 56.73, 48.53, 42.62, 42.20, 37.47, 31.00, 29.33, 29.07, 28.29, 27.91, 27.10, 25.94, 25.18, 24.78.

compound 18

FT-IR (CDCl$_3$, cm$^{-1}$) 2938.2, 2861.1, 2258.7, 2246.8, 1722.1, 1464.0, 1449.2, 1376.5, 1260.7, 1206.9, 1135.7, 1120.9, 1009.1, 920.6, 914.7, 909.1, 903.8, 900.1, 896.0, 758.2, 753.2, 750.2, 745.6, 742.1, 733.0, 730.0, 723.1, 718.1, 654,8, 649.2, 478.6; $^1$H NMR (CDCl$_3$, 400 MHz) 5.139 (2H, d, J=1.2 Hz), 4.28–4.40 (4H, m), 3.494 (6H, s), 2.74–2.57 (2H, m), 2.44–2.25 (4H, m), 2.25–2.13 (4H, m), 2.09–1.92 (4H, m), 1.77–1.63 (6H, m), 1.63–1.46 (8H, m), 1.37 (6H, s), 1.30–1.12 (6H, m); $^{13}$C NMR (CDCl$_3$, 400 MHz) 175.13, 105.20, 100.08, 85.13, 63.60, 60.34, 56.70, 48.53, 42.63, 42.15, 37.46, 30.99, 29.30, 29.05, 28.29, 27.10, 25.93, 25.17, 24.80.

EXAMPLE 14

Preparation of Trioxane Bis-ester Dimer (19)

The trans-3,6-Endomethylene-1,2,3,6-tetrahydrophthaloyl chloride (500 mg, 2.28 mmoles) was placed in a 25 mL round bottom flask and dried on a vacuum pump. Then a stir bar was added and under argon, methylene chloride (1 mL) and the reaction flask was cooled to 0° C. Slowly the oxalyl chloride was as 2.0M solution in methylene chloride (2.74 µL, 5.48 mmoles) was added via syringe, followed by a few drops of DMF. The reaction stirred warming graduatlly from 0°0 C. to room temperature over 10 hours. Then the methylene chloride was removed under vacuum and the product was used in next step without further purification.

The trioxane alcohol (30 mg, 0.110 moles) was dried on a vacuum pump for several hours. The flask was charged with the diacid chloride (14 mg, 0.055 mmoles) and 4-(dimethylamino) pyridine (27 mg, 0.220 mmoles) and cooled to 0° C. The methylene chloride (1 mL) was added via syringe and the reaction mixture stirred warming gradually from 0° C. to room temperature over 10 hours.

FT-IR (CDCL$_3$, cm$^{-1}$) 2931.0, 2860.5, 2249.4, 1725.1, 1460.7, 1372.5, 1265.3, 1247.7, 1209.5, 1184.5, 1114.0, 1045.0, 1008.2, 904.2, 733.2, 656.2, 650.9, 645.6; $^1$H NMR (CDCl$_3$, 400 MHz) δ 6.30–6.27 (m, 1H), 6.11–6.06 (m, 1H), 5.16–5.13 (m, 2H), 4.34–3.99 (m, 6H), 3.50 (6H, d, J=2.4 Hz), 3.39–3.38 (m, 2H), 3.30–3.21 (m, 1H), 3.16–3.09 (m, 1H) 2.43–2.18 (m, 2H), 2.09–1.93 (m, 2H), 1.92–1.42 (m, 8H), 1.38 (s, 6H), 1.35–1.16 (m, 6H).

EXAMPLE 15

Preparation of Bis-trioxane phosphate ester (20)

Trioxane alcohol (17.5 mg, 0.064 mmoles) was dried on a vacuum pump. Under argon, 500-µL THF was added to the solid and the solution was cooled to 0° C. A 1.0M lithium-hexamethyldisilazide (LHMDS) solution in THE (90 µL, 0.080 mmoles) was added dropwise via gas tight syringe. The resulting mixture stirred ten minutes at 0° C. then the phenyl dichlorophosphate (6.8 mg, 0.032 mmoles) was added. The reaction mixture was kept at 0° C., and then was warmed to room temperature and stirred for 40 minutes. The reaction mixture was cooled to 0° C., quenched with water, and the organic layer was extracted with ether three times. The organic layers were washed with saturated sodium chloride and dried over magnesium sulfate. Column chromatography using 20% ethyl acetates and 80% hexanes yielded the product as an oil (11.5 g, 52% yield).

FT-IR (CDCl$_3$, cm$^{-1}$) 4200.2, 3683.1, 3612.6, 3025,0, 2931.0, 2390.4, 1519.4, 1425.4, 1213.9, 1020.0, 926.0–884.8, 790.0–702.7, 667.4, 643.9; $^1$H NMR (CDCl$_3$, 400 MHz) 7.382–7.226 (m, 2H), 7.226–7.131 (m, 2H), 7.131–7.018 (m, 1H), 5.038 (s, 2H), 4.4204.04 (m, 4H), 3.407 (d, J=1.6 Hz, 6 H), 2.537–2.122 (m, 4H), 2.122–1.875 (m, 4H), 1.875–1.433 (m, 12H), 1.4077–1.277 (m, 8H), 1.305 (s, 6H); $^{13}$C NMR (CDCl$_3$, 400 MHz) 129.669, 124.890, 120.095, 105.204, 100.046, 85.056, 67.430, 67.283, 56.700, 48.508, 41.653, 37.455, 30.931, 29.4114, 29.308, 27.093, 25.917, 25.090.

EXAMPLE 16

Preparation of Bis-trioxane phosphate ester (21)

Trioxane alcohol (20 mg, 0.073 mmoles) was dried on a vacuum pump. Under argon, 500 µL THF was added to the solid and the solution was cooled to 0° C. A 1.0M LHMDS solution in THF (92 µL, 0.091 mmoles) was added dropwise via gas tight syringe. The resulting mixture stirred ten minutes at 0° C. then the phenyl dichlorophosphate (5.5 mg, 0.037 mmoles) was added. The reaction mixture was kep at 0° C., and then was warmed to room temperature and stirred for 40 minutes. The reaction mixture was cooled to 0° C., quenched with water, and the organic layer was extracted with ether three times. The organic layers were washed with saturated sodium chloride and dried over magnesium sulfate. Column chromatography using 20% ethyl acetates and 80% hexanes yielded the product as an oil (32 g, 69% yield).

FT-IR (CDCl$_3$, cm$^{-1}$) 2249.4, 1460.7, 1378.4, 1213.9, 1096.4, 1008.2, 908.3, 779.1, 714.4, 643.9; $^1$H NMR (CDCl$_3$, 400 MHz) 5.108 (s, 2H), 4.123–4.073 (m, 4H), 3.743 (m, 3H), 3.476 (s, 6H), 2.385–2.195 (m, 4H), 2.072–1.899 (m, 2H), 1.899–1.724 (m, 2H), 1.724–1.645 (m, 4H), 1.645–1.443 (m, 12H), 1.353 (s, 6H), 1.280–1.157 (m, 4H); $^{13}$C NMR (CDCl$_3$, 400 MHz) 105.197, 100.076, 85.071, 66.562, 56.708, 54.265, 48.538, 41.657, 37.470, 30.984, 29.346, 29.323, 27.115, 25.932, 25.143.

EXAMPLE 17

Preparation of Bis-trioxane ester (22)

Trioxane alcohol (30 mg, 0.110 mmoles) and stir bar were dried on a vacuum pump. Under argon, THF (2.5 mL) was added and the solution was cooled to 0° C. A 1.0M LHMDS solution in THE (138 μL, 1.38 mmoles) was added dropwise via gas-tight syringe. The resulting mixture stirred ten minutes at −78° C., and then the methyl phosphonic acid dichloride (5 μL, 0.055 mmoles) was added. The reaction mixture was kept at −78° C., and then was warmed to room temperature and stirred for 40 minutes. The reaction mixture was cooled to 0° C. quenched with water, and the organic layer was extracted with ether three times. The organic layers were washed with saturated sodium chloride, dried over magnesium sulphate, and concentrated on the rotovap. Column chromatography using 15% ethyl acetates and 85% hexanes yielded the product as an oil (19.9 mg, 30% yield), R$_f$=0.9 in 50% ethyl acetate and 50% hexanes.

FT-IR (CDCl$_3$, cm$^{-1}$) 3694.9, 3013.2, 2954.5, 2931.0, 2864.9, 2359.6, 2339.1, 1219.9, 1215.9, 1210.0, 789.5, 784.0, 778.9, 771.8, 767.5, 761.2, 754.1, 749.8, 740.3, 735.6, 732.4; $^1$H NMR (CDCl$_3$, 400 MHz) 5.14 (2H d, J=1.2 Hz), 3.73–3.54 (4H, m), 3.49 (6H, s), 2.31 (2H, dt, J=13.6, 3.5 Hz), 2.15 (2H, dq, J=9.6, 2.0 Hz), 2.00 (2H, dq, J=14.4, 2.4 Hz), 1.91–1.74 (4H, m), 1.74–1.64 (6H, m), 1.64–1.61 (2H, m), 1.57 (6H, s), 1.37 (3H, s), 1.34–1.33 (8H, m), 0.95–0.78 (2H, m); $^{13}$C NMR (CDCl$_3$, 400 MHz) 105.204, 100.084, 85.07, 66.59, 66.53, 56.72, 48.53, 41.62, 37.46, 30.97, 29.31, 27.10, 25.93, 25.13.

EXAMPLE 18

Preparation of Diethylene Glycol Diester Dimer (23)

The 3,6,9-trioxaundecandioic acid (500 mg, 2.25 mmoles) purchased from Hoechst Celanese Corporation, methylene chloride (1.0 mL) and stir bar in a 50 mL round bottom flask were cooled to 0° C. under argon. The oxalyl chloride as a 2.0M solution in methylene chloride (2.70 mL, 5.40 mmoles) was added slowly via syringe. After a few minutes, a few drops of DMF was added and the reaction stirred for six hours at 0° C. with gradual warming to room temperature. The mixture was concentrated on the rotovap and then rotovapped down three times with carbon tetrachloride to yield a yellow solid. The acid chloride was used without purification in the next step.

The trioxane alcohol (27 mg, 0.099 mmoles) was dried on a vacuum pump with stir bar. Under argon, 4-(dimethylamino) pyridine (49 mg, 0.397 mmoles) and the acid chloride (61 mg, 0.238 mmoles) were added. The reaction mixture was cooled to 0° C. and then methylene chloride (2.0 mL) was added via syringe. The mixture was stirred overnight with gradual warming to room temperature.

The methylene chloride was removed under light vacuum and the crude oil was loaded directly onto a column. Column chromatography using 20% ethyl acetate and 80% hexanes yielded the product as a clear, colorless oil (13.3 mg, 18%).

FT-IR (CDCl$_3$, cm$^{-1}$) 2931.0, 2860.5, 2249.4, 1746.1, 1448.3, 1274.9, 1271.0, 1209.8, 1148.7, 1118.1, 1008.0, 919.9, 915.7, 911.5, 900.4, 893.9, 753.7, 745.7, 742.6, 736.1, 726.2, 716.7, 711.1, 652.5; $^1$H NMR (CDCl$_3$, 400 MHz) 5.13 (2H, d, J=1.2), 4.34–4.18 (4H, m), 4.15 (4H, d, J=1.2), 3.81–3.64 (8H, m), 3.49 (6H, s), 2.41–2.27 (2H, M), 2.27–2.12 (2H, m), 1.88–1.72 (2H, m), 1.72–1.63 (4H, m), 1.63–1.46 (10H, m), 1.37 (6H, s), 1.33–1.21 (8H, m); $^{13}$C NMR (CDCl$_3$, 400 MHz) 170.44, 105.23, 100.04, 85.11, 70.91, 68.61, 63.77, 56.71, 48.53, 42.11, 37.46, 30.96, 29.42, 27.08, 25.92, 25.15, 20.41, 19.78.

EXAMPLE 19

Preparation of 4β-Hydroxymethyl Trioxane Terephthalate Dimer (24)

A 10 mL 3-necked round-bottomed flask was fitted with an inlet line from an argon gas tank, an outlet line, and a septum. This flask was charged with paraformaldehyde (753 mg, 25.1 mmol), and the outlet line was connected through a glass tube to a 100 mL 3-necked round-bottomed flask, also fitted with an outlet line to a bubbler and a septum. To a freshly prepared solution of Li(i-PrN)$_2$ (5.52 mmol) in THF/hexane (7.1 mL/3.9 mL) at −78° C. in the 100 mL flask was added via cannula a solution of Z-methoxyethylidene-2-(2'-cyanothyl)cyclohexanone (900 mg, 5.02 mmol) in THF (39 mL) at −78° C. for 5 minutes, the reaction mixture was warmed to room temperature and stirred for 20 minutes. This yellow/brown enolate solution was cooled to −78° C. while the paraformaldehyde was heated to 160° C. The resulting gaseous formaldehyde was blown over the vigorously stirring enolate solution with argon over pressure. After the addition, the mixture was stirred at −78° C. for 15 minutes, warmed to room temperature over 2 hours, and stirred at room temperature for 6 hours. The reaction was quenched by dropwise addition of H$_2$O (1 mL). The resulting mixture was diluted with H$_2$O (50 mL) and ether (50 mL). The organic phase was seperated, and the aqueous phase was extracted with ether (50 mL×2). The organic portions were combined, washed with saturated aqueous NaCl, dried over MgSO$_4$, filtered, and concentrated under reduced pressure. This crude product was purified by column chromatography (flash, 5% to 20% EtOAc/hexane) to give the desired product, a 1:1 diastereomeric mixture (931 mg, 4.45 mmol, 89%), as a pale yellow oil: $^1$H NMR(CDCl$_3$, 400 MHz) δ 5.87 (d, J=1.6 Hz, 1H), 5.86 (d, J=1.6 Hz, 3.83 (m, 2H), 3.76 (m, 2H), 3.54 (s,3H), 3.53 (s, 1H), 3.09 (m, 1H), 2.96 (m, 1H), 2.67 (m, 2H), 2.24 (m, 2H), 2.08–1.94 (m, 2H), 1.88 (m, 4H), 1.78–1.64 (m, 4H), 1.63–1.52 (m, 8H), 1.46 (m, 2H), 1.30–1.18 (m, 2H); $^{13}$C NMR (CDCl$_3$, 100MHz) δ 141.2, 141.1, 121.9, 121.5, 117.3, 117.2, 63.1, 61.8, 59.3, 59.2, 33.6, 32.4, 31.8, 31.1, 31.0, 30.3, 29.9, 28.03, 27.96, 26.4, 26.2, 21.7, 21.3; IR (CHCl$_3$, cm$^{-1}$) 3617, 3470, 3020, 2933, 2858, 2242, 1675, 1449, 1239, 1127; LRMS (EI, rel intensity) 209 (M$^+$, 11), 125 (100), 93 (17), 84 (5), 45 (11); HRMS (EI) m/z calculated for C$_{12}$H$_{19}$NO$_2$ (M$^+$): 209.1416, found 209.1419.

To a solution of the above α-hydroxymethyl nitrile (280 mg, 1.34 mmol) in $CH_2Cl_2$ (13 mL) at 0° C. was added via a syringe 2,6-lutidine (234 μL, 2.01 mmol). This mixture was stirred for 5 minutes at 0° C. At that time, t-BuMe$_2$SiTf (400 μL, 1.74 mmol) was added via syringe, and the solution was stirred for an additional 30 minutes at 0° C. The reaction was quenched by addition of $H_2O$ (3 mL). The resulting mixture was diluted with $H_2O$ (20 mL) and ether (20 mL). The organic phase was separated, and the aqueous phase was extracted with ether (20 mL×2). The organic portions were combined, washed with saturated NaCl, dried over anhydrous $MgSO_4$, filtered, and concentrated under reduced pressure. This crude product was purified by column chromatography (short path, 1% to 10% EtOAc/hexane) to give the desired product, a 1:1 mixture of diastereomers (397 mg, 1.22 mmol, 91%), as a colorless oil: $^1$H NMR (CDCl$_3$, 400 MHz) δ 5.86 (d, J=1.6 Hz, 1H), 5.84 (d, J=2.0 Hz, 1H), 3.81–3.66 (m, 4H), 3.54 (s, 3H), 3.51 (s, 3H), 3.10 (m, 1H), 2.92 (m, 1H), 2.59 (m, 2H), 2.02–1.81 (m, 7H), 1.78–1.65 (m, 4H), 1.60 (m, 3H), 1.53 (m, 5H), 1.45 (m, 1H), 1.29–1.17 (m, 2H), 0.91 (s, 9H), 0.90 (s, 9H), 0.09 (s, 6H), 0.08 (d, J=2.0 Hz, 6H); $^{13}$C NMR (CDCl$_3$, 100MHz) δ 141.28, 141.27 141.2, 141.1, 122.1, 121.4, 117.3, 117.34, 117.32, 63.6, 62.1, 59.2, 33.5, 32.5, 31.9, 31.3, 31.11, 31.06, 30.4, 29.9, 28.2, 28.2, 26.4, 26.3, 25.8, 21.8, 21.5, 18.24, 18.22, −5.4, −5.5; IR (CHCl$_3$, cm$^{-1}$) 3017, 2931, 2858, 2243, 1677, 1463, 1258, 1128, 839; LRMS (EI, rel intensity) 323 (M$^+$, 2), 266 (100), 234 (26), 160 (17), 125 (23), 89 (33), 73(19); HRMS (EI) m/z calculated for $C_{18}H_{33}NO_2Si$ (M$^+$): 323.2281, found 323.2280.

To a solution of the above t-butyldimethylsilyl ether (330 mg, 1.02 mmol) in ether (7.8 mL) at −78° C. for 5 minutes then warmed to room temperature and stirred for 3 hours. At that time, the reaction was cooled to 0° C. and quenched with dropwise addition of $H_2O$ (1 mL). The resulting mixture was diluted with $H_2O$ (20 mL) and ether (20 mL). The organic phase was separated, and the aqueous phase was extracted with ether (20 mL×2). The organic portions were combined, washed with saturated aqueous NaCl, dried over anhydrous $MgSO_4$, filtered, and concentrated under reduced pressure. This crude product was purified by column chromatography (short path, 1% to 20% EtOAc/hexane) to give the desired product, a 1:1 mixture of diastereomers (260 mg, 0.76 mmol, 75%), as a yellow oil: $^1$H NMR (CDCl$_3$, 400 MHz) δ 5.78 (d, J=2.0 Hz, 1H), 5.73 (d, J=2.4 Hz, 1H), 3.75–3.52 (m, 4H), 3.49 (s, 3H), 3.47 (s, 3H), 2.81 (m, 1H), 2.72 (m, 2H), 2.63 (m, 1H), 2.18 (s, 3H), 2.14 (s, 3H), 1.98–1.83 (m, 3H), 1.80–1.68 (m, 4H), 1.57 (m, 3H), 1.46 (m, 7H), 1.25(ddd,J=14.0, 6.8, 4.8 Hz, 1H), 1.15 (m, 1H), 0.844 (s, 9H), 0.840 (s, 9H), 0.00 (d, J=4.0 Hz, 6H), −0.05 (d, J=4.0 Hz, 6H); $^{13}$C NMR (CDCl$_3$, 100 MHz) δ 213.1, 212.4, 140.4, 140.1, 119.05, 118.95, 65.7, 64.5, 59.1, 58.9, 53.2, 52.7, 32.1, 32.0, 31.96, 31.2, 30.8, 30.7, 29.6, 29.3, 28.44, 28.37, 26.4, 26.3, 25.8, 21.41, 21.38, 18.2, −5.59, −5.63; IR (CHCl$_3$, cm$^{-1}$) 3009, 2931, 2857, 1707, 1679, 1463, 1361, 1257, 1127, 788; LRMS (EI, rel intensity) 283 (M$^+$, -t-Bu, 1), 251 (11), 223 (13), 138 (100), 75 (13); HRMS (EI) m/z calculated for $C_{19}H_{36}O_3Si$ (M$^+$): 283.1729, found 283.1728.

A 125 mL sulfonation (3-necked) flask was fitted with a gas inlet line, an outlet line with stopcock, and a septum. To this flask was added solid methylene blue (ca. 5 mg) followed by a solution of the above ketone (200 mg, 0.585 mmol) in $CH_2Cl_2$ (60 mL). The resulting solution was cooled to −78° C. while UHP oxygen passed through a drying column was bubbled (ca. 3 mL/s) through the solution. The reaction mixture was then irradiated with UV light (medium pressure Hg lamp) with continuous $O_2$ bubbling just until t.l.c. analysis showed>95% consumption of starting materal (ca. 1 hour). After irradiation, an argon sourse was introduced through the septum, the outlet stopcock was closed, and the gas inlet line was replaced with a stopper. To this reaction mixture, still at −78° C., was then added by cannula a −78° C. solution of t-BuMe$_2$SiOTf (148 μL, 0.644 mmol) in $CH_2Cl_2$ (1.5 mL). The resulting solution was stirred for 8 hours at −78° C. At that time, the reaction was quenched by addition via syringe over 2 minutes of $Et_2N$ (268 μL, 1.93 mmol). The mixture was allowed to warm to room temperature slowly over 10 hours and was then concentrated under reduced pressure to ca. 1 mL total volume. The resulting syrup was purified by column chromatography (Florisil®, 1% to 10% EtOAc/hexanes) to give the desired product, a 1:1 mixture of diastereomers (ca. 140 mg, 0.375 mmol, 64%), as a yellow oil.

To a solution of these trioxane silyl ethers (44 mg, 0.12 mmol) in THF (0.60 mL) at 0° C. was added via cannula a 0° C. solution of Bu$_4$NF (monohydrate, 62 mg, 0.24 mmol) in THF (0.60 mL). This mixture immediately turned to a yellow/brown color. The solution was stirred at 0° C. for 6 hours. The reaction was then quenched with $H_2O$ (5 mL) and ether (5 mL). The organic phase was separated, and the aqueous phase was extracted with ether (5 mL×2). The organic portions were combined, washed with saturated aqueous NaCl, dried over anhydrous $MgSO_4$, filtered, and concentrated under reduced pressure. This crude product was purified by column chromatography (Florisil®, 1% to 20% EtOAc/hexane) to give the desired product, a 1:1 mixture of diastereomers (20 mg, 0.078 mmol, 66%), as a colorless oil: The $C_{4\beta}$-hydroxymethyl trioxane was seperated from its $C_{4\alpha}$diastereomer by HPLC (silica, 5% i-PrOH/hexanes, 3 mL/min, 230 nm, R$_t$=16.2 minutes) to afford a white solid: m.p.=101°–102° C.; $^1$H NMR (CDCl$_3$, 400 MHz) δ 4.95 (d, J=1.2 Hz, 1H), 3.70 (d, ABq, J$_d$=5.2 Hz, Δv$_{AB}$=28.4 Hz, J$_{AB}$=10.8 Hz, 2H), 3.51 (s, 3H), 2.46 (m, 1H), 1.86 (m, 2H), 1.74–1.62 (m, 8H), 1.46 (s, 3H), 1.43 (br s, 1H), 1.28–1.15 (m, 2H); $^{13}$C NMR (CDCl$_3$, 100 MHz) δ 106.0, 104.5, 82.7, 64.8, 57.2, 47.7, 45.8, 35.1, 31.0, 30.8, 24.9, 23.6, 22.8; IR (CHCl$_3$, cm$^{-1}$) 3623, 3011, 2936, 2861, 1446, 1144, 1224, 1021; LRMS (CI, rel intensity) 276 (M+NH$_4^+$, 64), 244 (24), 227 (100), 209 (45), 181 (47), 138 (8); HRMS (CI) m/z calculated for $C_{13}H_{22}O_5$ (M+NH$_4^+$): 276.1811, found 276.1815.

A one dram vial was charged with the above $C_{4\beta}$-hydroxymethyl trioxane (8.3 mg, 0.032 mmol) and dissolved with $CH_2Cl_2$ (0.35 mL). To this solution at room temperature was added Et$_3$N (ca. 5 μL, 0.04 mmol) via syringe followed sequentially by terephthaloyl chloride (3.3 mg, 0.016 mmol) and DMAP (3.9 mg, 0.032 mmol). The mixture was stirred for 5 hours at room temperature, quenched with $H_2O$ (2 mL) and diluted with ether (3 mL). The phases were separated, and the aqueous phase was extracted with ether (3 mL×2). The organic portions were combined, washed with saturated aqueous NaCl, dried over anhydrous $MgSO_4$, filtered, and concentrated under reduced pressure. This crude product was purified by column chromatography (Florisil®, 1% to 10% EtOAc/hexane) to give the desired product 24 (9.8 mg, 0.015 mmol, 94%), as a pale yellow oil. This sample was further purified by HPLC to afford an oily solid: $^1$H NMR (CDCl$_3$, 400 MHz) δ 8.13 (s, 4H), 4.99 (d, J=1.2 Hz, 2H), 4.37 (d, ABq, J$_d$=5.2 Hz, Δv$_{AB}$=64.8 Hz, J$_{AB}$=11.2 Hz, 4H), 3.54 (s, 3H), 2.77 (m, 2H), 1.95 (br q, J=12 Hz, 2H), 1.86 (m, 2H), 1.79–1.62 (m, 14H), 1.48 (s, 6H), 1.29–1.15 (m, 4H); $^{13}$C NMR (CDCl$_3$, 100MHz) δ 165.5, 133.9 129.6, 105.6, 104.2, 82.7, 67.0, 56.9, 45.8, 45.2, 35.2, 31.4, 30.7, 24.9, 23.6, 23.2; IR (CHCl$_3$, cm$^{-1}$) 3031, 2934, 2863, 1719, 1446, 1272, 1122, 1010; LRMS (CI, rel intensity) 664 (M+NH$_4^+$, 1), 604 (8), 544 (17), 364 (13), 198 (30), 181 (100); HRMS (CI) m/z calculated for C$_{34}$H$_{46}$O$_{12}$ (M+NH$_4^+$): 664.3333, found 664.3339.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The embodiments of the invention in which an exclusive property or privilege is claimed are defined as follows:

1. A trioxane dimer compound having antiproliferative and antitumor activities of the formula:

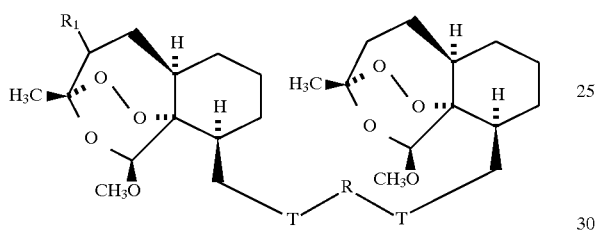

or an enantiomers thereof, wherein:

R$_1$ is CH$_3$, PhCH$_2$Cl or PhCl$_2$; and
R is a linker when T is CH$_2$O; or
R is oxygen when T is CH$_2$.

2. A compound according to claim 1 wherein T is CH$_2$O and said R is arylene, hetero-arylene, lower alkylene, lower alkenylene, a bivalent phosphate group, sulfur, oxygen, —(CH$_2$CH$_2$O)$_n$— wherein n is 1–20 or —CH$_2$CH$_2$—(XCH$_2$CH$_2$)$_n$— where X is O, S or NY where Y is H (hydrogen) or alkyl and n is 0–20, or R is —W—Z—W— where W is a bivalent ester, carbamate or carbonate species and Z is arylene, polyethylene glycol (PEG), hetero-arylene, lower alkylene, or lower alkenylene, and R$_1$ is hydrogen, a methyl group, chloromethylphenyl (PhCH$_2$Cl), dichlorophenyl (PhCl$_2$) or a benzyl group (PhCH$_2$) or when T is a CH$_2$ group, R is oxygen and R$_1$ is hydrogen, a methyl group, chloromethylphenyl (PhCH$_2$Cl), dichlorophenyl (PhCl$_2$) or a benzyl group (PhCH$_2$).

3. A compound according to claim 1, wherein said R is (CH$_2$CH$_2$O)$_n$ and n is 1–20.

4. A compound according to claim 3, where n is 2.

5. A compound according to claim 3, where n is 3.

6. A compound according to claim 3, where n is 6.

7. A compound according to claim 1, wherein said R is selected from the group consisting of:

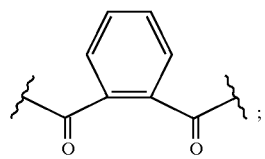

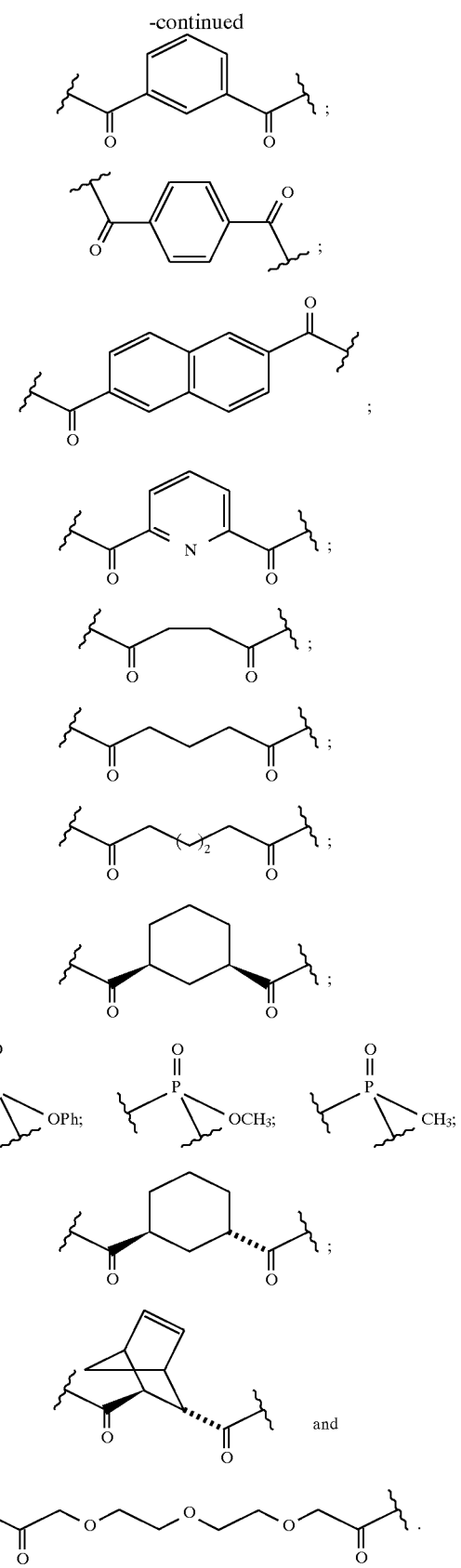

8. A compound according to claim 1, wherein T is CH$_2$, and R is oxygen.

9. A compound according to claim 1, wherein T is CH$_2$, R is oxygen and R$_1$ is a methyl group.

10. A compound according to claim 1, wherein T is CH$_2$, R is oxygen and R$_1$ is chloromethylphenyl.

11. A trioxane dimer compound having antiproliferative and antitumor activities of the formula:

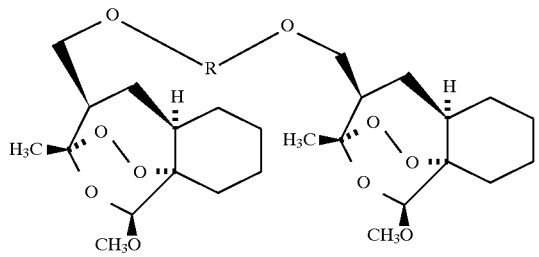

or an enantiomer thereof, wherein:

R is arylene, hetero-arylene, lower alkylene, lower alkenylene, a bivalent phosphate species, sulfur oxygen —(CH$_2$CH$_2$O)$_n$— wherein n is 1–20 or —CH$_2$CH$_2$—(XCH$_2$CH$_2$)$_n$— where X is O, S or NY where Y is H (hydrogen) or alkyl and n is 1–20, or R is —W—Z—W— where W is a bivalent ester, carbamate or carbonate species and Z is arylene, polyethylene glycol (PEG), hetero-arylene, lower alkylene, or lower alkenylene.

12. A compound according to claim 11, wherein R is

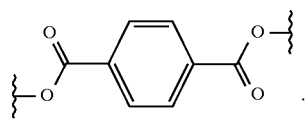

13. A trioxane dimer compound having antiproliferative and antitumor activities of the formula:

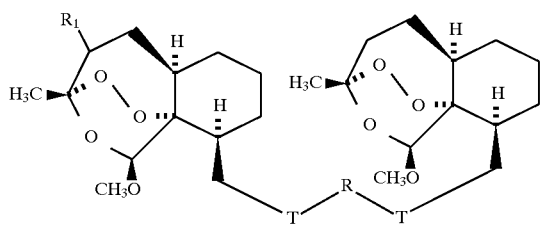

or an enantiomer thereof, wherein:

R$_1$ is H, CH$_3$, PhCH$_2$Cl or PhCl$_2$; and
R is a linker other than

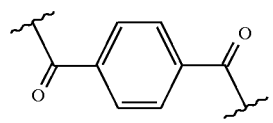

and T is CH$_2$O; or
R is oxygen when T is CH$_2$.

14. A compound according to claim 13, wherein T is CH$_2$O and said R is arylene, hetero-arylene, lower alkylene, lower alkenylene, a bivalent phosphate species, sulfur, oxygen, (CH$_2$CH$_2$O)$_n$— wherein n is 1–20 or —CH$_2$CH$_2$—(XCH$_2$CH$_2$)$_n$— where X is O, or NY where Y is H (hydrogen) or alkyl and n is 1–20, or R is —W—Z—W— where W is a bivalent ester, carbamate or carbonate species and Z is arylene, polyethylene glycol (PEG), hetero-arylene, lower alkylene, or lower alkenylene, and R$_1$ is hydrogen, a methyl group, chloromethylphenyl (PhCH$_2$Cl), dichlorophenyl (PhCl$_2$) or a benzyl group (PhCH$_2$) or when T is CH$_2$, R is oxygen and R$_1$ is hydrogen, a methyl group, chloromethylphenyl (PhCH$_2$Cl), dichlorophenyl (PhCl$_2$) or a benzyl group (PhCH$_2$).

15. A compound according to claim 14, wherein said R is (CH$_2$CH$_2$O), and n is 1–20.

16. A compound according to claim 15, where n is 2.

17. A compound according to claim 15, where n is 3.

18. A compound according to claim 15, where n is 6.

19. A compound according to claim 13, wherein T is CH$_2$, R is oxygen and R$_1$ is hydrogen.

20. A compound according to claim 13, wherein T is CH$_2$, R is oxygen and R$_1$ is a methyl group.

21. A compound according to claim 13, wherein T is CH$_2$, R is oxygen and R$_1$ is chloromethylphenyl.

22. A trioxane dimer compound having antiproliferative and antitumor activities of the formula:

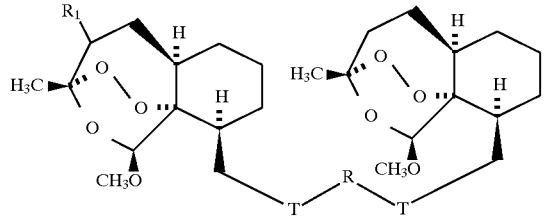

or an enantiomer thereof, wherein:

R$_1$ is H, CH$_3$, PhCl$_2$; and
T is CH$_2$O when R is a linker other than

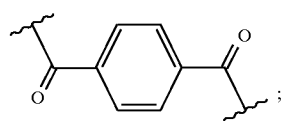

or
R is oxygen when T is CH$_2$.

23. A compound according to claim 22, wherein said R is selected from the group consisting of:

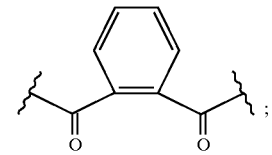

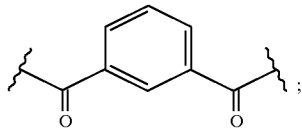

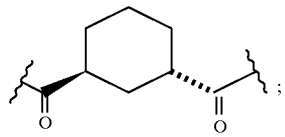

37
-continued
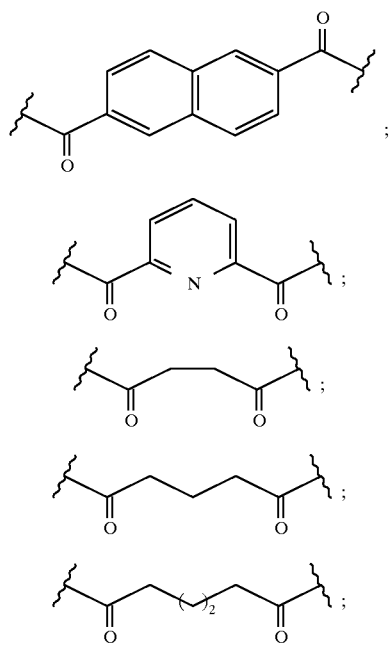
38
-continued
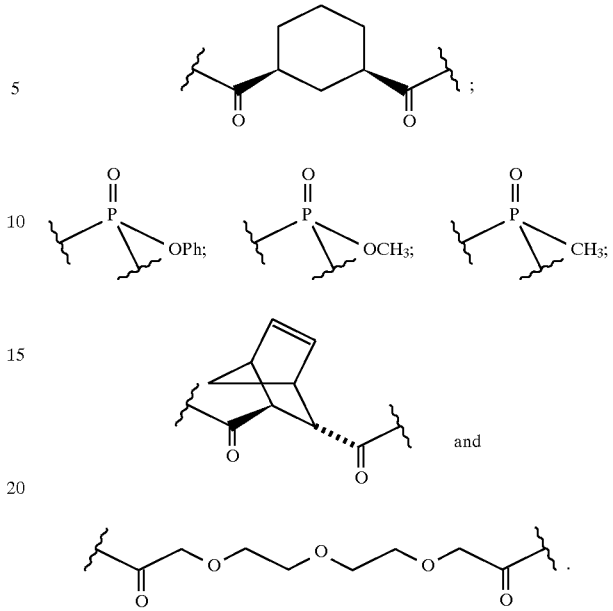
* * * * *